(12) United States Patent
Lukhtanov

US007541454B2

(10) Patent No.: US 7,541,454 B2
(45) Date of Patent: Jun. 2, 2009

(54) COMPOUNDS AND METHODS FOR FLUORESCENT LABELING

(75) Inventor: Eugeny A. Lukhtanov, Bothell, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 526 days.

(21) Appl. No.: 10/975,042

(22) Filed: Oct. 25, 2004

(65) Prior Publication Data

US 2005/0159606 A1 Jul. 21, 2005

Related U.S. Application Data

(60) Provisional application No. 60/514,425, filed on Oct. 24, 2003.

(51) Int. Cl.
*C07D 311/18* (2006.01)
*C07H 21/00* (2006.01)
(52) U.S. Cl. .................. 536/25.32; 435/6; 548/407; 549/53; 549/220; 549/223; 549/224
(58) Field of Classification Search ............... 549/223, 549/224, 225, 53, 220; 435/6; 536/25.32; 548/407
See application file for complete search history.

(56) References Cited

U.S. PATENT DOCUMENTS

| | | | | |
|---|---|---|---|---|
| 4,774,191 | A | * | 9/1988 | Khanna et al. ............... 436/518 |
| 5,162,571 | A | | 11/1992 | Shiraishi et al. |
| 5,187,288 | A | | 2/1993 | Kang et al. |
| 5,188,934 | A | | 2/1993 | Menchen et al. |
| 5,221,611 | A | | 6/1993 | Stenglein et al. |
| 5,227,487 | A | | 7/1993 | Haugland et al. |
| 5,248,782 | A | | 9/1993 | Haugland et al. |
| 5,262,530 | A | | 11/1993 | Andrus et al. |
| 5,304,645 | A | | 4/1994 | Klein et al. |
| 5,419,966 | A | | 5/1995 | Reed et al. |
| 5,433,896 | A | | 7/1995 | Kang et al. |
| 5,442,045 | A | | 8/1995 | Haugland et al. |
| 5,451,343 | A | * | 9/1995 | Neckers et al. ............... 252/582 |
| 5,451,463 | A | | 9/1995 | Nelson et al. |
| 5,512,667 | A | | 4/1996 | Reed et al. |
| 5,556,959 | A | | 9/1996 | Brush et al. |
| 5,583,236 | A | | 12/1996 | Brush |
| 5,589,586 | A | | 12/1996 | Holmberg |
| 5,696,251 | A | | 12/1997 | Arnold, Jr. et al. |
| 5,739,386 | A | | 4/1998 | Holmes |
| 5,808,044 | A | | 9/1998 | Brush et al. |
| 5,942,610 | A | | 8/1999 | Nelson et al. |
| 5,986,086 | A | | 11/1999 | Brush et al. |
| 6,020,481 | A | | 2/2000 | Benson et al. |
| 6,162,931 | A | | 12/2000 | Gee et al. |
| 6,221,604 | B1 | | 4/2001 | Upadhya et al. |
| 6,660,845 | B1 | | 12/2003 | Gall et al. |
| 6,683,173 | B2 | | 1/2004 | Dempcy et al. |

FOREIGN PATENT DOCUMENTS

| | | | |
|---|---|---|---|
| WO | WO 01/64958 | A2 | 9/2001 |
| WO | WO 03/023357 | A2 | 3/2003 |
| WO | WO 03/107144 | A2 | 12/2003 |

OTHER PUBLICATIONS

Boyle, A.L. (ed.): Current Protocols in Nucleic Acid Chemistry, John Wiley and Sons, New York, vol. 1 (2000).
Eckstein (ed.) Oligonucleotide Synthesis: A Practical Approach, IRL Press (1991).
Gait (ed.) Oligonucleotide Synthesis: A Practical Approach, IRL Press (1984).
Greene, T.W. and P.G. Wuts (eds.): Protective Groups in Organic Chemistry, Wiley, 2nd. Ed. (1991).
Harrison, et al. (eds.): Compendium of Synthetic Organic Methods, vols. 1-8, John Wiley and Sons (1971-1996).
Haugland et al.: Handbook of Fluorescent Probes and Research Chemicals, 6th Ed., Molecular Probes, Eugene, Ore. (1996).
Maniatis et al., Molecular Cloning: A Laboratory Manual (1982).
Maniatis et.al., Molecular Cloning: A Laboratory Manual, 2nd Ed., (1989).
March, J. (ed.): Advanced Organic Chemistry, Chapter 4, 4th Ed., John Wiley and Sons, New York (1992).
Berge, S.M. et al.: "Pharmaceutical Salts;" *J. Pharm. Sci.*; vol. 66, pp. 1-19 (1977).
Blickenstaff, R.T. et al., "The synthesis and lithium ammonia reduction of 7-methoxychroman." *Tetrahedron*, vol. 24, pp. 2495-2498 (1968).
Hirshberg, M. et al. "Crystal structure of phosphate binding protein labeled with a coumarin fluorophore, a probe for inorganic phosphate." *Biochemistry*, vol. 37, No. 29; pp. 10381-10385. (1998).
Kendall, et al., "A kinetic study of the hydrolysis of some substituted p-nitroso-dialkylanilines." *J. Am. Chem. Soc.*, vol. 82, pp. 1853-1854 (1960).
Kovacic, P. and M.E. Kurz, "Reactions of t-butylperoxy isopropyl carbonate with aromatic compounds under Friedel-Crafts conditions." *J. Org. Chem*, vol. 31, pp. 2459-2467 (1966).
McGall, G.H. and J.A. Fidanza: "Photolithographic synthesis of high density oligonucleotide arrays;" *Methods Mol. Biol.*, vol. 170, pp. 71-101 (2001).
Plattner, J.J. et al., "Substituted 5,6-dihydrofuro[3,2-f]-1,2-benzisoxazole-6-carboxylic acids: high-ceiling diuretics with uricosuric activity." *J. Med. Chem.*, vol. 27, No. 8; pp. 1016-1026 (1984).
Smith, et al., "The design and properties of a series of calcium indicators which shift from rhodamine-like to fluorescin-like fluorescence on binding calcium." *J. Chem. Soc. Perkin Trans.*, vol. 2, pp. 1195-1204 (1993).
Sun, P. et al., "Tert-butylsulfonyl (Bus), a new protecting group for amines." *J. Org. Chem.*; vol. 62, No. 24; pp. 6469-6475 (1997).
Wada, M. et al., *Bull. Chem. Soc. Jpn.*; vol. 65, No. 5; pp. 1389-1391 (1992).
Whitaker, et al., "Fluorescent rhodol derivatives: versatile, photostable labels and tracers." *Anal. Biochem.*, vol. 207, No. 2., pp. 267-279 (1992).

* cited by examiner

*Primary Examiner*—Bernard Dentz
(74) *Attorney, Agent, or Firm*—Townsend and Townsend and Crew, LLP

(57) ABSTRACT

Compounds useful in the fluorescent labeling of biological materials are provided along with methods for their use and preparation.

20 Claims, No Drawings

COMPOUNDS AND METHODS FOR FLUORESCENT LABELING

CROSS-REFERENCES TO RELATED APPLICATIONS

This application claims the benefit of U.S. Ser. No. 60/514,425, filed Oct. 24, 2003, the disclosure of which is incorporated herein by reference.

BACKGROUND OF THE INVENTION

The non-radioactive detection of biological analytes is an important technology in modern analytical biotechnology. By eliminating the need for radioactive labels, safety is enhanced and the environmental impact of reagent disposal is greatly reduced, resulting in decreased costs for analysis. Examples of methods utilizing such non-radioactive detection include DNA sequencing, oligonucleotide probe methods, detection of polymerase-chain-reaction products, immunoassays, and the like.

In many applications the independent detection of multiple spatially overlapping analytes in a mixture is required, e.g., single-tube multiplex DNA probe assays, immunoassays, multicolor DNA sequencing methods, and the like. In the case of multi-loci DNA probe assays which provide for multicolor detection, the number of reaction tubes is reduced thereby simplifying the experimental protocols and facilitating the manufacturing of application-specific kits. In the case of automated DNA sequencing, multicolor labeling allows for the analysis of all four bases in a single lane thereby increasing throughput over single-color methods and eliminating uncertainties associated with inter-lane electrophoretic mobility variations.

Multiplex detection, however, imposes a number of severe constraints on the selection of dye labels, particularly for analyses requiring an electrophoretic separation and treatment with enzymes, e.g., DNA sequencing.

Due to the variety of constraints imposed of the labeling of biological materials, methodology that is broadly applicable to a variety of dyes is highly desirable. Surprisingly, the present invention provides such methodology, along with compounds that have a long shelf life, making them useful to those engaged in a variety of research efforts, particularly that are useful in carrying out labeling processes.

BRIEF SUMMARY OF THE INVENTION

In one aspect, the present invention provides compounds having the formula A-B, wherein A comprises a hydroxy- or protected hydroxy-substituted fluorescent dye selected from the group consisting of a fluorescein group, a coumarin group, a benzocoumarin group, a xanthene group, a benzo[a]xanthene group, a benzo[b]xanthene group, a benzo[c]xanthene group, a phenoxazine group, a benzo[a]phenoxazine group, a benzo[b]phenoxazine group and a benzo[c]phenoxazine group; and B is an alkanoic acid, a heteroalkanoic acid or acid derivative thereof wherein the alkane or heteroalkane portion of the alkanoic acid, heteroalkanoic acid or acid derivative thereof comprises four or more main chain atoms selected from the group consisting of C, N, O, S and P. The invention also provides compounds that have an emission wavelength of from about 400 nm to about 1200 nm and preferably from about 400 nm to about 850 nm.

Preferably at least one hydroxy- or protected hydroxy-substituent on the fluorescent dye derivative is alpha to the alkanoic acid, heteroalkanoic acid, or derivative thereof.

These compounds are generally provided as having the formula selected from the group consisting of:

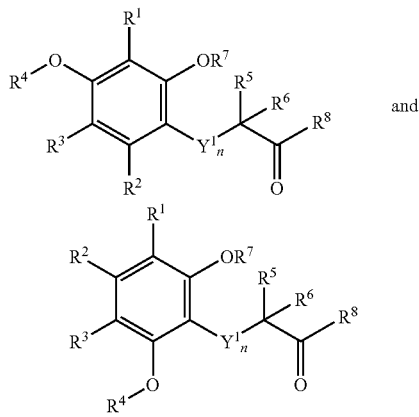

wherein $Y^1$ is selected from the group consisting of $CR^5R^6$, $NR^5$, O, $P(O)_m$ and $S(O)_m$, wherein at least one $CR^5R^6$ is between each member selected from the group consisting of $NR^5$, O, $P(O)_m$ and $S(O)_m$; each $R^1$ or $R^2$ is a member independently selected from the group consisting of H, halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl; $R^3$ and $R^4$ are combined with the phenoxy moiety to which they are attached to form a ring system comprising from 2 to 5 rings, individually selected from the group consisting of five-membered rings, six-membered rings, and combinations thereof, wherein the rings are fused or spiro; optionally substituted with halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl, aryl($C_1$-$C_4$)alkyl and heteroaryl($C_1$-$C_4$)alkyl; each $R^5$ or $R^6$ is a member independently selected from the group consisting of H, ($C_1$-$C_8$)alkyl, aryl, heteroaryl, aryl($C_1$-$C_4$)alkyl and heteroaryl($C_1$-$C_4$)alkyl; $R^7$ is H or a hydroxylprotecting group; $R^8$ is hydroxy, a leaving group that can be displaced by a nucleophilic reagent or $NR^9W(Y^2_pL)$; $R^9$ is H, alkyl or combined with W to form a heterocycloalkylene, heterocycloalkylenearylene, or heterocycloalkyleneheteroarylene linking group; W is a linking group selected from the group consisting of a ($C_2$-$C_{50}$)alkylene, heteroalkylene, ($C_2$-$C_{50}$)cycloalkylene, heterocycloalkylene, ($C_6$-$C_{50}$) arylene group, a heteroarylene group, ($C_2$-$C_{50}$)alkylenearylene group, a heteroalkylenearylene group, optionally substituted with substituents independently selected from the group consisting of ($C_1$-$C_8$)alkyl, hydroxy, protected hydroxyl, alkoxy, amino, protected amino, hydrazino, thio, protected thio and aryl; $Y^2$ is a cleavable linking group selected from the group consisting of:

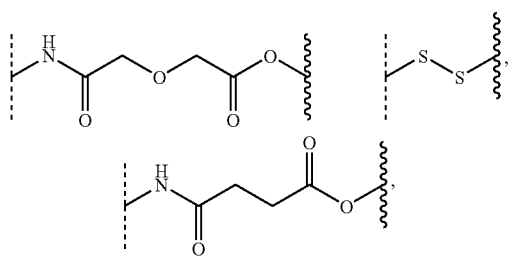

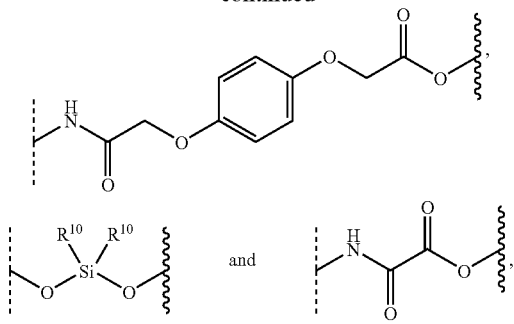

wherein dashed line indicates the point of attachment to L and the wavy line indicates the point of attachment to the rest of the molecule.

each $R^{10}$ is independently $(C_1-C_8)$alkyl or $(C_1-C_8)$alkoxy; the subscript p is an integer of from 0 to 1; L is solid support when p is 1 and L is a member selected from the group consisting of an O-phosphoramidite or a reactive functional group when p is 0; the subscript m is an integer of from about 0 to about 2; the subscript n is an integer of from about 3 to about 19.

In another aspect, the present invention provides compositions comprising a compound of the invention covalently attached to a solid support.

In a related aspect, the present invention provides a method for preparing compounds of the invention.

Intermediates useful in preparing the compounds of the invention are also contemplated as part of the present invention. Thus, additional compounds and methods are provided in which compounds of the invention are further converted to reagents useful in fluorescent labeling processes and particularly in the labeling of biological agents.

In a related aspect, the present invention provides a method for preparing a labeled biological agent, said method comprising contacting an unlabeled biological agent with a compound of the invention under conditions sufficient to covalently attach said compound to said biological agent and form said labeled biological agent.

The present invention also provides biological agents which are covalently modified with a substituent having the formula selected from the group consisting of:

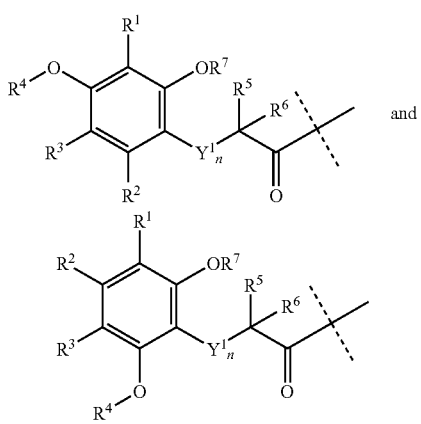

wherein $Y^1$ is selected from the group consisting of $CR^5R^6$, $NR^5$, O, $P(O)_m$ and $S(O)_m$, wherein at least one $CR^5R^6$ is between each member selected from the group consisting of $NR^5$, O, $P(O)_m$ and $S(O)_m$; each $R^1$ or $R^2$ is a member independently selected from the group consisting of H, halogen, cyano, halo$(C_1-C_8)$alkyl, $(C_1-C_8)$alkyl, $(C_1-C_8)$alkylthio, $(C_1-C_8)$alkoxy, aryl and heteroaryl; $R^3$ and $R^4$ are combined with the phenoxy moiety to which they are attached to form a ring system comprising from 2 to 5 rings, individually selected from the group consisting of five-membered rings, six-membered rings, and combinations thereof, wherein the rings are fused or spiro; optionally substituted with halogen, cyano, halo$(C_1-C_8)$alkyl, $(C_1-C_8)$alkyl, $(C_1-C_8)$alkylthio, $(C_1-C_8)$alkoxy, aryl and heteroaryl, aryl$(C_1-C_4)$alkyl and heteroaryl$(C_1-C_4)$alkyl; each $R^5$ or $R^6$ is a member independently selected from the group consisting of H, $(C_1-C_8)$alkyl, aryl, heteroaryl, aryl$(C_1-C_4)$alkyl and heteroaryl$(C_1-C_4)$alkyl; $R^7$ is H or a hydroxylprotecting group; and the dashed line indicates the point of attachment to said biological agent or a linking group joining said biological agent to said substituent.

DETAILED DESCRIPTION OF THE INVENTION

Abbreviations and Definitions

Unless otherwise stated, the following terms used in the specification and claims have the meanings given below:

The term "alkyl" refers to a linear, branched, or cyclic saturated monovalent hydrocarbon radical or a combination of cyclic and linear or branched saturated monovalent hydrocarbon radicals having the number of carbon atoms indicated in the prefix. For example, $(C_1-C_8)$alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, aralkyloxy), when a prefix is not included to indicate the number of main chain carbon atoms in an alkyl portion, the radical or portion thereof will have eight or fewer main chain carbon atoms. The alkyl portions of any of these substitutents are optionally substituted with at least one member selected from the group consisting of halogen, carboxy, sulfo, amino, mono$(C_1-C_6)$alkylamino, di$(C_1-C_6)$alkylamino, $(C_1-C_6)$alkoxy, cyano, haloacetyl and hydroxyl.

The term "alkylene" means a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene, and the like.

The term "alkenyl" refers to a linear monovalent hydrocarbon radical or a branched monovalent hydrocarbon radical having the number of carbon atoms indicated in the prefix and containing at least one double bond. For example, $(C_2-C_6)$ alkenyl is meant to include, ethenyl, propenyl, and the like.

The term "alkynyl" refers to a linear monovalent hydrocarbon radical or a branched monovalent hydrocarbon radical containing at least one triple bond and having the number of carbon atoms indicated in the prefix. For example, $(C_2-C_6)$ alkynyl is meant to include ethynyl, propynyl, and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "aryl" means a monovalent monocyclic or bicyclic aromatic hydrocarbon radical of 6 to 10 ring atoms which is unsubstituted or substituted independently with one to four substituents, preferably one, two, or three substituents selected from $(C_1-C_6)$alkyl, cycloalkyl, cycloalkyl-alkyl, halo, cyano, hydroxy, $(C_1-C_6)$alkoxy, amino, acylamino, mono$(C_1-C_6)$alkylamino, di$(C_1-C_6)$alkylamino, haloalkyl, haloalkoxy, heteroalkyl, sulfo, $(C_1-C_6)$alkylthio, COR (where R is hydrogen, alkyl, cycloalkyl, cycloalkyl-alkyl, phenyl or phenylalkyl), —(CR'R")$_n$—COOR (wherein the subscript n is an integer from 0 to 5, each R' or R" is independently hydrogen or alkyl, and R is hydrogen, alkyl, cycloalkyl, cycloalkylalkyl, phenyl or phenylalkyl) or —(CR'R")$_n$—CONR$^a$R$^b$ (wherein the subscript n is an integer from 0 to 5, R' and R" are independently hydrogen or alkyl, and each R$^a$ or R$^b$ is, independently, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the substituted forms thereof. Similarly, the term "arylene" means a aromatic which is unsubstiuted or substituted as above. Similarly, the term "heteroaryl" refers to those aryl groups wherein one or more heteroatoms or heteroatom functional groups have replaced a ring carbon, while retaining aromatic properties, e.g., pyridyl, quinolinyl, quinazolinyl, thienyl, and the like. For brevity, the term aryl, when used in combination with other radicals (e.g., aryloxy, arylalkyl) is meant to include both aryl groups and heteroaryl groups as described above.

The term "arylalkyl" refers to a radical —R$^a$R$^b$ where R$^a$ is an alkylene group (having the indicated number of carbon atoms, or if unspecified having six or fewer main chain carbon atoms) and R$^b$ is an aryl group as defined herein. Examples of arylalkyl groups include benzyl, phenylethyl, 3-(3-chlorophenyl)-2-methylpentyl, and the like.

Similarly the term "arylalkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group (having the indicated number of carbon atoms) and R$^b$ is an aryl group as defined herein, e.g., 2-hydroxy-2-phenyl-ethyl, 2-hydroxy-1-hydroxymethyl-2-phenyl-ethyl, and the like.

The term "aryloxy", refers to a radical —OR where R is an aryl group, e.g., phenoxy, naphthyloxy and the like.

The prefix "halo" and the term "halogen" when used to describe a substituent, refer to —F, —Cl, —Br and —I.

The term "heteroalkyl" refers to a saturated or unsaturated radical of 2 to 50 atoms exclusive of hydrogen atoms that fill available valences, in which the main chain atoms are selected from C, O, N, S(O)$_n$ or P(O)$_n$ (wherein the subscript n is an integer from about 0 to about 2) with at at least one of the atoms being C, wherein one or two C atoms may optionally be replaced by a carbonyl group. The heteroalkyl may be optionally substituted independently with one, two, or three substituents independently selected from the group consisting of cyano, —OR$^a$, NR$^b$R$^c$, and —S(O)$_n$R$^d$ (where n is an integer from 0 to 2), with the understanding that the point of attachment of the heteroalkyl radical is through a carbon atom of the heteroalkyl radical. R$^a$ is hydrogen, alkyl, aryl, arylalkyl, alkoxycarbonyl, aryloxycarbonyl, carboxamido, or mono-alkylcarbamoyl or di-alkylcarbamoyl. R$^b$ is hydrogen, alkyl, aryl or arylalkyl. R$^c$ is hydrogen, alkyl, aryl, arylalkyl, alkoxycarbonyl, aryloxycarbonyl, carboxamido, mono-alkylcarbamoyl or di-alkylcarbamoyl or alkylsulfonyl. R$^d$ is hydrogen (provided that n is 0), alkyl, aryl, arylalkyl, amino, mono$(C_1-C_6)$alkylamino, di$(C_1-C_6)$alkylamino, or hydroxyalkyl. Representative examples include, for example, 2-hydroxyethyl, 2,3-dihydroxypropyl, 2-methoxyethyl, benzyloxymethyl, 2-cyanoethyl, 2-methylsulfonyl-ethyl, and the like. For each of the above, R$^a$, R$^b$, R$^c$, and R$^d$ can be further substituted by NH$_2$, fluorine, alkylamino, di-alkylamino, OH or alkoxy. Additionally, the prefix indicating the number of carbon atoms (e.g., $C_1-C_{10}$) refers to the total number of carbon atoms in the portion of the heteroalkyl group exclusive of the cyano, —OR$^a$, —NR$^b$R$^c$, or —S(O)$_n$R$^d$ portions.

The term "heterocyclyl" refers to a saturated or unsaturated non-aromatic cyclic radical of 3 to 8 ring atoms in which one or two ring atoms are heteroatoms selected from O, NR (where R is independently hydrogen or alkyl) or S(O)$_n$ (wherein the subscript n is an integer from about 0 to about 2), the remaining ring atoms being C, wherein one or two C atoms may optionally be replaced by a carbonyl group. The heterocyclyl ring may be optionally substituted independently with one, two, or three substituents selected from the group consisting of alkyl, halo, cyano, hydroxy, alkoxy, amino, mono-alkylamino, di-alkylamino, haloalkyl, haloalkoxy, —COR (wherein R is hydrogen, alkyl, cycloalkyl, cycloalkyl-alkyl, phenyl or phenylalkyl), —(CR'R")$_n$—COOR (wherein the subscript n is an integer from 0 to 5, each R' or R" is independently hydrogen or alkyl, and R is hydrogen, alkyl, cycloalkyl, cycloalkyl-alkyl, phenyl or phenylalkyl), or —(CR'R")$_n$—CONR$^a$R$^b$ (wherein the subscript n is an integer from about 0 to about 5, each R' or R" is independently hydrogen or alkyl, and each R$^a$ or R$^b$ is, independently, hydrogen, alkyl, phenyl or phenylalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3-C_{10}$) refers to the total number of carbon atoms in the portion of the heterocyclyl group exclusive of the number of heteroatoms.

The terms "heterocyclylalkyl," "heterocyclylalkenyl," "heterocyclylalkynyl" refer to radicals —R$^a$R$^b$ where R$^a$ is an alkylene, alkenylene or alkynylene group, respectively, and R$^b$ is a heterocyclyl group as defined herein, e.g., tetrahydropyran-2-ylmethyl, 4-methylpiperazin-1-ylethyl, 3-piperidinylmethyl, and the like.

The terms "heteroalkylene" means a linear saturated divalent hydrocarbon radical of one to six carbons or a branched saturated hydrocarbon radical of three to six carbon atoms with one, two or three substituents independently selected from the group consisting of —OR$^a$, —NR$^b$R$^c$, and —S(O)$_n$R$^d$ (wherein the subscript n is an integer from about 0 to about 2), R$^a$, R$^b$, R$^c$, and R$^d$ are as defined herein for a heteroalkyl radical. Examples include, 2-hydroxyethan-1,2-diyl, 2-hydroxypropan-1,3-diyl and the like.

Each of the above terms (e.g., "alkyl," "heteroalkyl," and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, heterocycloalkyl, and heterocycloalkenyl) can be a variety of groups selected from the group consisting of: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to four, preferably, zero, one, two or three substituents. Each R', R" or R'" is independently hydrogen, unsubstituted (C$_1$-C$_8$)alkyl, unsubstituted (C$_1$-C$_8$)heteroalkyl, unsubstituted aryl, aryl substituted with from about Ito about 3 halogens, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, and —C(O)CH$_2$OCH$_3$) and the like. Preferably, the alkyl groups will have from about 0 to about 3 substituents and more preferably 0, 1, or 2 substituents, unless otherwise specified.

Similarly, substituents for the aryl groups are varied and are selected from the group consisting of: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$) alkyl, in a number ranging from zero to the total number of open valences on the aromatic ring system; each R', R" or R'" are is independently selected from the group consisting of hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T or U is independently —NH—, —O—, —CH$_2$— or a single bond, and the subscript q is an integer of from 0 to 2. Alternatively, two of the substituents on adjacent atoms of the aryl or heteroaryl ring may optionally be replaced with a substituent of the formula -A-(CH$_2$)$_r$—B—, wherein A or B is independently —CH$_2$—, —O—, —NH—, —S—, —S(O)—, —S(O)$_2$—, —S(O)$_2$NR'— or a single bond, and r is an integer of from about 1 to about 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, wherein each of the subscripts s or t is independently an integer of from about 0 to about 3, and X is —O—, —NR'—, —S—, —S(O)—, —S(O)$_2$—, or —S(O)$_2$NR'—. The substituent R' in —NR'— and —S(O)$_2$NR'— is hydrogen or unsubstituted (C$_1$-C$_6$)alkyl.

Certain compounds or oligonucleotides of the present invention may exist in a salt form. Such salts include base addition salts such as sodium, potassium, calcium, ammonium, organic amino, magnesium, or a similar salt. When the compounds or modified oligonucleotides of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic, galactunoric acids and the like (see e.g., Berge, S. M., et al. "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention. The methods for the determination of stereochemistry and the separation of isomers are well-known in the art (see discussion in Chapter 4 of "Advanced Organic Chemistry", 4th edition J. March, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not (e.g., $^2$H), are intended to be encompassed within the scope of the present invention.

In many instances the compounds of the present invention are provided with certain protecting groups that provide the compounds with among other characteristics, more reliable reactivity and a longer shelf-life. "Protecting group" or "protected form thereof" refers to a grouping of atoms that when attached to a reactive group in a molecule masks, reduces or prevents that reactivity. Examples of protecting groups can be found in T. W. Greene and P. G. Wuts, *Protective Groups in Organic Chemistry,* (Wiley, 2nd ed. 1991), Beaucage and Iyer, *Tetrahedron* 48:2223-2311 (1992), and Harrison and Harrison et al., *Compendium of Synthetic Organic Methods,* Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl ethers, alkyl esters, trityl ethers, alkyl ethers, tetrahydropyranyl ethers, trialkylsilyl ethers, allyl ethers, and the like. Additionally, hydroxy groups can be protected by photoremovable groups such as α-methyl-6-nitopiperonyloxycarbonyl, and the like (See generally McGall, G. H. and Fidanza, J. A., "Photolithographic synthesis of high-density olignucleotide arrays" in *DNA Arrays Methods and Protocols*, Rampal J. B (ed.); *Methods in Molecular Biology*, 170: 71-101 (2001), Humana Press, Inc., NY; Boyle, Ann L. (ed.); *Current Protocols in Nucleic Acid Chemistry*, John Wiley and Sons, New York, 2000).

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono-substituted or di-substituted with an alkyl group and situations where the heterocyclo group is not substituted with the alkyl group.

The term "reactive group" refers to a moiety that has at least one nucleophilic group or at least one electrophilic (reactive) group. In some instances a "reactive group" may contain both groups, but in these instances one or both of the groups is typically blocked by a protecting group to control undesired reaction (See T. W. Greene and P. G. Wuts, infra). Examples of nucleophilic groups include —$NH_2$, —$NHNH_2$, —$ONH_2$, —$NHC=(O)NHNH_2$, OH, or —SH. Examples of electrophilic reactive groups include activated esters, acrylamides, acyl azides, acyl halides, aldehyde or ketones, alkyl halides, alkyl sulfonates, anhydrides, aryl halides, aziridines, boronates, carboxylic acids, carbodiimides, diazoalkanes, epoxides, haloacetamides, halotriazines, imidoesters, isocyanates, isothiocyanates, maleimides, phophoramidites, silyl halides, sulfonate ester and sulfonyl halides.

The term "solid support" refers to any support that is compatible with oligonucleotides synthesis, including, for example, glass, controlled pore glass, polymeric materials, polystyrene, beads, coated glass and the like.

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See generally Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

General

The present invention resides in the discovery that a wide variety of fluorescent dyes (or fluorophores) can be prepared having at least one hydroxy- or protected-hydroxy moiety alpha to an alkanoic acid moiety, heteroalkanoic acid moiety, or derivative thereof providing compounds that are shelf-stable and that can be used to label essentially any biological agent (e.g., oligonucleotides, peptides, proteins, probes, and the like). The OH of the carboxylic acid moiety can be modified to form a leaving group that may be displaced with suitable nucleophiles. Such modification includes in situ activation of the OH of the carboxylic acid to form a leaving group that may be displaced with suitable nucleophiles. Accordingly, the invention provides new α-hydroxy or protected-hydroxy, alkanoic acid dyes, heteroalkanoic acid dyes, and derivatives thereof as well as methods of labeling biological agents using these dyes and derivatives. The invention provides further reagents such as phosphoramidite-derivatized dyes that can be prepared from the compounds described herein. Additionally, solid support-bound dyes, similarly prepared from the compounds of the present invention are also described.

This approach to labeling has been found to be compatible with, for example, coumarin dyes, benzocoumarin dyes, fluorescein dyes, rhodol dyes, phenoxazine dyes, benzophenoxazine dyes, xanthene dyes, benzoxanthene dyes, and cyanine dyes.

Examples of these and other suitable dye classes can be found in Haugland, et al., HANDBOOK OF FLUORESCENT PROBES AND RESEARCH CHEMICALS, SIXTH ED., Molecular Probes, Eugene, Oreg. 1996; U.S. Pat. Nos. 5,187,288; 5,188,934; 5,248,782; 5,304,645; 5,433,896; 5,442,045; 5,556,959; 5,583,236; 5,808,044; 5,986,086; 6,020,481; 6,162,931; and 6,221,604; Smith, et al., *J. Chem. Soc. Perkin Trans.* 2, 1993, 1195-1204; Whitaker, et al., *Anal. Biochem.* 207:267-279 (1992); and Hirschberg, et al., *Biochemistry* 37:10381-10385 (1998).

Alkanoic Acid Dyes, Heteroalkanoic Acid Dyes and Derivatives Thereof

As noted above, the invention is broadly applicable to the preparation and use of new alkanoic- and heteroalkanoic dye derivatives using a variety of dyes. In one embodiment, the compounds have the formula A-B, wherein A comprises a hydroxy- or protected hydroxy-substituted fluorescent dye selected from the group consisting of a fluorescein group, a coumarin group, a benzocoumarin group, a xanthene group, a benzo[a]xanthene group, a benzo[b]xanthene group, a benzo[c]xanthene group, a phenoxazine group, a benzo[a]phenoxazine group, a benzo[b]phenoxazine group and a benzo[c]phenoxazine group; and B is a member selected from the group consisting of an alkanoic acid, a heteroalkanoic acid, and acid derivative thereof wherein the alkane portion of the alkanoic acid or derivative and the heteroalkane portion of the heteroalkanoic acid or derivative thereof comprises four to about 20 main chain atoms selected from the group consisting of C, N, O, S and P. In one aspect of this embodiment, the compounds of the present invention comprise 1) an alkanoic or heteroalkanoic acid moiety which can be activated to react with a nucleophilic ligand ($NuR^x$), and 2) alpha to the carboxylic acid moeity, a hydroxyl moiety that can tautomerize to a carbonyl moiety. See Scheme A.

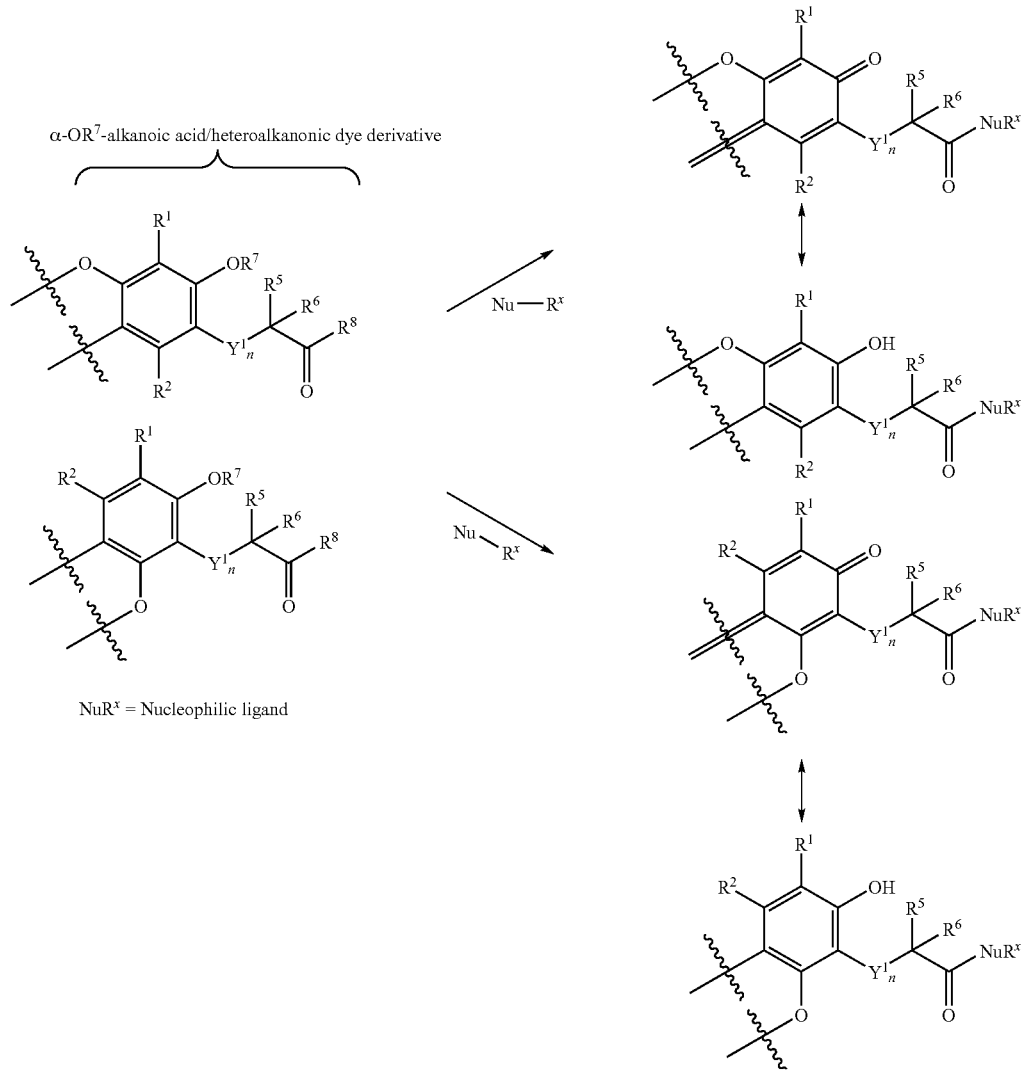

Typically, the nucleophilic ligands are nitrogen nucleophiles (e.g. amines, hydrazines and the like) that are a component of biological compounds (e.g., a nucleic acid, peptide, protein, and the like). The nucleophilic ligand may also be a linking group that is used to attach the fluorescent molecule to, for example, a phosphoramidite group or a solid support. In Scheme A, $Y^1$ is selected from the group consisting of $CR^5R^6$, $NR^5$, O, $P(O)_m$ and $S(O)_m$, wherein at least one $CR^5R^6$ is between each member selected from the group consisting of $NR^5$, O, $P(O)_m$ and $S(O)_m$; each $R^1$ or $R^2$ is a member independently selected from the group consisting of H, halogen, cyano, halo($C_1$-$C_8$)alkyl, ($C_1$-$C_8$)alkyl, ($C_1$-$C_8$) alkylthio, ($C_1$-$C_8$)alkoxy, aryl and heteroaryl; each $R^5$ or $R^6$ is a member independently selected from the group consisting of H, ($C_1$-$C_8$)alkyl, aryl, heteroaryl, aryl($C_1$-$C_4$)alkyl and heteroaryl($C_1$-$C_4$)alkyl; $R^7$ is H or a hydroxylprotecting group; $R^8$ is a leaving group that can be displaced by a nucleophilic reagent; the subscript m is an integer of from about 0 to about 2; and the subscript n is an integer of from about 3 to about 19. Compounds wherein n is 3, 4, 5, 6, 7, 8, 9, 10, 11, 12, 13, 14, 15, 16, 17, 18 and 19 are equally preferred.

In another embodiment, the compounds of the present invention have a formula selected from the group consisting of:

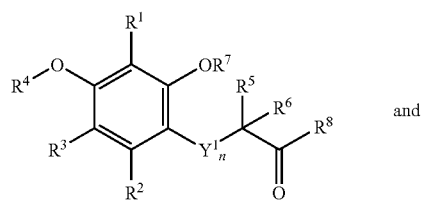

and

-continued

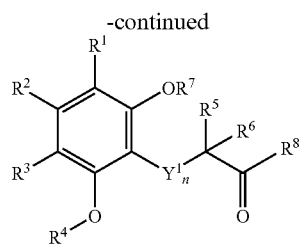

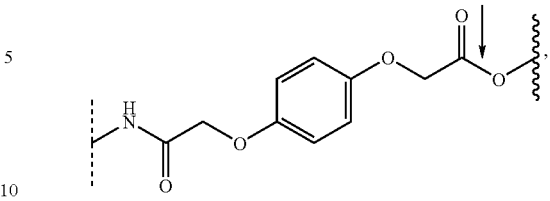

wherein
Y$^1$ is selected from the group consisting of CR$^5$R$^6$, NR$^5$, O, P(O)$_m$ and S(O)$_m$, wherein at least one CR$^5$R$^6$ is between each member selected from the group consisting of NR$^5$, O, P(O)$_m$ and S(O)$_m$; each R$^1$ or R$^2$ is a member independently selected from the group consisting of H, halogen, cyano, halo(C$_1$-C$_8$)alkyl, (C$_1$-C$_8$)alkyl, (C$_1$-C$_8$)alkylthio, (C$_1$-C$_8$)alkoxy, aryl and heteroaryl; R$^3$ and R$^4$ are combined with the phenoxy moiety to which they are attached to form a ring system comprising from 2 to 5 rings, individually selected from the group consisting of five-membered rings, six-membered rings, and combinations thereof, wherein the rings are fused or spiro; optionally substituted with halogen, cyano, halo(C$_1$-C$_8$)alkyl, (C$_1$-C$_8$)alkyl, (C$_1$-C$_8$)alkylthio, (C$_1$-C$_8$)alkoxy, aryl and heteroaryl, aryl(C$_1$-C$_4$)alkyl and heteroaryl(C$_1$-C$_4$)alkyl; wherein the alkyl portions of any of these substituents are optionally substituted with halogen, carboxy, sulfo, amino, mono(C$_1$-C$_6$)alkylamino, di(C$_1$-C$_6$)alkylamino, (C$_1$-C$_6$)alkoxy, cyano, haloacetyl or hydroxy; and the aryl portions of any of these substitutents are optionally substituted with from one to four substituents selected from the group consisting of halogen, cyano, carboxy, sulfo, hydroxy, amino, mono(C$_1$-C$_6$)alkylamino, di(C$_1$-C$_6$)alkylamino, (C$_1$-C$_6$)alkyl, (C$_1$-C$_6$)alkylthio and (C$_1$-C$_6$)alkoxy; each R$^5$ or R$^6$ is a member independently selected from the group consisting of H, (C$_1$-C$_8$)alkyl, aryl, heteroaryl, aryl(C$_1$-C$_4$)alkyl and heteroaryl(C$_1$-C$_4$)alkyl; R$^7$ is H or a hydroxyl protecting group; R$^8$ is hydroxy, a leaving group that can be displaced by a nucleophilic reagent or NR$^9$W(Y$^2_p$L); R$^9$ is H, alkyl or combined with W to form a heterocycloalkylene, heterocycloalkylenearylene, or heterocycloalkyleneheteroarylene linking group; W is a linking group selected from the group consisting of a (C$_2$-C$_{50}$)alkylene, heteroalkylene, (C$_2$-C$_{50}$)cycloalkylene, heterocycloalkylene, (C$_6$-C$_{50}$)arylene group, a heteroarylene group, (C$_2$-C$_{50}$)alkylenearylene group, a heteroalkylenearylene group, optionally substituted with substituents independently selected from the group consisting of (C$_1$-C$_8$)alkyl, hydroxy, protected hydroxyl, alkoxy, amino, protected amino, hydrazino, thio, protected thio and aryl; Y$^2$ is a cleavable linking group selected from the group consisting of:

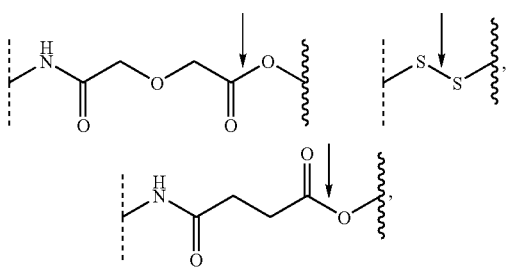

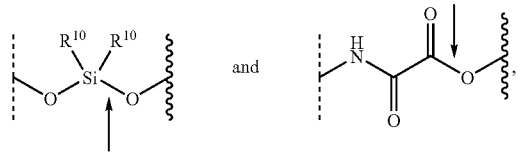

wherein dashed line indicates the point of attachment to L; the wavy line indicates the point of attachment to the rest of the molecule, and the arrow indictes the cleavage point; each R$^{10}$ is independently (C$_1$-C$_8$)alkyl or (C$_1$-C$_8$)alkoxy; the subscript p is an integer of from 0 to 1; L is solid support when p is 1 and L is a member selected from the group consisting of an O-phosphoramidite or a reactive functional group when p is 0; the subscript m is an integer of from about 0 to about 2; the subscript n is an integer of from about 3 to about 19. Compounds wherein n is 3, 4, 5, 6, 7, 8, 9, 10, 11, 12, 13, 14, 15, 16, 17, 18 and 19 are equally preferred.

Examples of W alone or taken with R$^9$ are bifunctional linker, trifunctional linker or polyfunctional linker described in detail in the literature, including but not limited to: a 3'-alkylamine linker as described in U.S. Pat. No. 5,419,966; a hydroxyprolinol-based linker as described in U.S. Pat. No. 5,512,667, a tri- and tetrafunctional linker as described in U.S. Pat. Nos. 5,451,463, 5,942,610 and 5,696,251; or a photocleavable linker as described in U.S. Pat. No. 5,739,386. A trifunctional linker is also available from Glen Research, (Sterling, Va.).

Preferred combinations of R$^3$ and R$^4$ result in fluorescent dye derivatives selected from the group consisting of a coumarin group, a benzocoumarin group, a xanthene group, a benzo[a]xanthene group, a benzo[b]xanthene group, a benzo[c]xanthene group, a phenoxazine group, a benzo[a]phenoxazine group, a benzo[b]phenoxazine group and a benzo[c]phenoxazine group. In addition, the radical Y$^1$ is preferably CR$^5$R$^6$.

In another embodiment, the compounds of the invention have a formula selected from the group consisting of:

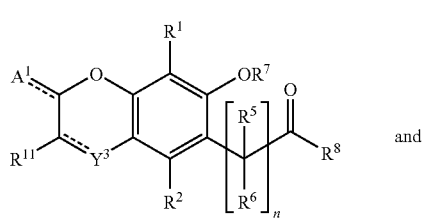

and

-continued

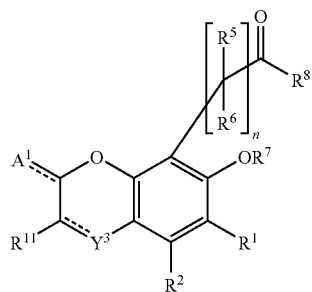

wherein

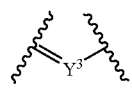

is a member selected from the group consisting of =N—, =CR$^{12}$—, and

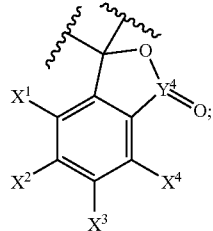

$Y^4$ is C, S, or SO; each $X^1$, $X^2$, $X^3$ and $X^4$ is a member independently selected from the group consisting of H, halogen, cyano, halo($C_1$-$C_8$)alkyl, ($C_1$-$C_8$)alkyl, ($C_1$-$C_8$)alkoxy, ($C_1$-$C_8$)alkylthio, ($C_2$-$C_8$)alkenyl, ($C_2$-$C_8$)alkynyl, $SO_3H$ and $CO_2H$, or any two adjacent $X^1$, $X^2$, $X^3$, and $X^4$ are combined to form a fused aromatic or heteroaromatic ring that is optionally further substituted with from one to four substituents selected from the group consisting of halogen cyano, carboxy, sulfo, hydroxy, amino, mono($C_1$-$C_6$)alkylamino, di($C_1$-$C_6$)alkylamino, ($C_1$-$C_6$)alkyl, ($C_1$-$C_6$)alkylthio and ($C_1$-$C_6$)alkoxy; the moiety

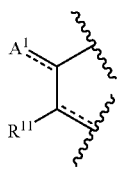

is a member selected from the group consisting of:

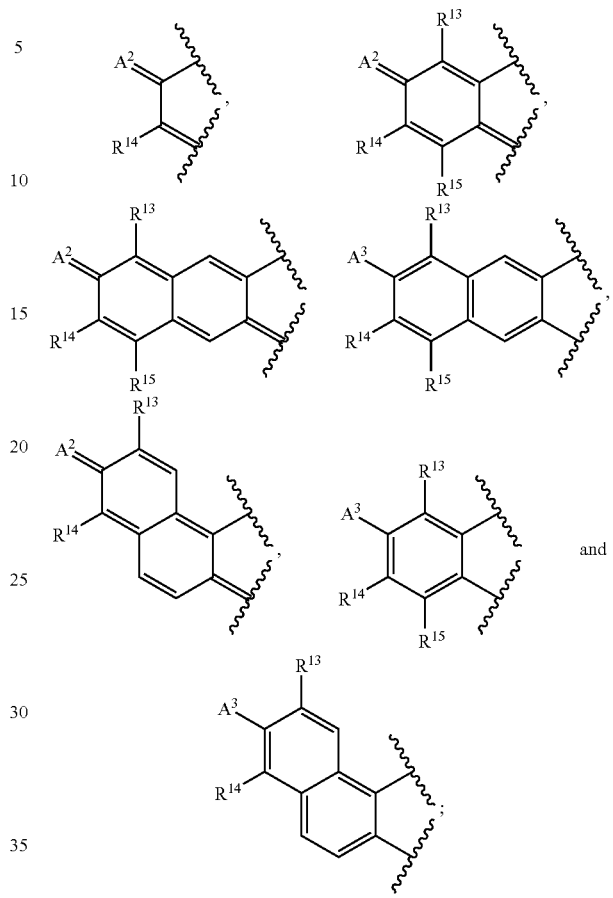

optionally substituted with a member independently selected from the group consisting of halogen, cyano, halo($C_1$-$C_8$) alkyl, ($C_1$-$C_8$)alkoxy, ($C_1$-$C_8$)alkylthio, ($C_2$-$C_8$)alkenyl, ($C_2$-$C_8$)alkynyl, aryl, heteroaryl, $SO_2H$ and $CO_2H$; $A^2$ is O, $NZ^1$ or $N^+(Z^1)(Z^2)$; each $Z^1$ or $Z^2$ is independently H or ($C_1$-$C_8$) alkyl, or is combined with either $R^{13}$ or $R^{14}$ and the atoms which attach them to form a 5-membered ring or a 6-membered ring, or is combined with both of $R^{13}$ and $R^{14}$ and the atoms which attach them to form two fused 6-membered rings; $A^3$ is hydroxyl, protected hydroxyl or $N(Z^1)(Z^2)$; each $Z^1$ or $Z^2$ is independently H or ($C_1$-$C_8$)alkyl, or is combined with either $R^{13}$ or $R^{14}$ and the atoms which attach them to form a 5-membered ring or a 6-membered ring, or is combined with both of $R^{13}$ and $R^{14}$ and the atoms which attach them to form two fused 6-membered rings; each $R^1$ or $R^2$ is a member independently selected from the group consisting of H, halogen, cyano, halo($C_1$-$C_8$)alkyl, ($C_1$-$C_8$)alkyl, ($C_1$-$C_8$) alkylthio, ($C_1$-$C_8$)alkoxy, aryl and heteroaryl; each $R^5$ or $R^6$ is a member independently selected from the group consisting of H, ($C_1$-$C_8$)alkyl, aryl, heteroaryl, aryl($C_1$-$C_4$)alkyl and heteroaryl($C_1$-$C_4$)alkyl; $R^7$ is H or a hydroxylprotecting group; $R^8$ is hydroxy, a leaving group that can be displaced by a nucleophilic reagent or $NR^9W(Y^2_pL)$; W is a linking group selected from the group consisting of a ($C_2$-$C_{50}$)alkylene, heteroalkylene, ($C_2$-$C_{50}$)cycloalkylene, heterocycloalkylene, ($C_6$-$C_{50}$)arylene group, a heteroarylene group, ($C_2$-$C_{50}$)alkylenearylene group, a heteroalkylenearylene group, optionally substituted with at least one substituent independently selected from the group consisting of $(C_1-C_8)$alkyl, hydroxyl, protected hydroxyl, alkoxy, amino, protected amino, hydrazine, thio, protected thio and aryl; $R^9$ is H, alkyl or combined with W to form a heterocycloalkylene, heterocycloalkylenearylene, or heterocycloalkyleneheteroarylene linking group; $R^{12}$ is a member selected from the group consisting of halogen, cyano, halo$(C_1-C_8)$alkyl, $(C_1-C_8)$alkyl, $(C_2-C_8)$alkenyl, $(C_2-C_8)$alkynyl, heteroaryl and aryl, wherein heteroaryl and aryl are optionally substituted with at least one substituent selected from the group consisting of halogen, cyano, halo $(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, $SO_3H$ and $CO_2H$; $R^{13}$, $R^{14}$ or $R^{15}$ is independently selected from the group consisting of H, halogen, cyano, halo$(C_1-C_8)$alkyl, $(C_1-C_8)$alkyl, $(C_1-C_8)$alkylthio, $(C_1-C_8)$alkoxy, aryl and heteroaryl, or $R^{14}$ and $R^{15}$ is combined with the atoms which attach them to form a 5- or 6-membered aromatic ring; $Y^2$ is a cleavable linking group selected from the group consisting of:

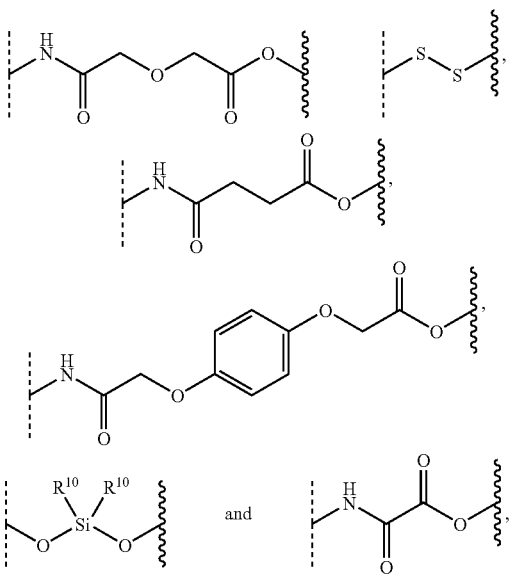

wherein dashed line indicates the point of attachment to L and the wavy line indicates the point of attachment to the rest of the molecule; each $R^{10}$ is independently $(C_1-C_8)$alkyl or $(C_1-C_9)$alkoxy; the subscript p is an integer of from 0 to 1; L is solid support when p is 1 and L is a member selected from the group consisting of an O-phosphoramidite or a reactive functional group when p is 0; the subscript m is an integer of from about 0 to about 2; the subscript n is an integer of from about 4 to about 20. Compounds wherein n is 4, 5, 6, 7, 8, 9, 10, 11, 12, 13, 14, 15, 16, 17, 18, 19 and 20 are equally preferred.

Examples of preferred compounds include 5-(12,15-Dihydroxy-1-oxospiro[3-hydroisobenzofuran-3,9'-xanthene]-11-yl)pentanoic acid; 2,3,4,5,6-Pentafluorophenyl 5-(12,15-dihydroxy-1-oxospiro[3-hydroisobenzofuran-3,9'-xanthene]-11-yl)pentanoate; 5-(12,15-Dihydroxy-1-oxospiro[3-hydroisobenzofuran-3,9'-xanthene]-11-yl)-N-(6-hydroxyhexyl)pentanamide; 5-(12,15-Dihydroxy-1-oxospiro[3-hydroisobenzofuran-3,9'-xanthene]-11-yl)-N-{6-[bis(4-methoxyphenyl)phenylmethoxy]hexyl}pentanamide; 11-[4-(N-{6-[bis(4-methoxyphenyl)phenylmethoxy]hexyl}carbamoyl)butyl]-15-(2,2-dimethylpropanoyloxy)-1-oxospiro[3-hydroisobenzofuran-3,9'-xanthene]-12-yl 2,2-dimethylpropanoate; 15-(2,2-dimethylpropanoyloxy)-11-{4-[N-(6-hydroxyhexyl)carbamoyl]butyl}-1-oxospiro[3-hydroisobenzofuran-3,9'-xanthene]-12-yl 2,2-dimethylpropanoate; and 11-{4-[N-(6-{[bis(methylethyl)amino](2-cyanoethoxy)phosphinooxy}hexyl)carbamoyl]butyl}-15-(2,2-dimethylpropanoyloxy)-1-oxospiro[3-hydroisobenzofuran-3,9'-xanthene]-12-yl 2,2-dimethylpropanoate.

Within the above embodiments preferred compounds are where $R^8$ is OH or a leaving group that can be displaced by a nucleophilic reagent. Further, the leaving group is more preferably a heteroalkyloxy, heteroaryloxy or aryloxy leaving group and even more preferably selected from the group consisting of 1,3-dicyclohexyl-isourea-2-yl, 1-(3-dimethylamino-propyl)-3-ethyl-isourea-2-yl, benzotriazolyloxy, N-succinimidyl, p-nitrophenoxy, pentafluorophenoxy, tetrafluorophenoxy, and pentachlorophenoxy.

In another embodiment preferred compounds are where $R^8$ is $NR^9W(Y^2_pL)$.

Within these embodiments, compounds wherein the moiety

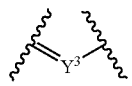

is a member selected from the group consisting of =N—, =CR$^{12}$—, and

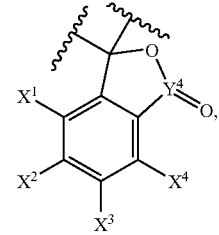

are equally preferred. When the moiety

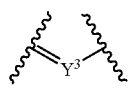

is =CR$^{12}$—; R$^{12}$ is preferably a member selected from the group consisting of: halogen, cyano, halo$(C_1-C_8)$alkyl, $(C_1-C_8)$alkyl, $(C_2-C_8)$alkenyl, $(C_2-C_8)$alkynyl,

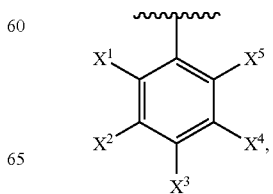 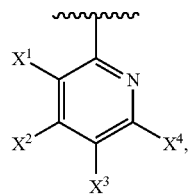

-continued

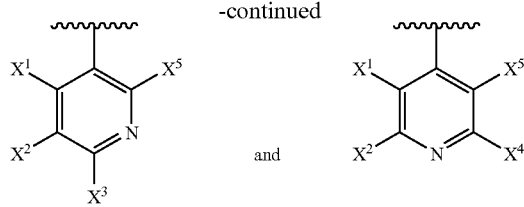

wherein each $X^1$, $X^2$, $X^3$, $X^4$ and $X^5$ is a member independently selected from the group consisting of H, halogen, cyano, halo($C_1$-$C_8$)alkyl, ($C_1$-$C_8$)alkyl, ($C_1$-$C_8$)alkoxy, ($C_1$-$C_8$)alkylthio, ($C_2$-$C_8$)alkenyl, ($C_2$-$C_8$)alkynyl, $SO_3H$ and $CO_2H$, or any two adjacent $X^1$, $X^2$, $X^3$, $X^4$ and $X^5$ are combined to form a fused aromatic or heteroaromatic ring that is optionally further substituted with from one to four substituents selected from halogen cyano, carboxy, sulfo, hydroxy, amino, mono($C_1$-$C_6$)alkylamino, di($C_1$-$C_6$)alkylamino, ($C_1$-$C_6$)alkyl, ($C_1$-$C_6$)alkylthio and ($C_1$-$C_6$)alkoxy.

When the moiety

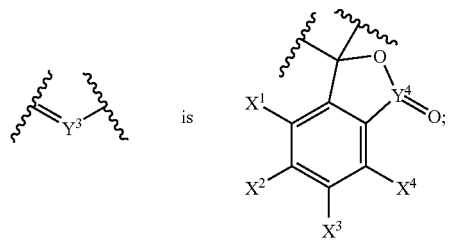

$Y^4$ is preferably C and each $X^1$, $X^2$, $X^3$ and $X^4$ is preferably a member independently selected from the group consisting of H, halogen, cyano, halo($C_1$-$C_8$)alkyl, ($C_1$-$C_8$)alkyl, ($C_1$-$C_8$)alkoxy, ($C_1$-$C_8$)alkylthio, ($C_2$-$C_8$)alkenyl, ($C_2$-$C_8$)alkynyl, $SO_3H$ and $CO_2H$, or any two adjacent $X^1$, $X^2$, $X^3$, and $X^4$ are combined to form a fused aromatic or heteroaromatic ring that is optionally further substituted with from one to four substituents selected from halogen cyano, carboxy, sulfo, hydroxy, amino, mono($C_1$-$C_6$)alkylamino, di($C_1$-$C_6$)alkylamino, ($C_1$-$C_6$)alkyl, ($C_1$-$C_6$)alkylthio and ($C_1$-$C_6$)alkoxy.

While the present invention finds broad application to a number of dyes, certain groups of dyes are preferred and are outlined below. Thus the invention preferably provides compounds that have an emission wavelength of from about 400 nm to about 1200 nm and more preferably from about 400 nm to about 850 nm.

A. Xanthenes (Fluoresceins and Rhodols)

In another embodiment, the compounds of the invention comprise xanthene dyes. One aspect of this embodiment, compounds have the formula selected from the group consisting of:

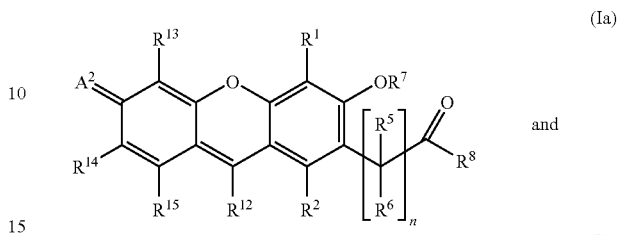

(Ia)

and

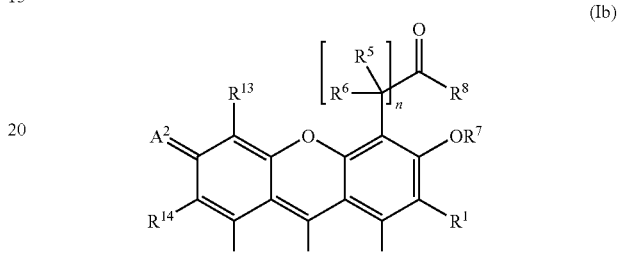

(Ib)

wherein $A^2$ is O, $NZ^1$ or $N^+(Z^1)(Z^2)$; each $Z^1$ or $Z^2$ is independently H, ($C_1$-$C_8$)alkyl, or is combined with either $R^{13}$ or $R^{14}$ and the atoms which attach them to form a 5-membered ring or a 6-membered ring, or is combined with both of $R^{13}$ and $R^{14}$ and the atoms which attach them to form two fused 6-membered rings; each $R^1$, $R^2$, $R^{13}$, $R^{14}$ or $R^{15}$ is independently selected from the group consisting of H, halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl, or $R^{14}$ and $R^{15}$ is combined with the atoms which attach them to form a 5- or 6-membered aromatic ring; each $R^5$ or $R^6$ is independently selected from the group consisting of H, ($C_1$-$C_8$)alkyl, aryl, heteroaryl, aryl($C_1$-$C_4$)alkyl and heteroaryl($C_1$-$C_4$)alkyl; $R^7$ is H or a hydroxylprotecting group; n is an integer of from about 4 to about 20.

In certain embodiments, the compounds of formula Ia and Ib (as well as other formula herein) will be present in isomeric or tautomeric forms (e.g., spirolactones that result from compounds in which $R^{12}$ is substituted phenyl or pyridyl and $X^1$ or $X^5$ is $CO_2H$, $SO_2H$ or $SO_3H$) and are included in this invention.

Scheme B

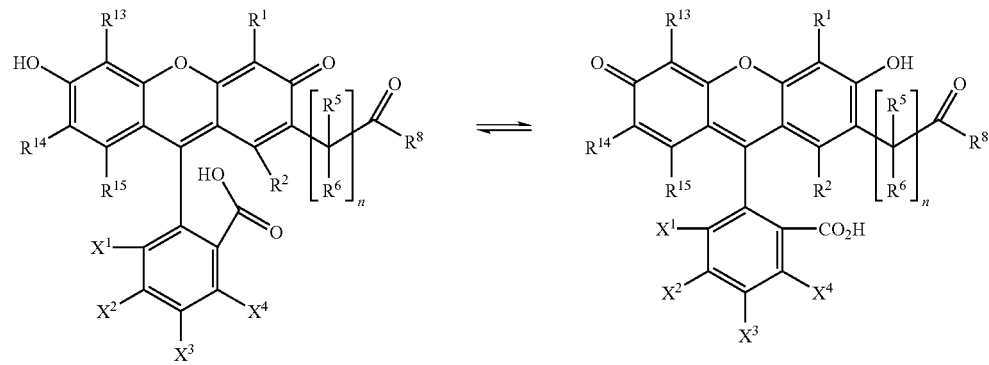

As shown in Scheme B, the tautomeric form having a hydroxy or amino group (not shown) positioned between $R^{13}$ and $R^{14}$ is also contemplated by the present invention. Protected forms are also contemplated by the present invention. Thus the present invention includes compounds of the formulas wherein $A^2$ is O, $NZ^1$ or $N^+(Z^1)(Z^2)$ or $A^3$ is OH, a protected hydroxy group, $A^3$ is hydroxyl, protected hydroxyl or $N(Z^1)(Z^2)$; each $Z^1$ or $Z^2$ is independently H or $(C_1-C_8)$alkyl, or is combined with either $R^{13}$ or $R^{14}$ and the atoms which attach them to form a 5-membered ring or a 6-membered ring, or is combined with both of $R^{13}$ and $R^{14}$ and the atoms which attach them to form two fused 6-membered rings, and their tautomeric forms.

Accordingly, in one group of preferred embodiments, the xanthene-based compounds include fluorescein-based dyes having the formula:

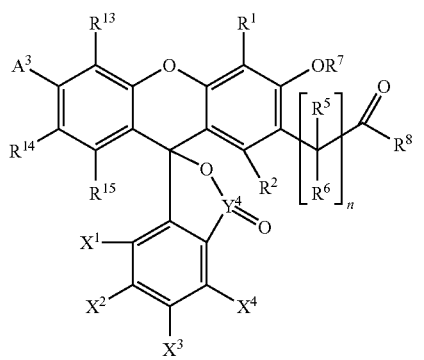

(Ic)

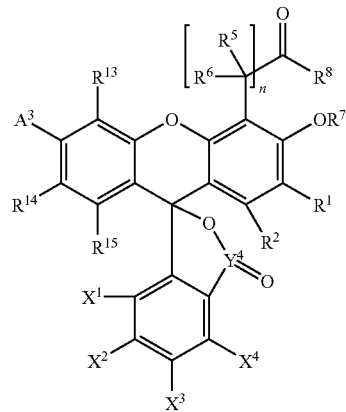

(Id)

wherein $A^3$ is hydroxyl, protected hydroxyl or $N(Z^1)(Z^2)$; each $Z^1$ or $Z^2$ is independently H or $(C_1-C_8)$alkyl, or is combined with either $R^{13}$ or $R^{14}$ and the atoms which attach them to form a 5-membered ring or a 6-membered ring, or is combined with both of $R^{13}$ and $R^{14}$ and the atoms which attach them to form two fused 6-membered rings; each $R^1$, $R^2$, $R^{13}$, $R^{14}$ and $R^{15}$ is independently selected from the group consisting of H, halogen, cyano, halo$(C_1-C_8)$alkyl, $(C_1-C_8)$alkyl, $(C_1-C_8)$alkylthio and $(C_1-C_8)$alkoxy, or $R^{15}$ is combined with $R^{14}$ and the atoms which attach them to form a 5- or 6-membered aromatic ring; each $R^5$ and $R^6$ is independently selected from H, $(C_1-C_8)$alkyl, aryl and aryl$(C_1-C_4)$alkyl; $R^7$ is H or a hydroxyl protecting group; n is an integer from 4 to about 20; $Y^4$ is C, S, or SO; and each $X^1$, $X^2$, $X^3$ and $X^4$ is a member independently selected from the group consisting of H, halogen, cyano, halo$(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$ alkynyl, $SO_3H$ and $CO_2H$, or any two adjacent $X^1$, $X^2$, $X^3$, and $X^4$ are combined to form a fused aromatic or heteroaromatic ring that is optionally further substituted with from one to four substituents selected from halogen cyano, carboxy, sulfo, hydroxy, amino, mono$(C_1-C_6)$alkylamino, di$(C_1-C_6)$ alkylamino, $(C_1-C_6)$alkyl, $(C_1-C_6)$alkylthio and $(C_1-C_6)$ alkoxy.

Further preferred are those compounds of formula Ic and Id wherein $A^3$ is hydroxy or a protected hydroxy. Preferred protecting groups are acyl groups derived from $(C_2-C_{20})$alkanoic acids (e.g., acetyl, propionyl, pivaloyl, isobutyryl, and the like). More preferred are those compounds of formula Ic or Id in which $R^1 R^2$, $R^5$, $R^6$, $R^7$, $R^{13}$, $R^{14}$ and $R^{15}$ are independently selected from H, halogen, $CF_3$ and cyano and $R^8$ is OH. Still further preferred is a compound having a formula:

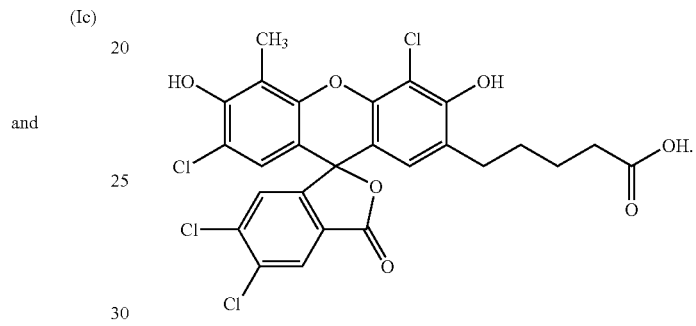

The fluorescein-based compounds of the present invention can generally be prepared according to Scheme I below, in which a suitably substituted resorcinol (i) is reacted with a substituted benzophenone (ii). The carboxylic acid group is then activated to produce the desired compound (iii). Certain substituents are not included in the formula below. A more detailed reaction scheme is provided in the section entitled "General Synthesis".

Scheme 1

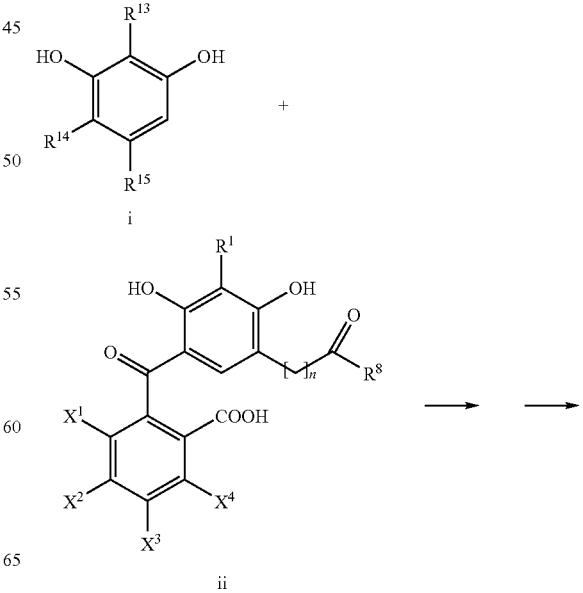

-continued

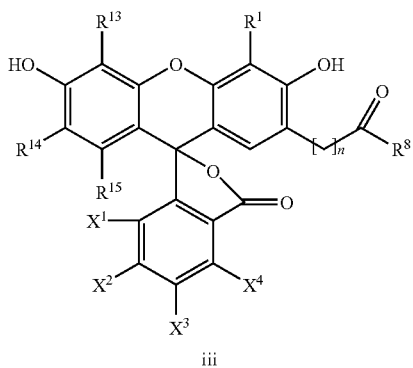

iii

B. Benzo[a]xanthenes

Benzo[a]xanthene-based dyes that are useful in the present methods are provided having the formula:

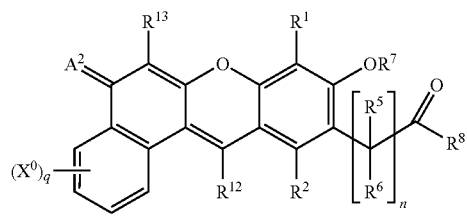
(IIa)

and

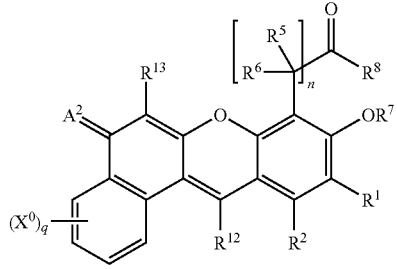
(IIb)

wherein $A^2$ is O, $NZ^1$ or $N^+(Z^1)(Z^2)$; each $Z^1$ or $Z^2$ is independently H, $(C_1-C_8)$alkyl, or is optionally combined with $R^{13}$ and the atoms to which to form a 5- or 6-membered ring; each $X^0$ is a member independently selected from the group consisting of H, halogen, cyano, halo$(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$ and $CO_2H$; each $R^1$, $R^2$ and $R^{13}$ is independently selected from the group consisting of H, halogen, cyano, halo$(C_1-C_8)$alkyl, $(C_1-C_8)$alkyl, $(C_1-C_8)$alkylthio, $(C_1-C_8)$alkoxy, aryl and heteroaryl; each $R^5$ and $R^6$ is independently selected from H, $(C_1-C_8)$alkyl, aryl, heteroaryl, aryl$(C_1-C_4)$alkyl and heteroaryl$(C_1-C_4)$alkyl; $R^7$ is H or a hydroxylprotecting group; the subscript q is an integer of from 0 to 4; and n is an integer from about 4 to about 20.

In a preferred group of embodiments, the compounds have a formula selected from the group consisting of:

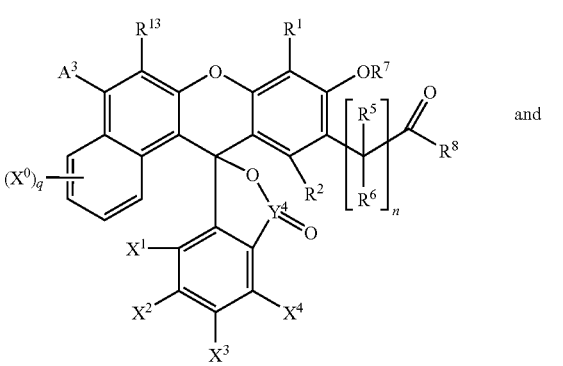
(IIc)

and

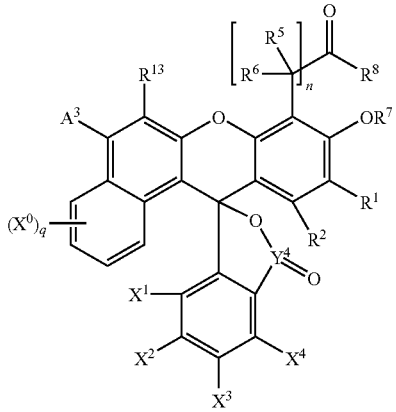
(IId)

wherein $A^3$ is hydroxyl, protected hydroxyl or $N(Z^1)(Z^2)$; each $Z^1$ or $Z^2$ is independently H or $(C_1-C_8)$alkyl, or is combined with either $R^{13}$ or $X^0$ and the atoms which attach them to form a 5-membered ring or a 6-membered ring, or is combined with both of $R^{13}$ and $X^0$ and the atoms which attach them to form two fused 6-membered rings; each $X^0$ is a member independently selected from the group consisting of H, halogen, cyano, halo$(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$ and $CO_2H$; each $R^1$, $R^2$ and $R^{13}$ are independently selected from H, halogen, cyano, halo$(C_1-C_8)$alkyl, $(C_1-C_8)$alkyl, $(C_1-C_8)$alkylthio and $(C_1-C_8)$alkoxy; each $R^5$ and $R^r$ are each independently selected from H, $(C_1-C_8)$alkyl, aryl and aryl$(C_1-C_4)$alkyl; $R^7$ is H or a hydroxyl-protecting group; n is an integer from about 4 to about 20; and the subscript q is an integer of from 0 to 3. Further preferred are those compounds of formula IIc and IId wherein $A^3$ is hydroxy or a protected hydroxy. Preferred protecting groups are acyl groups derived from $(C_2-C_{20})$alkanoic acids (e.g., acetyl, propionyl, pivaloyl, isobutyryl, and the like). More preferably, each $R^1$, $R^2$ and $R^{13}$ are independently selected from the group consisting of H, halogen, $CF_3$ and cyano; and each $X^0$ is H, halogen, $CF_3$ or cyano. In other preferred embodiments, each $X^1$ $X^2$, $X^3$ and $X^4$ is independently selected from H, F or Cl or two of $X^1$ $X^2$, $X^3$ or $X^4$ are combined to form a six-membered aromatic ring. In other particularly preferred embodiments, in the compounds of IIb and IIc, each of $R^5$, $R^6$, $R^7$ is H, and $R^8$ is OH. Most preferred are those embodiments in which $A^3$ is hydroxy or protected hydroxy; each $R^1$, $R^2$, and $R^{13}$ is independently selected from H, halogen, CN and $CF_3$; each of $R^5$, $R^6$, $R^7$ is H, and $R^8$ is OH; each $X^0$ is H, halogen, $CF_3$ or cyano; and each $X^1$ $X^2$, $X^3$ and $X^4$ is independently selected from H, F or Cl.

In general, these compounds can be prepared according to the procedure in Scheme 2.

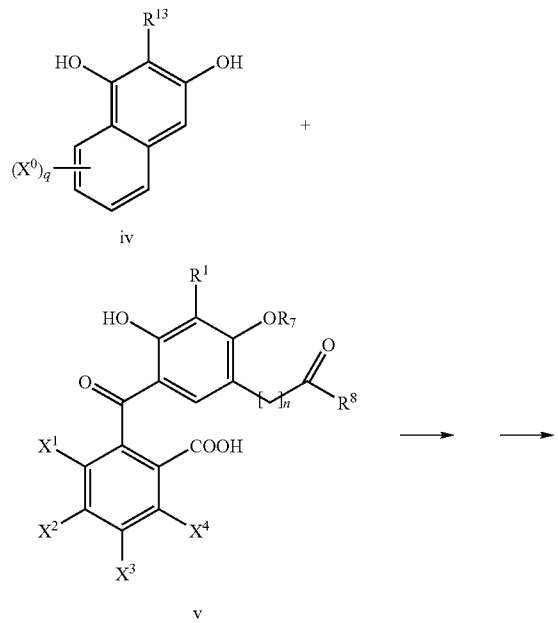

C. Benzo[b]xanthenes

Still other compounds useful in the present invention are the benzo[b]xanthene-based compounds provided in formula (IIIa) and (IIIb) below.

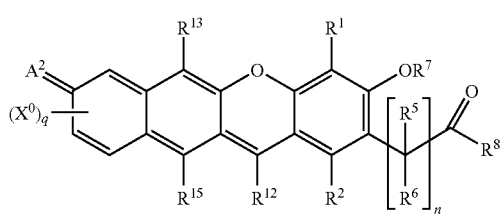

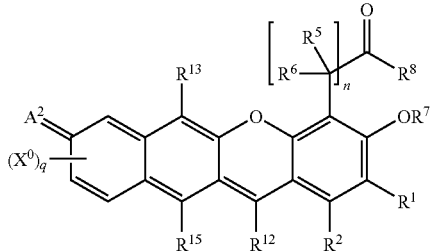

In this formula, $A^2$ is O, $NZ^1$ or $N^+(Z^1)(Z^2)$; each $Z^1$ or $Z^2$ is independently H, $(C_1-C_8)$alkyl, or is optionally combined with an $X^0$ adjacent to $A^2$ and the atoms which attach them to form a 5- or 6-membered ring or is combined with two $X^0$ groups adjacent to $A^2$ and the atoms which attach them to form two fused 6-membered rings; each $X^0$ is a member independently selected from the group consisting of H, halogen, cyano, halo$(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$ and $CO_2H$; each $R^1$, $R^2$, $R^{13}$ and $R^{15}$ is independently selected from H, halogen, cyano, halo$(C_1-C_8)$ alkyl, $(C_1-C_8)$alkyl, $(C_1-C_8)$alkylthio, $(C_1-C_8)$alkoxy, aryl and heteroaryl; each $R^5$ and $R^6$ is independently selected from H, $(C_1-C_8)$alkyl, aryl, heteroaryl, aryl$(C_1-C_4)$alkyl and heteroaryl$(C_1-C_4)$alkyl; $R^7$ is H or a hydroxylprotecting group; the subscript q is an integer of from 0 to 4 and the subscript n is about 4 to about 20. Compounds wherein n is 4, 5, 6, 7, 8, 9, 10, 11, 12, 13, 14, 15, 16, 17, 18, 19 and 20 are equally preferred.

Particularly preferred benzo[b]xanthene-based compounds are provided in formula (IIIc) through (IIId):

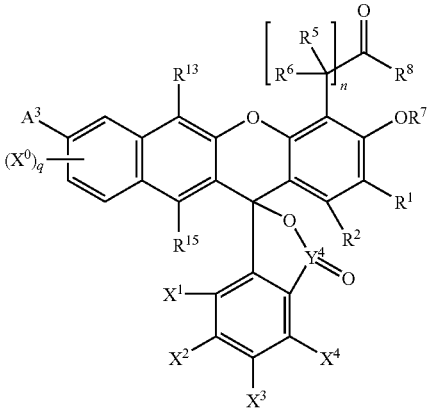

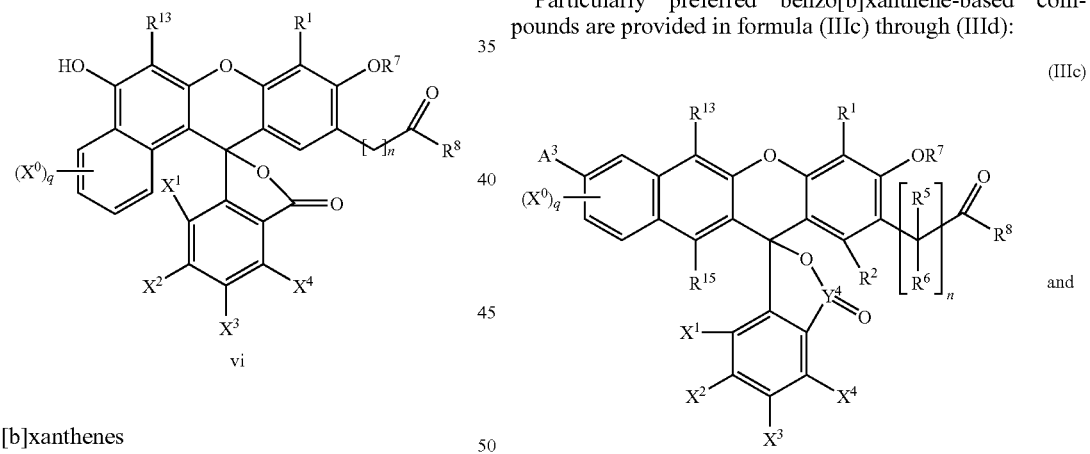

wherein $A^3$ is hydroxyl, protected hydroxyl or $N(Z^1)(Z^2)$; each $Z^1$ or $Z^2$ is independently H or $(C_1-C_8)$alkyl, or is combined with $X^0$ and the atoms which attach them to form a 5- or a 6-membered ring; each $X^0$ is a member independently selected from the group consisting of H, halogen, cyano, halo$(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$ and $CO_2H$; each $R^1$, $R^2$, $R^{13}$ and $R^{15}$ is independently selected from the group consisting of H, halogen, cyano, halo$(C_1-C_8)$alkyl, $(C_1-C_8)$alkyl, $(C_1-C_8)$alkylthio and $(C_1-C_8)$alkoxy; each $R^5$ and $R^6$ is independently selected from H, $(C_1-C_8)$alkyl, aryl and aryl$(C_1-C_4)$alkyl; $R^7$ is H or a hydroxylprotecting group; n is an integer from about 4 to about 20 and the subscript q is an integer of from 0 to 3.

In further preferred embodiments, the present methods employ those compounds of formula IIIa through IIId wherein $A^3$ is hydroxy or a protected hydroxy. Preferred protecting groups are acyl groups derived from $(C_2-C_{20})$alkanoic acids (e.g., acetyl, propionyl, pivaloyl, isobutyryl, and the like). Still further preferred are those compounds of formula IIIa or IIIb in which each $R^1$, $R^2$, $R^3$, $R^{15}$, $X^0$, $X^1$, $X^2$, $X^3$ and $X^4$ are independently selected from H and halogen. Still further preferred are those compounds of formula IIIc or IIId in which $R^1$, $R^2$, $R^{13}$ and $R^{15}$ are independently selected from H, halogen, $CF_3$ and cyano. More preferably, each $X^0$ is H, halogen, $CF_3$ or cyano. In other preferred embodiments, two of $X^1$ through $X^4$ are combined to form a six-membered aromatic or heteroaromatic ring. In other particularly preferred embodiments, in the compounds of IIIc and IIId, each $R^5$, $R^6$ and $R^7$ is H; and $R^8$ is OH. More preferable of the above embodiments, the compound has the formula IIIc.

D. Benzo[c]xanthenes

Still other benzo[c]xanthene-based compounds that are useful in the present invention are provided in formula (IVa) and (IVb):

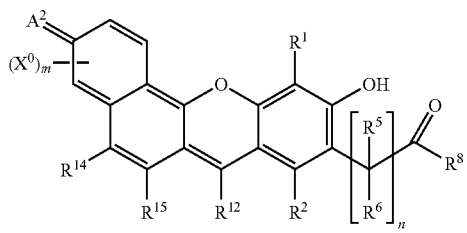

(IVa)

and

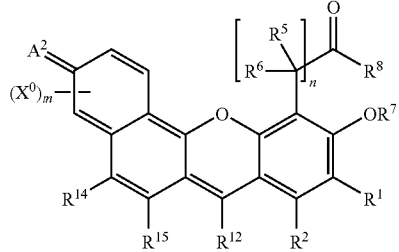

(IVb)

wherein $A^2$ is O, $NZ^1$ or $N^+(Z^1)(Z^2)$; each $Z^1$ or $Z^2$ is independently H, $(C_1-C_8)$alkyl, or is optionally combined with an $X^0$ adjacent to $A^2$ and the atoms which attach them to form a 5- or 6-membered ring or is combined with two $X^0$ groups adjacent to A and the atoms which attach them to form two fused 6-membered rings; each $X^0$ is a member independently selected from the group consisting of H, halogen, cyano, $(C_1-C_8)$haloalkyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$ and $CO_2H$; each $R^1$, $R^2$, $R^{14}$ and $R^{15}$ is independently selected from the group consisting of H, halogen, cyano, halo$(C_1-C_8)$alkyl, $(C_1-C_8)$alkyl, $(C_1-C_8)$alkylthio, $(C_1-C_8)$alkoxy, aryl and heteroaryl, or $R^{14}$ and $R^5$ is combined with the atoms which attach them to form a 5- or 6-membered aromatic ring; each $R^5$ and $R^6$ is independently selected from the group consisting of H, $(C_1-C_8)$alkyl, aryl, heteroaryl, aryl$(C_1-C_4)$alkyl and heteroaryl$(C_1-C_4)$alkyl; $R^7$ is H or a hydroxylprotecting group; the subscript q is an integer of from 0 to 4 and the subscript n is about 4 to about 20. Compounds wherein n is 4, 5, 6, 7, 8, 9, 10, 11, 12, 13, 14, 15, 16, 17, 18, 19 and 20 are equally preferred.

Particularly preferred are benzo[b]xanthene-based compounds having the formula (IVc) and (IVd):

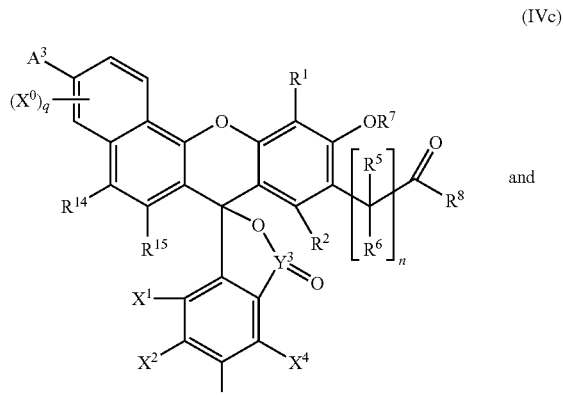

(IVc)

and

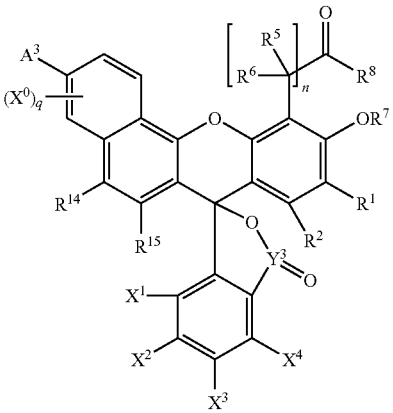

(IVd)

wherein $A^3$ is hydroxyl, protected hydroxyl or $N(Z^1)(Z^2)$; each $Z^1$ or $Z^2$ is independently H or $(C_1-C_8)$alkyl, or is combined with $X^0$ and the atoms which attach them to form a 5- or a 6-membered ring; each $X^0$ is a member independently selected from the group consisting of H, halogen, cyano, halo$(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, aryl, heteroaryl, $SO_3H$ and $CO_2H$; each $R^1$, $R^2$, $R^{14}$ and $R^{15}$ is independently selected from the group consisting of H, halogen, cyano, $CF_3$, $(C_1-C_8)$alkyl, $(C_1-C_8)$alkylthio and $(C_1-C_8)$alkoxy, or $R^{14}$ and $R^{15}$ is combined with the atoms which attach them to form a 5- or 6-membered aromatic ring; each $R^5$ and $R^6$ is independently selected from the group consisting of H, $(C_1-C_8)$alkyl, aryl and aryl$(C_1-C_4)$alkyl; $R^7$ is H or a hydroxyl protecting group; the subscript n is about 4 to about 20; and the subscript q is an integer of from 0 to 3. Compounds wherein n is 4, 5, 6, 7, 8, 9, 10, 11, 12, 13, 14, 15, 16, 17, 18, 19 and 20 are equally preferred.

Compounds of formula IVa through IVd wherein $A^3$ is hydroxy or a protected hydroxyl are further preferred. Preferred protecting groups are acyl groups derived from ($C_2$-$C_{20}$)alkanoic acids (e.g., acetyl, propionyl, pivaloyl, isobutyryl, and the like). Still further preferred are those compounds of formula IVc or IVd in which $R^1$, $R^2$, $R^{14}$ and $R^{15}$ are independently selected from H, halogen, $CF_3$ and cyano. More preferably, each $X^0$ is H, halogen, $CF_3$ or cyano. In other preferred embodiments, two of $X^1$ through $X^4$ are combined with the atoms to which they are attached to form a six-membered aromatic or heteroaromatic ring. In other particularly preferred embodiments, in the compounds of IVc and IVd, each $R^5$, $R^6$ and $R^7$ is H; and $R^8$ is OH. More preferable of the above embodiments, the compound has the formula IVc.

E. Phenoxazines

In still another group of embodiments, the compounds of the invention are represented by the formulae (Va) and (Vb):

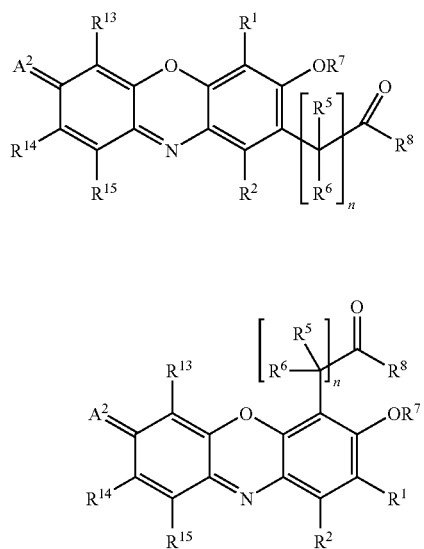

wherein $A^2$ is O, $NZ^1$ or $N^+(Z^1)(Z^2)$; each $Z^1$ or $Z^2$ is independently H, ($C_1$-$C_8$)alkyl, or is optionally combined with an $R^{13}$ or $R^{14}$ and the atoms which attach them to form a 5- or 6-membered ring or is combined with both $R^{13}$ or $R^{14}$ and the atoms which attach them to form two fused 6-membered rings; each $R^1$, $R^2$, $R^{13}$, $R^{14}$ and $R^{15}$ is independently selected from the group consisting of H, halogen, cyano, halo($C_1$-$C_8$) alkyl, ($C_1$-$C_8$)alkyl, ($C_1$-$C_8$)alkylthio, ($C_1$-$C_8$)alkoxy, aryl and heteroaryl, or $R^{14}$ and $R^{15}$ is combined with the atoms which attach them to form a 5- or 6-membered aromatic ring; each $R^5$ and $R^6$ is independently selected from H, ($C_1$-$C_8$) alkyl, aryl, heteroaryl, aryl($C_1$-$C_4$)alkyl and heteroaryl($C_1$-$C_4$)alkyl; $R^7$ is H or a hydroxylprotecting group; and the subscript n is 4 to about 20. Compounds wherein n is 4, 5, 6, 7, 8, 9, 10, 11, 12, 13, 14, 15, 16, 17, 18, 19 and 20 are equally preferred.

In certain preferred embodiments, each $R^1$, $R^2$, $R^{13}$, $R^{14}$ and $R^{15}$ is independently selected from the group consisting of H, halogen, cyano, halo($C_1$-$C_8$)alkyl, ($C_1$-$C_8$)alkyl, ($C_1$-$C_8$)alkylthio and ($C_1$-$C_8$)alkoxy; $R^5$ and $R^6$ are each independently selected from H, ($C_1$-$C_8$)alkyl, aryl and aryl($C_1$-$C_4$) alkyl. Still further preferred are those compounds of formula Va and Vb in which each $R^1$, $R^2$, $R^3$, $R^{14}$ and $R^{15}$ is independently selected from H, halogen, $CF_3$ and cyano. In other particularly preferred embodiments, in the compounds of formula Va and Vb, each of $R^5$, $R^6$, and $R^7$ is H; $R^8$ is OH and each $R^1$, $R^2$, $R^{13}$, $R^{14}$ and $R^{15}$ is independently selected from the group consisting of hydrogen and halogen, more preferably, H, Cl and F.

The phenoxazine-based compounds of the present invention can generally be prepared according to Scheme 3 below, in which a suitably substituted nitrosoresorcinol (vii) is reacted with a suitably substituted methyl (dihydroxy)phenylalkanoate (viii). The acid is then saponified and, optionally, activated to produce the desired compounds (ix). Certain substituents are not included in the formula below.

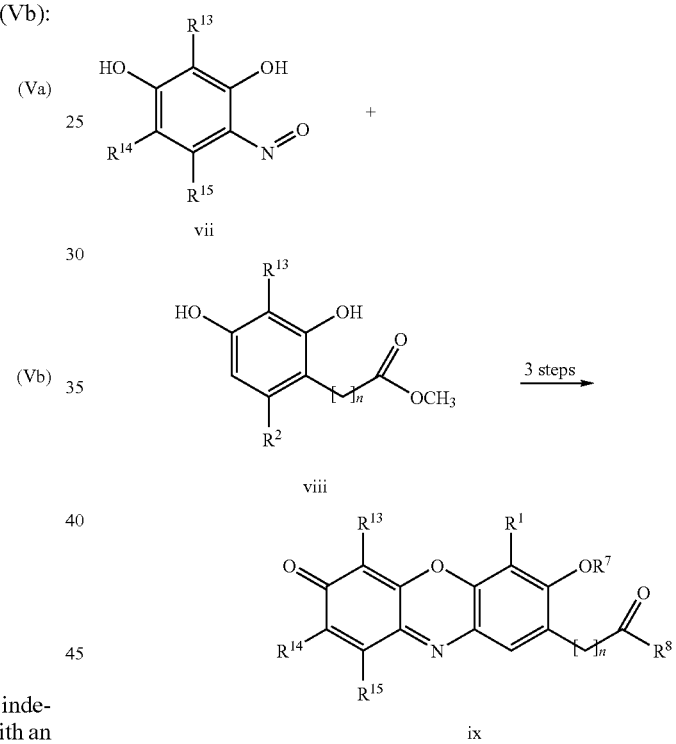

F. Benzo[a]phenoxazines

In a group of related embodiments, the compounds of the invention are based on the benzo[a]phenoxazine dyes and are represented by the formula (VIa) and (VIb):

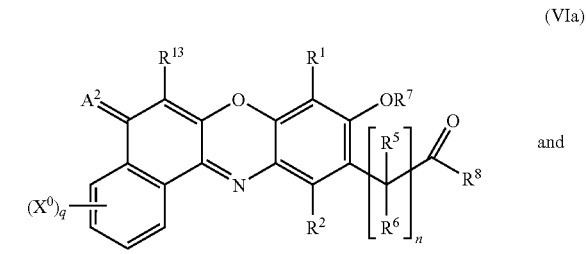

-continued

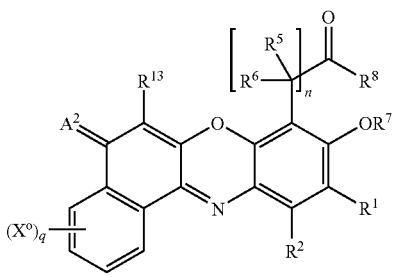
(VIb)

wherein $A^2$ is O, $NZ^1$ or $N^+(Z^1)(Z^2)$; each $Z^1$ or $Z^2$ is independently H, $(C_1$-$C_8)$alkyl, or is optionally combined with $R^{13}$ and the atoms which attach them to form a 5- or 6-membered ring; each $X^0$ is independently selected from the group consisting of H, halogen, cyano, halo$(C_1$-$C_8)$alkyl, $(C_1$-$C_8)$alkyl, $(C_1$-$C_8)$alkoxy, $(C_1$-$C_8)$alkylthio, $(C_2$-$C_8)$alkenyl, $(C_2$-$C_8)$alkynyl, aryl, heteroaryl, $SO_3H$ and $CO_2H$; each $R^1$, $R^2$ and $R^{13}$ is independently selected from the group consisting of H, halogen, cyano, halo$(C_1$-$C_8)$alkyl, $(C_1$-$C_8)$alkyl, $(C_1$-$C_8)$alkylthio, $(C_1$-$C_8)$alkoxy, aryl and heteroaryl; each $R^5$ and $R^6$ is independently selected from the group consisting of H, $(C_1$-$C_8)$alkyl, aryl, heteroaryl, aryl$(C_1$-$C_4)$alkyl and heteroaryl$(C_1$-$C_4)$alkyl; $R^7$ is H or a hydroxylprotecting group; the subscript q is an integer of from about 0 to 4 and the subscript n is an integer of from about 4 to about 20. Compounds wherein n is 4, 5, 6, 7, 8, 9, 10, 11, 12, 13, 14, 15, 16, 17, 18, 19 and 20 are equally preferred.

In certain preferred embodiments, $A^2$ is O; each $R^1$, $R^2$ and $R^{13}$ is independently selected from the group consisting of H, halogen, cyano and $CF_3$; each $R^5$, $R^6$, $R^7$ is H; and $R^8$ is OH.

G. Benzo[b]phenoxazines

Still other compounds useful in the present methods are provided in formula (VIIa) and (VIIb):

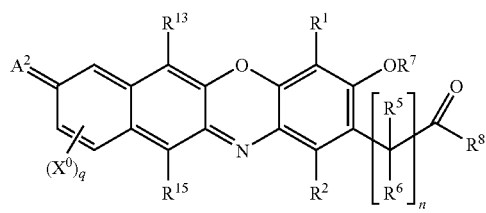
(VIIa)

and

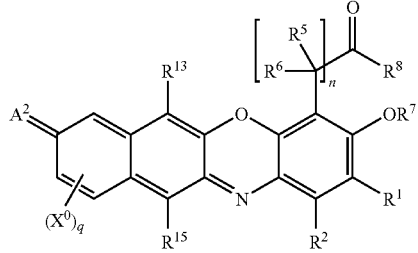
(VIIb)

wherein $A^2$ is O, $NZ^1$ or $N^+(Z^1)(Z^2)$; each $Z^1$ or $Z^2$ is independently H, $(C_1$-$C_8)$alkyl, or is optionally combined with an $X^0$ adjacent to $A^2$ and the atoms which attach them to form a 5- or 6-membered ring or is combined with two $X^0$ groups adjacent to $A^2$ and the atoms which attach them to form two fused 6-membered rings; each $X^0$ is independently selected from the group consisting of H, halogen, cyano, halo$(C_1$-$C_8)$alkyl, $(C_1$-$C_8)$alkyl, $(C_1$-$C_8)$alkoxy, $(C_1$-$C_8)$alkylthio, $(C_2$-$C_8)$alkenyl, $(C_2$-$C_8)$alkynyl, aryl, heteroaryl, $SO_3H$ and $CO_2H$, or optionally, any two adjacent $X^0$ groups can be taken together with the atoms which attach them to form a fused aromatic or heteroaromatic ring; each $R^1$, $R^2$, $R^{13}$ and $R^{15}$ is independently selected from H, halogen, cyano, halo$(C_1$-$C_8)$alkyl, $(C_1$-$C_8)$alkyl, $(C_1$-$C_8)$alkylthio, $(C_1$-$C_8)$alkoxy, aryl and heteroaryl; each $R^5$ and $R^6$ is independently selected from the group consisting of H, $(C_1$-$C_8)$alkyl, aryl, heteroaryl, aryl$(C_1$-$C_4)$alkyl and heteroaryl$(C_1$-$C_4)$alkyl; $R^7$ is H or a hydroxyl protecting group; the subscript q is an integer of from 0 to 4 and the subscript n is about 4 to about 20. Compounds wherein n is 4, 5, 6, 7, 8, 9, 10, 11, 12, 13, 14, 15, 16, 17, 18, 19 and 20 are equally preferred.

In certain preferred embodiments, $A^2$ is O; each $R^1$, $R^2$, $R^{13}$ and $R^{15}$ is independently selected from the group consisting of H, halogen, cyano and $CF_3$; each $R^5$, $R^6$, $R^7$ is H; and $R^8$ is OH.

H. Benzo[c]phenoxazines

Still other compounds are provided in formula VIIIa and VIIIb:

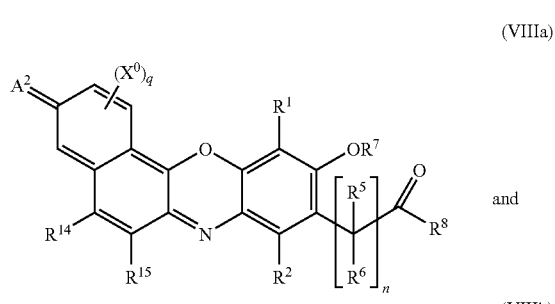
(VIIIa)

and

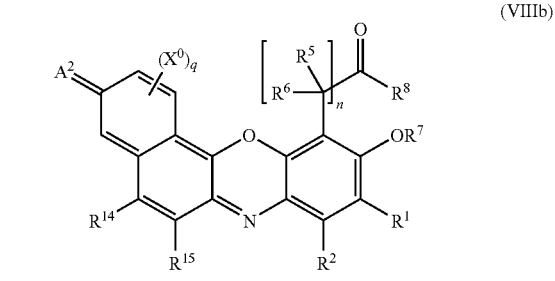
(VIIIb)

wherein $A^2$ is O, $NZ^1$ or $N^+(Z^1)(Z^2)$; each $Z^1$ or $Z^2$ is independently H, $(C_1$-$C_8)$alkyl, or is optionally combined with an $X^0$ adjacent to $A^2$ and the atoms which attach them to form a 5- or 6-membered ring or is combined with two $X^0$ groups adjacent to $A^2$ and the atoms which attach them to form two fused 6-membered rings; each $X^0$ is independently selected from the group consisting of H, halogen, cyano, halo$(C_1$-$C_8)$ alkyl, $(C_1$-$C_8)$alkyl, $(C_1$-$C_8)$alkoxy, $(C_1$-$C_8)$alkylthio, $(C_2$-$C_8)$alkenyl, $(C_2$-$C_8)$alkynyl, aryl, heteroaryl, $SO_3H$ and $CO_2H$; each $R^1$, $R^2$, $R^{14}$ and $R^{15}$ is independently selected from H, halogen, cyano, halo$(C_1$-$C_8)$alkyl, $(C_1$-$C_8)$alkyl, $(C_1$-$C_8)$alkylthio, $(C_1$-$C_8)$alkoxy, aryl and heteroaryl, or $R^{14}$ and $R^{15}$ is combined with the atoms which attach them to form a 5- or 6-membered aromatic ring; each $R^5$ and $R^6$ is independently selected from the group consisting of H, $(C_1$-$C_8)$alkyl, aryl, heteroaryl, aryl$(C_1$-$C_4)$alkyl and heteroaryl$(C_1$-$C_4)$ alkyl; $R^7$ is H or a hydroxylprotecting group; the subscript q is an integer of from 0 to 3 and the subscript n is about 4 to about 20. Compounds wherein n is 4, 5, 6, 7, 8, 9, 10, 11, 12, 13, 14, 15, 16, 17, 18, 19 and 20 are equally preferred.

In certain preferred embodiments, $A^2$ is O; each $R^1$, $R^2$, $R^{14}$ and $R^{15}$ is independently selected from the group consisting of H, halogen, cyano and $CF_3$; each $R^5$, $R^6$, $R^7$ is H; and $R^8$ is OH.

I. Coumarins and Benzocoumarins

The compounds and methods of the present invention also include coumarin and benzocoumarin-based dyes. Coumarin containing dyes useful in the invention, have the formula (IXa) and (IXb):

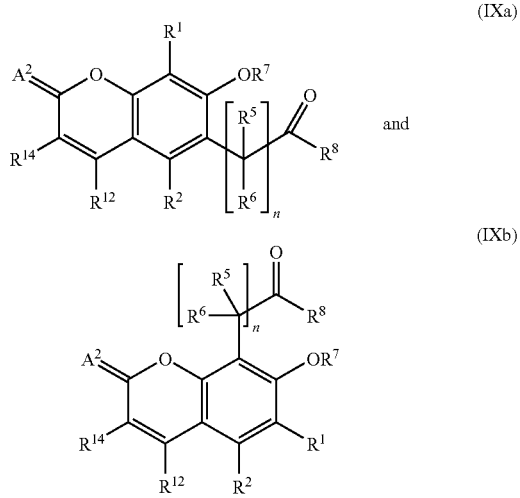

(IXa)

and (IXb)

wherein $A^2$ is O, $NZ^1$ or $N^+(Z^1)(Z^2)$; each $Z^1$ or $Z^2$ is independently H, $(C_1-C_8)$alkyl; each $R^1$, $R^2$, $R^{12}$ and $R^{14}$ is independently selected from the group consisting of H, halogen, cyano, halo$(C_1-C_8)$alkyl, $(C_1-C_8)$alkyl, $(C_1-C_8)$alkylthio, $(C_1-C_8)$alkoxy, aryl and heteroaryl, or $R^{12}$ and $R^{14}$ are taken together with the atoms which attach them to form a fused aromatic ring; each $R^5$ and $R^6$ is independently selected from the group consisting of H, $(C_1-C_8)$alkyl, aryl, heteroaryl, aryl$(C_1-C_4)$alkyl and heteroaryl$(C_1-C_4)$alkyl; $R^7$ is H or a hydroxy protecting group; and the subscript n is about 4 to about 20. Compounds wherein n is 4, 5, 6, 7, 8, 9, 10, 11, 12, 13, 14, 15, 16, 17, 18, 19 and 20 are equally preferred.

In certain preferred embodiments, $R^1$ is H or halogen; $R^2$ is hydrogen; and $R^{14}$ is $(C_1-C_4)$alkyl.

In other preferred embodiments, $R^{12}$ is selected from halogen, cyano, halo$(C_1-C_8)$alkyl, $(C_1-C_8)$alkyl, and aryl or heteroaryl having the formula:

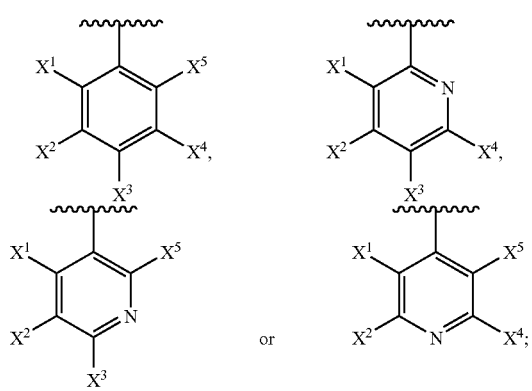

wherein each $X^1$, $X^2$, $X^3$, $X^4$ and $X^5$ is independently selected from the group consisting of H, halogen, cyano, halo$(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, $SO_3H$ and $CO_2H$, and optionally, any two adjacent substituents $X^1$, $X^2$, $X^3$, $X^4$ and $X^5$ can be taken together with the ring to which each is attached to form a fused aromatic or heteroaromatic ring that is optionally further substituted with from one to four substituents selected from halogen cyano, carboxy, sulfo, hydroxy, amino, mono$(C_1-C_6)$alkylamino, di$(C_1-C_6)$alkylamino, $(C_1-C_6)$alkyl, $(C_1-C_6)$alkylthio and $(C_1-C_6)$alkoxy.

In view of the above, the present invention also provides methods for preparing coumarin-based compounds of the invention. These can be prepared as outlined in Scheme 4, wherein n is 4 to about 20, and the other substituents are as defined above.

Scheme 4

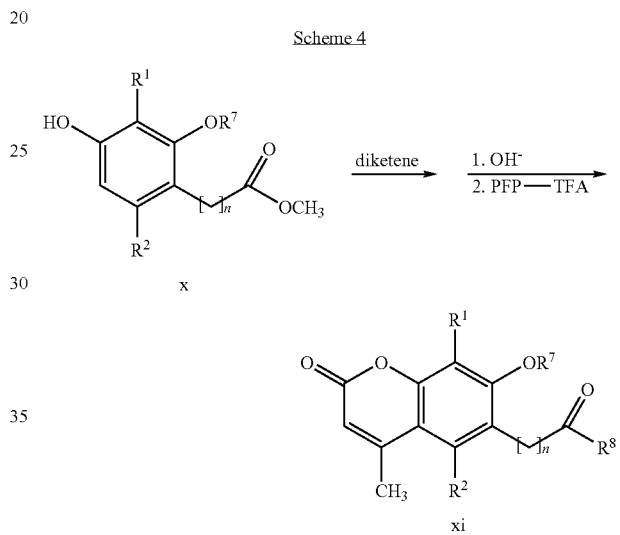

Synthesis of Compounds

In one embodiment, the compounds of the present invention can be prepared and used based on any dye that contains x. In addition to the general schemes shown above, more specific schemes and examples are provided below. Many of the compounds of the invention can be prepared from common intermediates that are readily available to one of skill in the art. One group of particularly useful intermediates are 5-(3-substituted-2,4-dihydroxyphenyl)pentanoates. These compounds can be prepared as outlined below in Scheme 5 below.

Scheme 5
Preparation of 3-substituted methyl 2,4-dihydroxyphenylpropionates

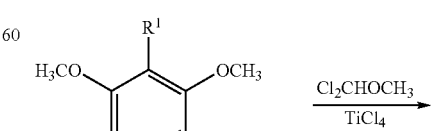

1

-continued

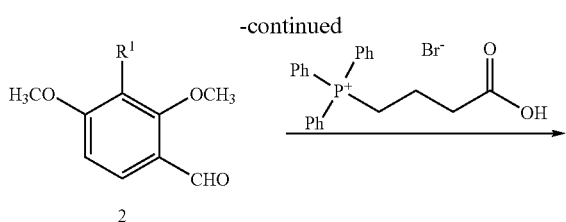

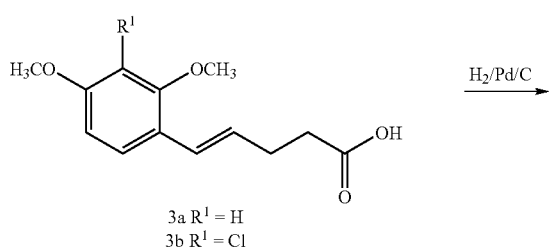

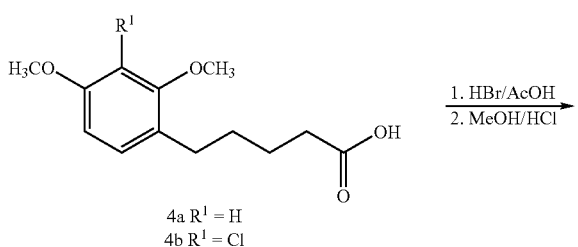

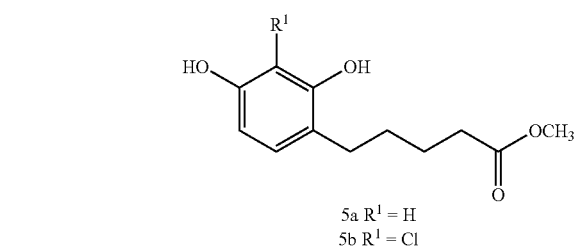

5-(3-substituted-2,4-dihydroxyphenyl)pentanoates 5 can be synthesized in 4 steps starting from 2-substituted-1,3-dimethoxybenzenes 1. Examples of 2-substituted-1,3-dimethoxybenzenes include, but are not limited to, 2-chloro-1,3-dimethoxybenzene (Kovacic, P. and Kurz, M. E. J. Org. Chem. 1966, 31: 2459-2467; Wada, M. et al. Bull. Chem. Soc. Jpn., 1992, 65(5): 1389-1391); 2-fluoro-1,3-dimethoxybenzene (W.-C. Sun et al. J. Org. Chem. 1997, 62: 6469-6475); and 2-phenyl-1,3-dimethoxybenzene (U.S. Pat. No. 6,221,604). Aldehydes 2 can be synthesized by formylation with α,α-dichloromethyl methyl ether in the presence of $TiCl_4$. These compounds can be converted into the pentenoic acids 3 by reaction with 3-carboxypropyltriphenylphosphoium bromide and lithium bis(trimethylsilyl)amide. Acids 4 can prepared by catalytic hydrogenation with 10% Pd/C. Deprotection of the methoxy groups using an acetic acid/aqueous hydrobromic acid mixture followed by esterification of the carboxy group (e.g. with methanol/HCl gas) can afford the desired 5-(3-substituted-2,4-dihydroxyphenyl)pentanoates 5.

The methyl 5-(3-substituted-2,4-dihydroxyphenyl)pentanoates 5 can be used in the synthesis of several compounds of the invention. The synthetic approaches herein are based on utilizing the methyl 5-(3-substituted-2,4-dihydroxyphenyl)pentanoates 5 in conjunction with known synthetic routes for dye assembly. The use of these intermediates is not limited to the classes described below, but finds broad application to any resorcinol-based dye chemistry.

Coumarin-Based Dye Synthesis

Resorcinol analogs 5 can be reacted with diketene to afford 8-substituted coumarins 6 (See Scheme 6). Hydrolysis of the ester group of 6 generates the free carboxylic acid 7. The carboxylic acid 7 can be converted into a variety of other ester groups by reaction with the corresponding alcohol in the presence of an acid. For example, PFP esters 8 can be made by reaction of 7 in the presence of pentafluorophenyl trifluoroacetate (PFP-TFA).

Scheme 6
Synthesis of 8-substituted coumarin-base dyes

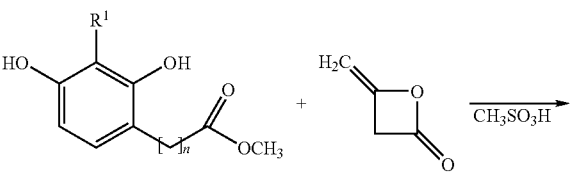

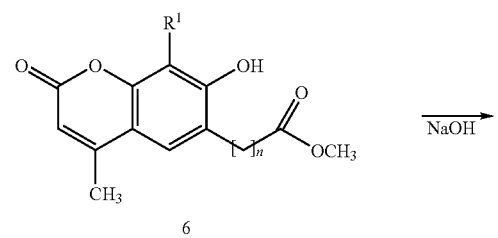

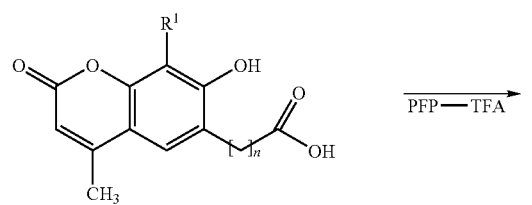

Phenoxazine (Resorufin)-Based Dye Synthesis

Phenoxazine-based compounds can be prepared as generally outlined in Scheme 3 and more specifically provided in Scheme 7, below.

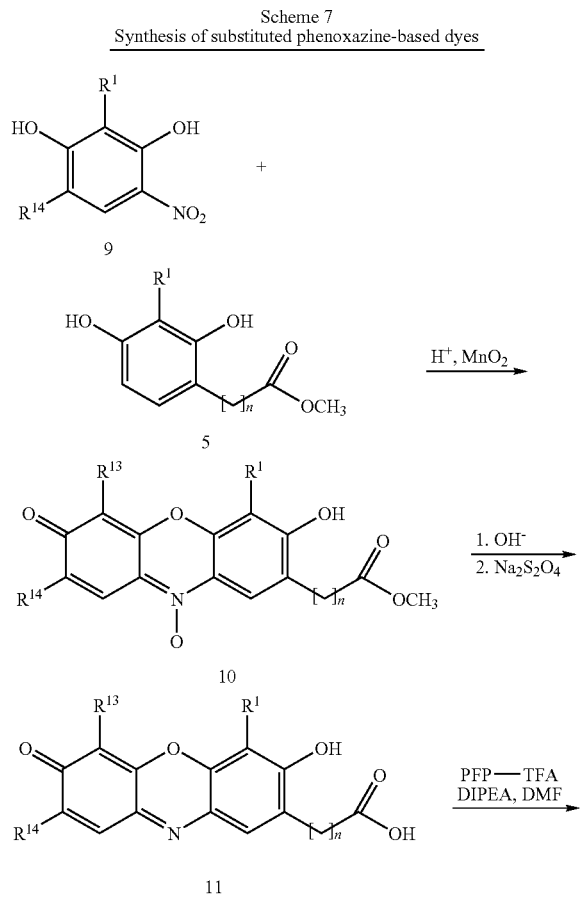

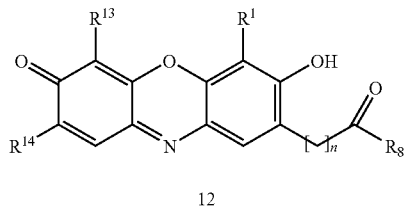

4-Nitrosorecorcinol derivatives 9 are commercially available or can be synthesized by methods commonly known in the art. Reaction of 4-nitrosorecorcinol derivative 9 with 5 in the presence of $MnO_2$ and an acid catalyst using methanol as a solvent can be used to prepare N-oxides 10. The ester of 10 can be hydrolyzed with NaOH followed by reduction of the N-oxide groups by a treatment with sodium diothionite to yield resorufin derivatives 11. Carboxylic acids 11 can be treated with an alcohol and an acid catalyst e.g. PFP/TFA to form ester derivatives 12 ($R^8$=heteroalkoxy, aryloxy, heteroaryloxy, and the like).

Xanthene-Based Lactone Synthesis

Synthesis of asymmetrical xanthene dyes (Scheme 8) can be accomplished in two steps. In the first step, benzophenones 14 may be prepared in good to excellent yields by Friedel-Crafts acylation of resorcinol analogs 5 with phthalic anhydrides 13 in the presence of a Lewis acid, such as $AlCl_3$. In the second step, ketones 14 were reacted with resorcinols 15 using methanesulfonic acid as a solvent. The esters 16 were saponified with NaOH followed by acidification to precipitate the acids 17. Subsequent conversion into an activated PFP ester 18 was achieved by treatment of acids 17 with PFP-TFA.

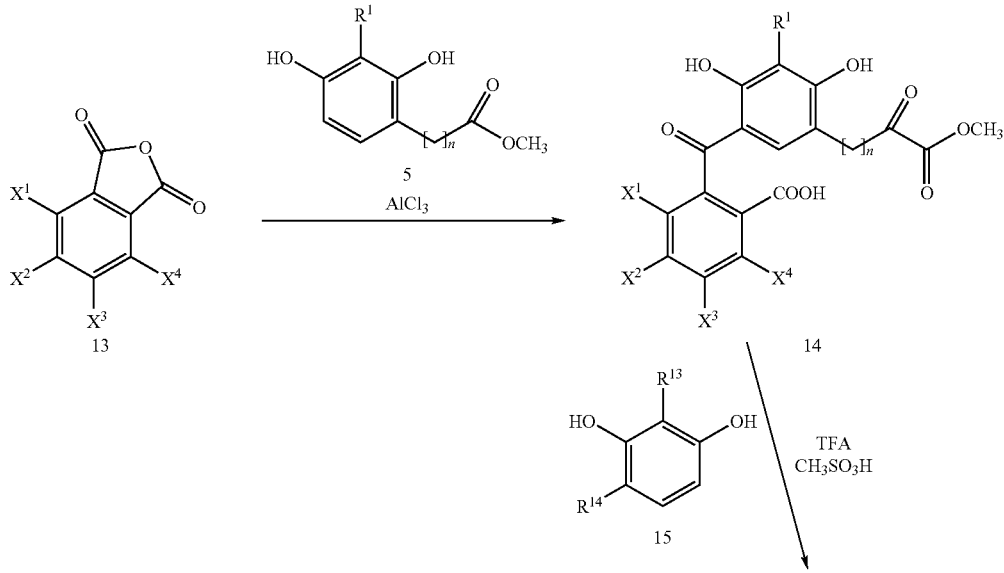

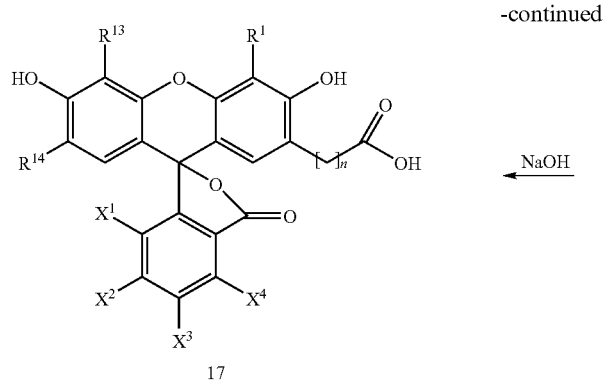

17

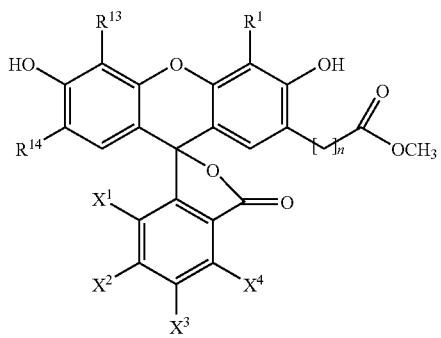

16

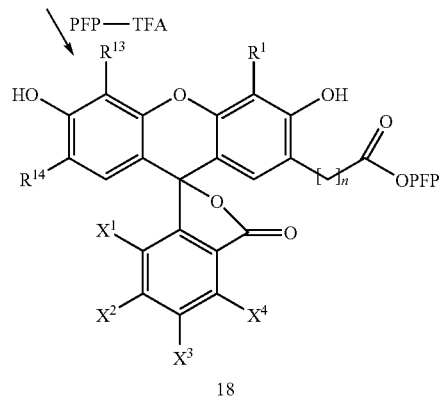

18

Benzo[a]- and benzo[c]xanthene-Containing Dye Synthesis

Benzo[a]- and benzo[c]xanthene dyes 19 (Scheme 9) and 23 (Scheme 10) can be synthesized by a method analogous to that used with xanthene dyes (Scheme 8). Thus condensation of benzophenones 14 either with 1,3- or 1,6-dihydroxynaphthalene yields esters 19. Esters 19 may be hydrolyzed to the corresponding acids 20 and then converted into the activated acid derivatives 21, such as the PFP ester ($R^8$=pentafluorophenoxy).

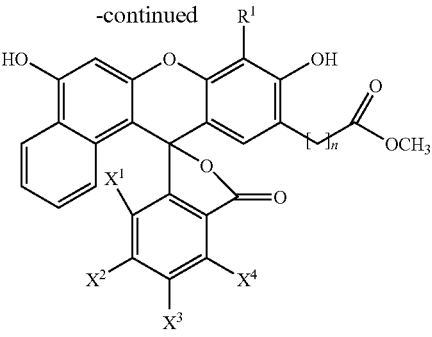

19

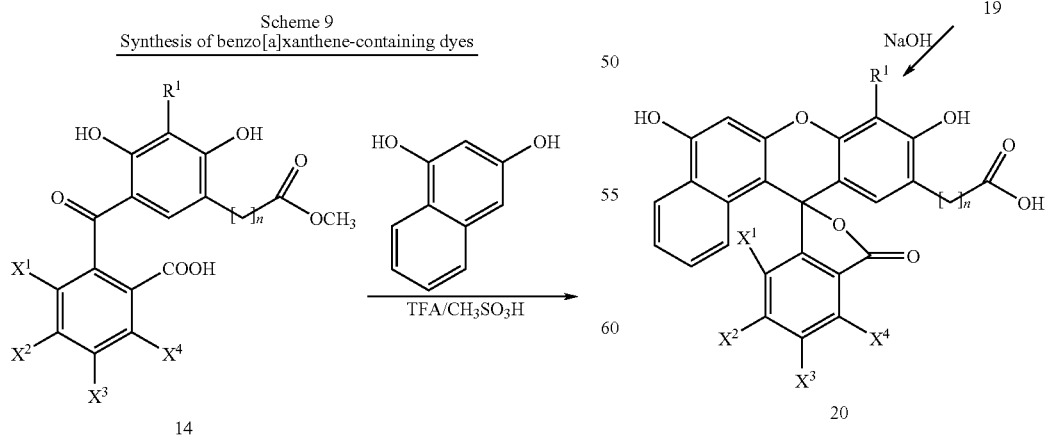

Scheme 9
Synthesis of benzo[a]xanthene-containing dyes

14

20

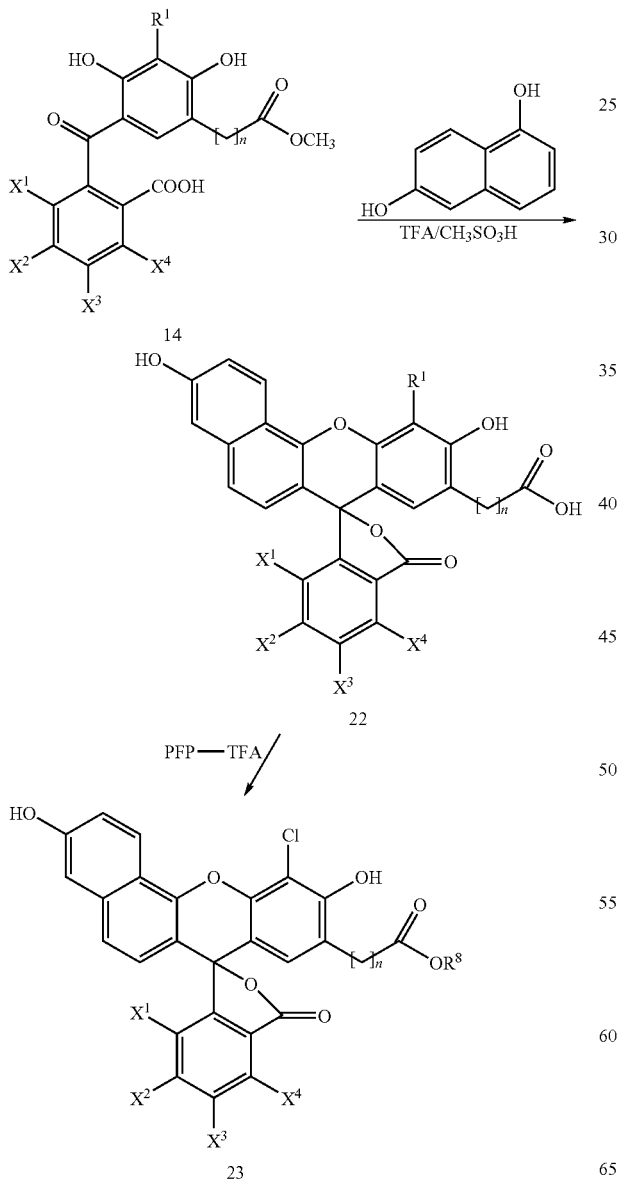

Scheme 10
Synthesis of benzo[c]xanthene-containing dyes

Other Reagents

The compounds provided above can be used to directly label biological materials or can be used to prepare a number of other dye reagents that are useful in the methods described herein, as well as other labeling processes.

Thus in another embodiment preferred compounds are where $R^8$ is $NR^9W(Y^2_pL)$. Within this embodiment $R^9$ is H, alkyl or combined with W to form a heterocycloalkylene, heterocycloalkylenearylene, or heterocycloalkyleneheteroarylene linking group; W is a linking group selected from the group consisting of a $(C_2-C_{50})$alkylene, heteroalkylene, $(C_2-C_{50})$cycloalkylene, heterocycloalkylene, $(C_6-C_{50})$ arylene group, a heteroarylene group, $(C_2-C_{50})$alkylene-arylene group, a heteroalkylenearylene group, optionally substituted with at least one substituent independently selected from the group consisting of $(C_1-C_8)$alkyl, hydroxy, protected hydroxyl, alkoxy, amino, protected amino, hydrazino, thio, protected thio and aryl; $Y^2$ is a cleavable linking group selected from the group consisting of:

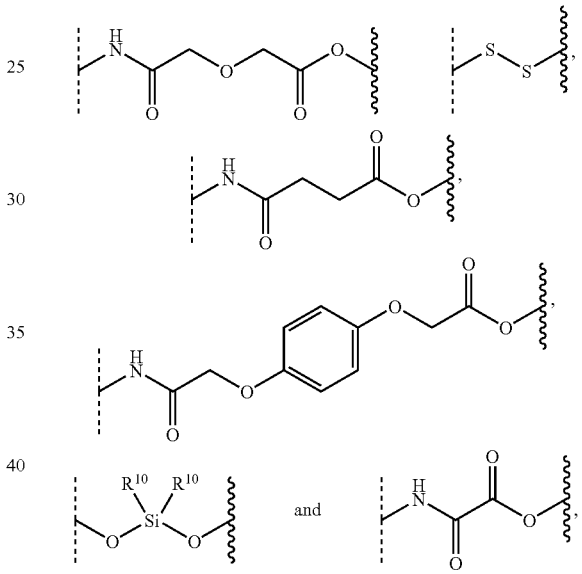

wherein dashed line indicates the point of attachment to L and the wavy line indicates the point of attachment to the rest of the molecule; each $R^{10}$ is independently $(C_1-C_8)$alkyl or $(C_1-C_8)$alkoxy. The subscript p may be an integer of from 0 to 1, each being equally preferred. L is solid support when p is 1 and L is a member selected from the group consisting of an O-phosphoramidite or a reactive functional group when p is 0; the subscript m is an integer of from about 0 to about 2; the subscript n is an integer of from about 3 to about 19. Compounds wherein n is 3, 4, 5, 6, 7, 8, 9, 10, 11, 12, 13, 14, 15, 16, 17, 18 and 19 are equally preferred. Preferably $R^9$ and W are combined together to form a linking group which comprises a prolinol component.

Scheme 11 below illustrates the reaction of compounds of the invention wherein $R^8$ is an activated carboxylic acid group (e.g. a PFP ester) with an amino-based nucleophilic ligand, such as a nucleic acid. Scheme 11 also illustrates the reaction of compounds of the invention with a linking group (e.g. a prolinol based linking group) that may be further elaborated to prepare phosphoramidite reagents or solid support-bound reagents.

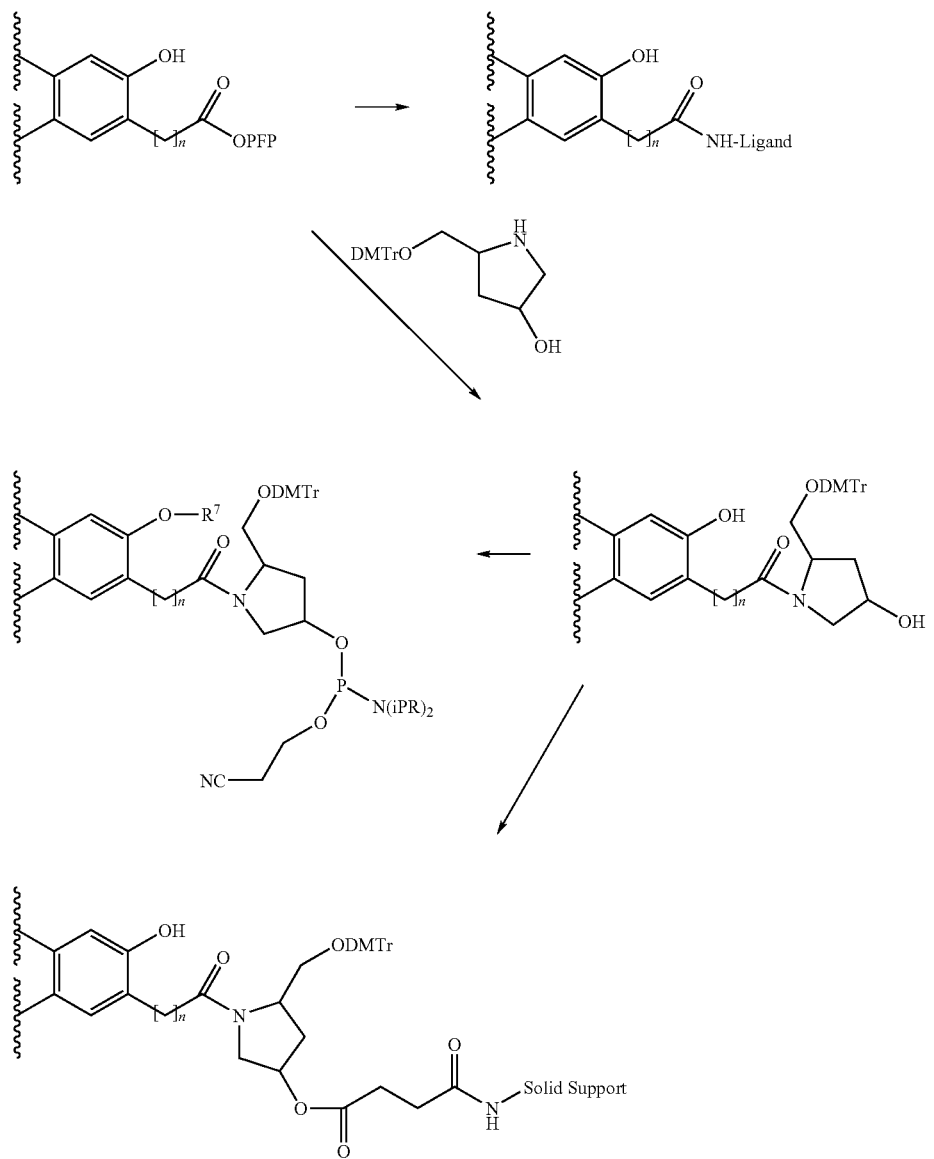

Scheme 11.

In preferred embodiments, the compounds are the preferred compounds as described herein. In other preferred embodiments, the linking group component comprises two reactive functional groups selected from amino, hydroxy, hydrazino and thiol, and is either linear, cyclic, or a combination thereof. Cyclic forms of the linking group include aromatic forms. Still further preferred are those embodiments in which the linking group comprises a $(C_2-C_{20})$alkylene or $(C_2-C_{20})$heteroalkylene group. In preferred embodiments, the linking group comprises a cyclic component, more preferably comprising a five-membered heterocyclic component, and even more preferably comprising a prolinol component.

In one group of preferred embodiments, p is 1, L is a solid support, and $Y^2$ is a cleavable linking group selected from the group consisting of:

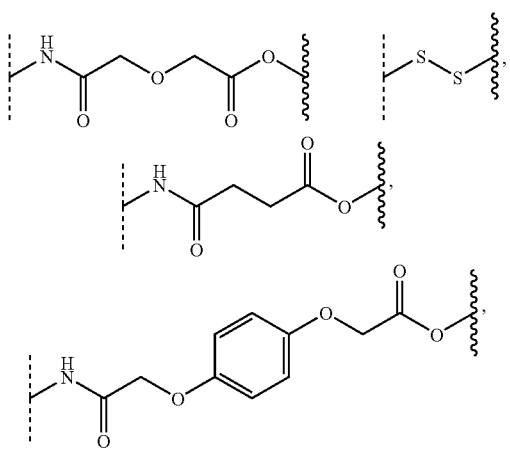

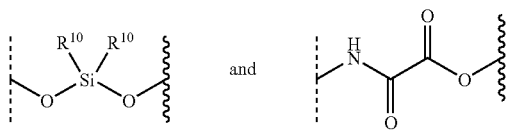

wherein dashed line indicates the point of attachment to L and the wavy line indicates the point of attachment to the rest of the molecule; and each $R^{10}$ is independently $(C_1-C_8)$alkyl or $(C_1-C_8)$alkoxy.

In another group of preferred embodiments, the dye reagents are xanthene dye reagents and are represented by the formula:

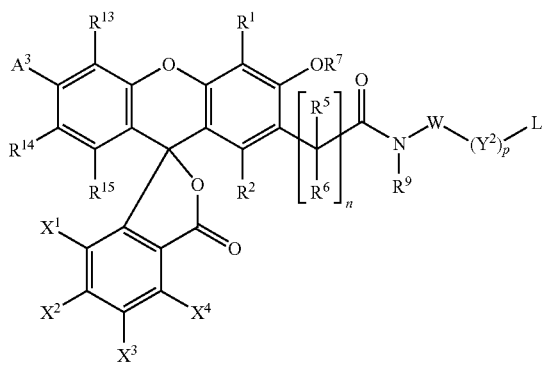

$A^3$ is a protected hydroxyl group; $R^{12}$ taken together with $R^{13}$ form a fused aromatic or heteroaromatic ring that is optionally substituted with from one to four substituents selected from halogen cyano, carboxy, sulfo, hydroxy, amino, mono $(C_1-C_6)$alkylamino, di$(C_1-C_6)$alkylamino, $(C_1-C_6)$alkyl, $(C_1-C_6)$alkylthio and $(C_1-C_6)$alkoxy; and tautomeric forms thereof; each $R^1$, $R^2$, $R^{13}$, $R^{14}$ and $R^{15}$ is independently selected from the group consisting of H, halogen, cyano, halo$(C_1-C_8)$alkyl, $(C_1-C_8)$alkyl, $(C_1-C_8)$alkylthio, $(C_1-C_8)$alkoxy, aryl and heteroaryl, or $R^{14}$ and $R^{15}$ is combined with the atoms which attach them to form a 5- or 6-membered aromatic ring; each $R^5$ and $R^6$ is independently selected from the group consisting of H, $(C_1-C_8)$alkyl, aryl, heteroaryl, aryl$(C_1-C_4)$alkyl and heteroaryl$(C_1-C_4)$alkyl; and optionally, each $R^7$ is H or a hydroxylprotecting group; and n is an integer from 4 to about 20.

In one embodiment, preferred compounds have the formula above wherein each $R^1$, $X^1$, $X^2$, $X^3$, $X^4$, $R^5$ and $R^6$ are H; and $R^{13}$ is methyl.

In another embodiment, preferred compounds have the formula above wherein each $R^1$, $X^2$ and $X^3$ is Cl; each $X^1$, $X^4$, $R^5$ and $R^6$ is H; and $R^{13}$ is methyl.

More generally, preferred phosphoramidite compounds have the formula selected from the group consisting of:

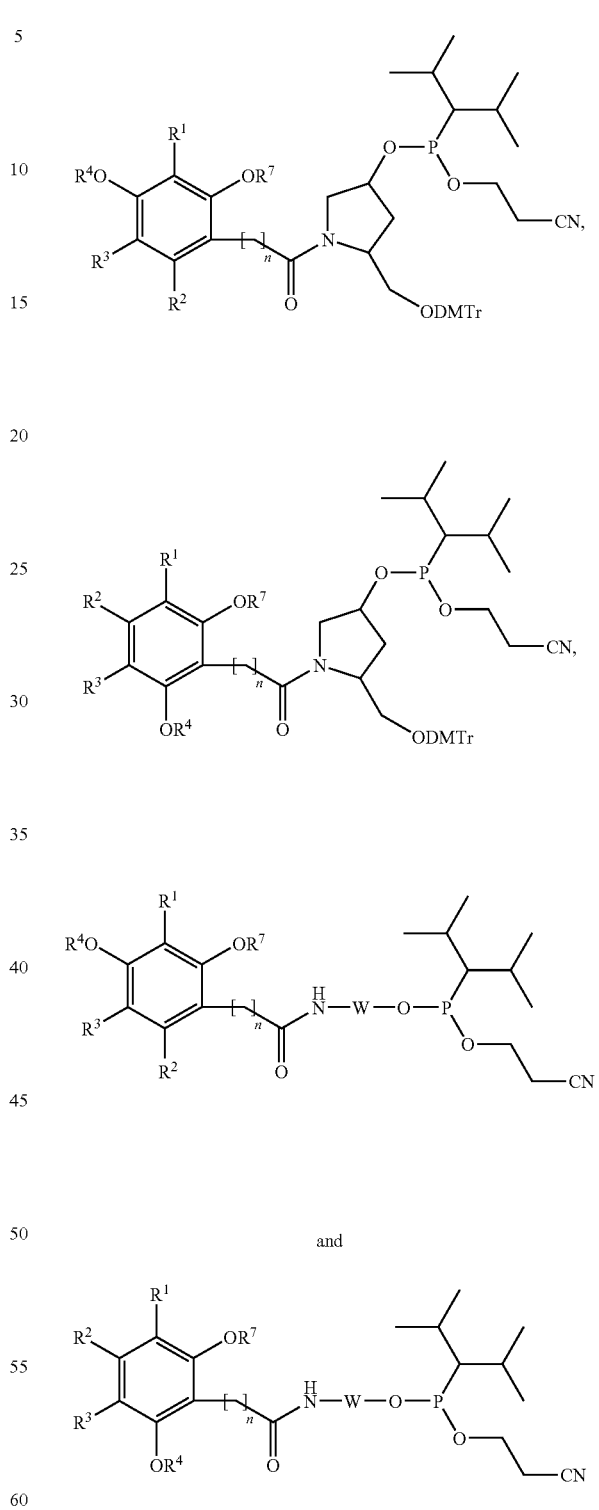

wherein $R^4$, $R^3$, $R^2$, $R^1$ and $R^7$ have the meanings provided above and W is a $(C_2-C_{12})$alkylene or $(C_5-C_{12})$heteroalkylene or $(C_8-C_{25})$ heteroalkylenearyl linking group.

Within the xanthene-based dye reagents, the dye reagents is most preferably one selected from the formula:
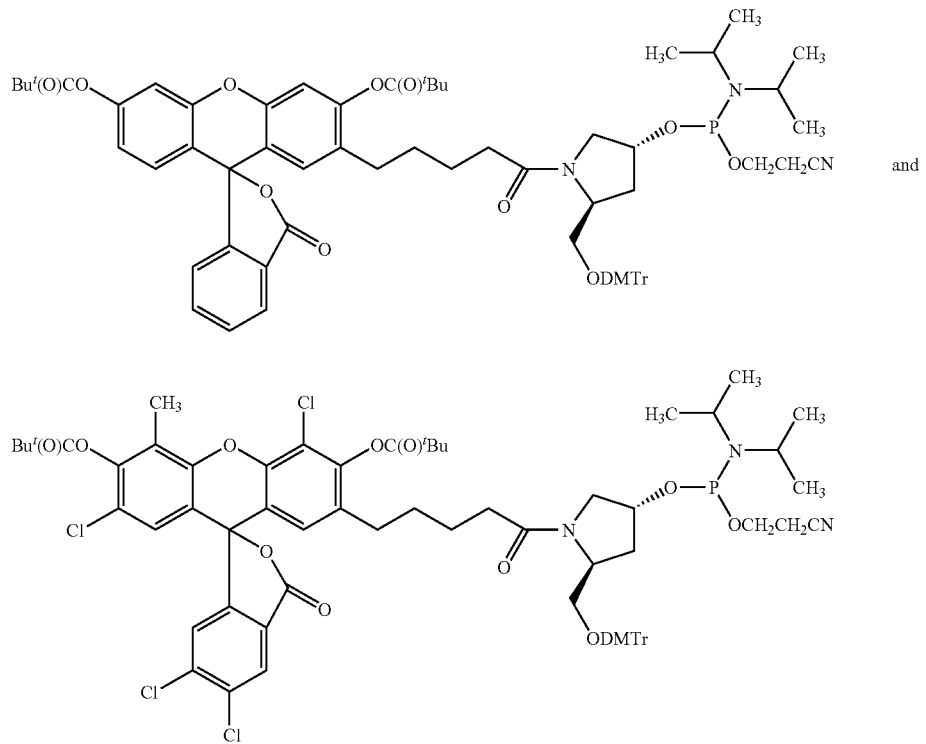
Within the xanthene-based dye reagents, the dye reagents is most preferably one selected from the formula:
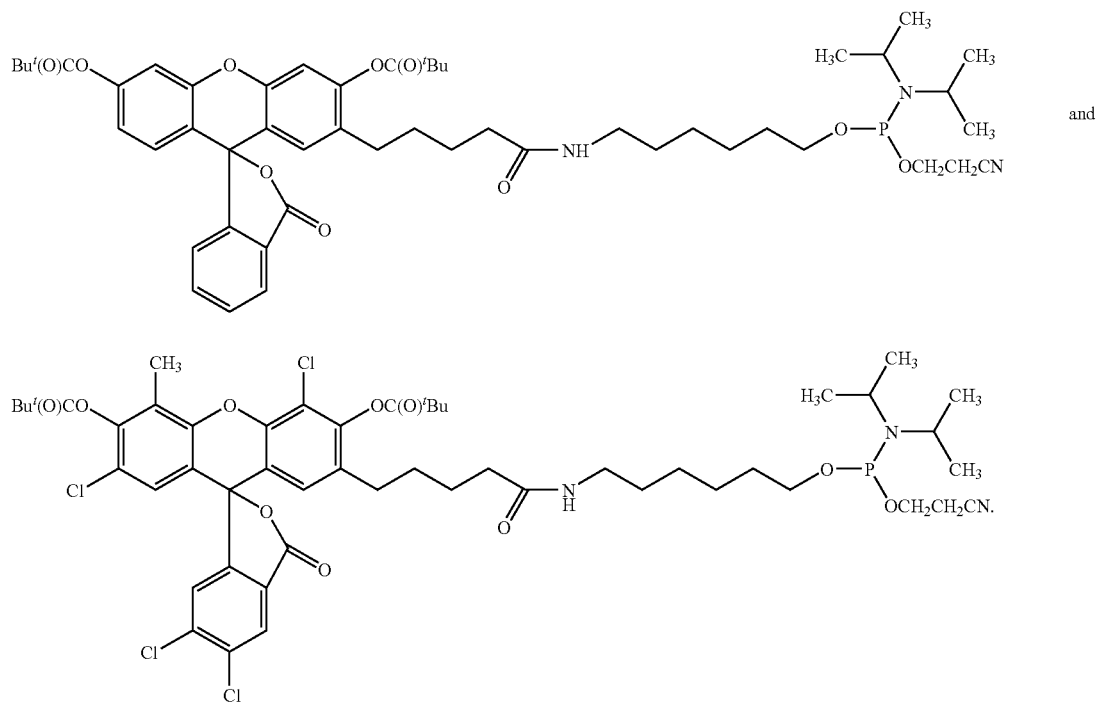

Still further preferred compounds are those prepared and described in detail herein and in any of Schemes 1 through 10.

Scheme 12 illustrates the preparation of a fluorescein-based phosphoramidite reagents of the above formula. One of skill in the art will appreciate that the dye componenet in compound 18 can be replaced by other dyes in the xanthene series (e.g., xanthene, benzo[a]xanthene, benzo[b]xanthene, benzo[c]xanthene) and the linking group (6-aminohexanol) can be substituted with other linear or cyclic linking groups as described herein and in the examples. Use of such substitutions provides access to the full scope of phosphoramidite reagents contemplated by the present invention.

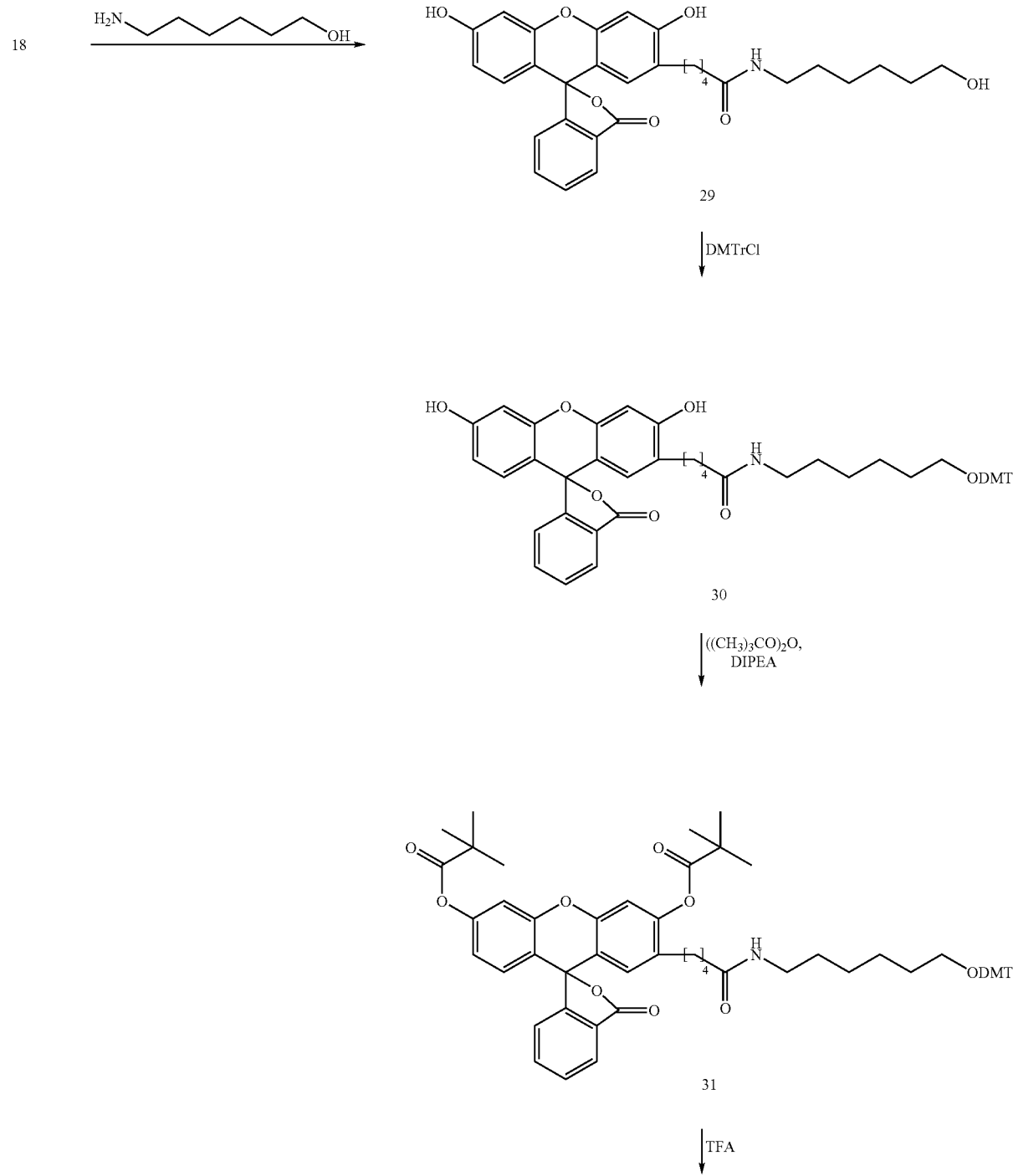

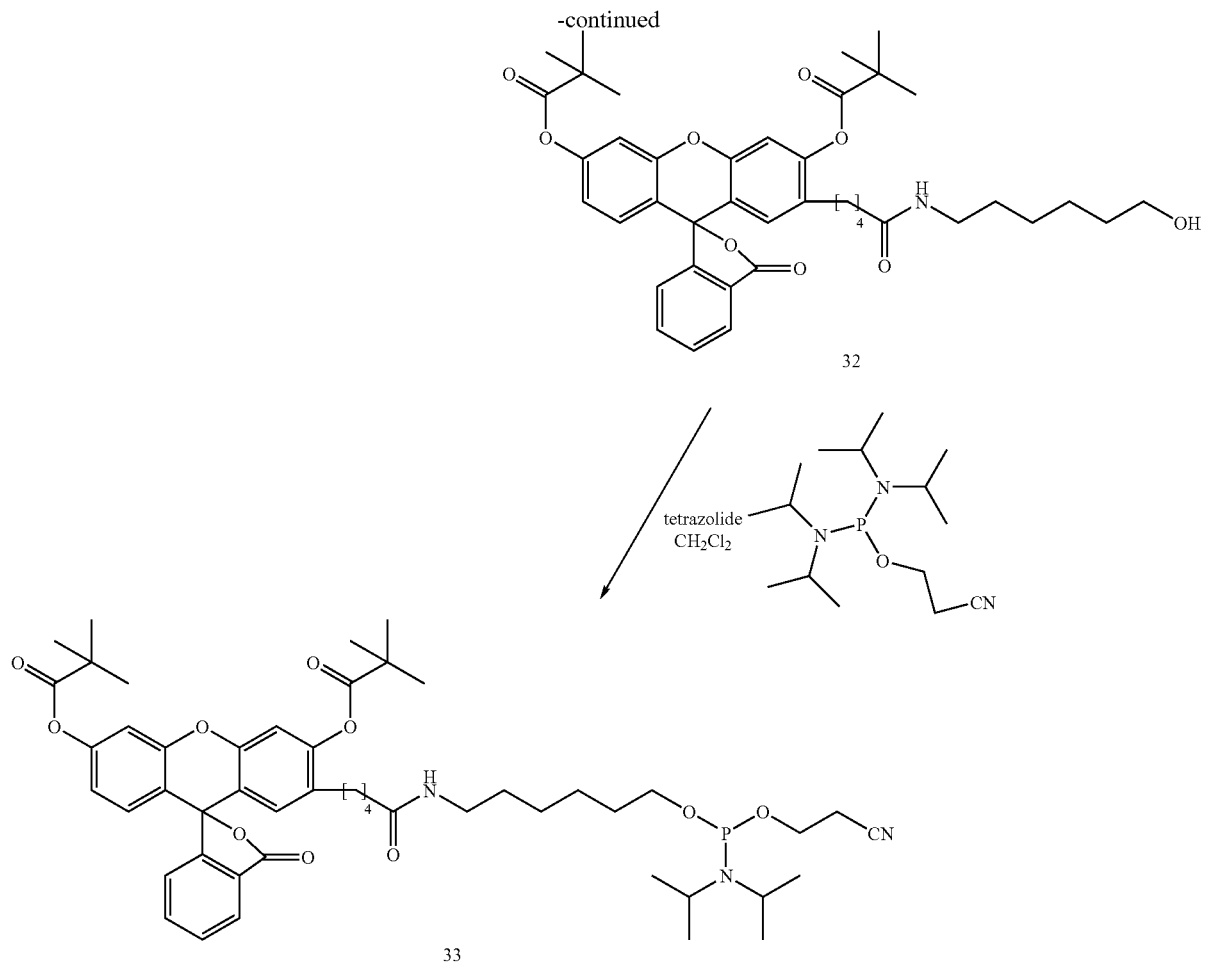

32

33

Thus, fluorescein-containing phosphoramidite 33 can be prepared by reaction of PFP ester 18 with 6-aminohexanol. The primary hydroxy group of 29 can be blocked with a transitory protecting group, such as a DMT group 30 to avoid a competitive reaction with trimethylacetic anhydride during the protection of phenol groups 31. The protecting group can be readily removed using standard conditions (e.g. for DMT, dilute trifluoroacetic acid solution in 10% methanol in dichloromethane). The resultant dipivaloyl intermediate 32 can be converted into phosphoramidite 33 using standard procedures.

In view of the above, the present invention further provides a method for preparing a compound having a formula selected from the group consisting of:

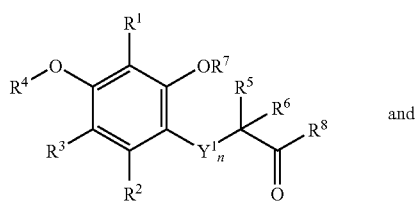

A and

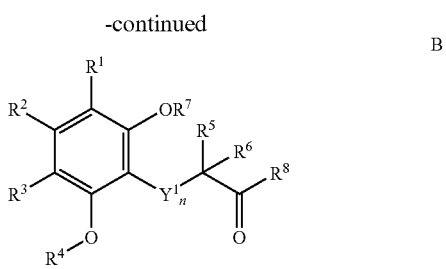

B wherein $Y^1$ is selected from the group consisting of $CR^5R^6$, $NR^5$, O, $P(O)_m$ and $S(O)_m$, wherein at least one $CR^5R^6$ is between each member selected from the group consisting of $NR^5$, O, $P(O)_m$ and $S(O)_m$; each $R^1$ or $R^2$ is a member independently selected from the group consisting of H, halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl; $R^3$ and $R^4$ are combined with the phenoxy moiety to which they are attached to form a ring system comprising from 2 to 5 rings, individually selected from the group consisting of five-membered rings, six-membered rings, and combinations thereof, wherein the rings are fused or spiro; optionally substituted with halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl, aryl($C_1$-$C_4$)alkyl and heteroaryl($C_1$-$C_4$)alkyl; wherein the alkyl portions of any of these substitutents are optionally substituted with halogen, carboxy, sulfo, amino, mono($C_1$-$C_6$)alkylamino, di($C_1$-$C_6$) alkylamino, ($C_1$-$C_6$)alkoxy, cyano, haloacetyl or hydroxy; and the aryl portions of any of these substitutents are optionally substituted with from one to four substituents selected from the group consisting of halogen, cyano, carboxy, sulfo, hydroxy, amino, mono($C_1$-$C_6$)alkylamino, di($C_1$-$C_6$)alkylamino, ($C_1$-$C_6$)alkyl, ($C_1$-$C_6$)alkylthio and ($C_1$-$C_6$)alkoxy; each $R^5$ or $R^6$ is a member independently selected from the group consisting of H, ($C_1$-$C_8$)alkyl, aryl, heteroaryl, aryl($C_1$-$C_4$)alkyl and heteroaryl($C_1$-$C_4$)alkyl; $R^7$ is H or a hydroxyl-protecting group; $R^8$ is $NR^9W(Y^2_pL)$; $R^9$ is H, alkyl or combined with W to form a heterocycloalkylene, heterocycloalkylenearylene, or heterocycloalkyleneheteroarylene linking group; W is a linking group selected from the group consisting of a ($C_2$-$C_{50}$)alkylene, heteroalkylene, ($C_2$-$C_{50}$)cycloalkylene, heterocycloalkylene, ($C_6$-$C_{50}$) arylene group, a heteroarylene group, ($C_2$-$C_{50}$)alkylenearylene group, a heteroalkylenearylene group, optionally substituted with substituents independently selected from the group consisting of ($C_1$-$C_8$)alkyl, hydroxy, protected hydroxy, alkoxy, amino, protected amino, hydrazino, thio, protected thio and aryl; $Y^2$ is a cleavable linking group selected from the group consisting of:

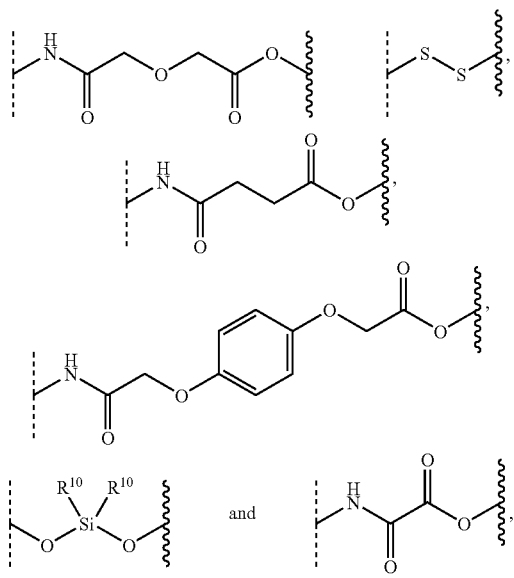

wherein dashed line indicates the point of attachment to L and the wavy line indicates the point of attachment to the rest of the molecule; each $R^{10}$ is independently ($C_1$-$C_8$)alkyl or ($C_1$-$C_8$)alkoxy; the subscript p is 0, L is solid support when p is 1 and L is a member selected from the group consisting of an O-phosphoramidite or a reactive functional group when p is 0; the subscript m is an integer of from about 0 to about 2; the subscript n is an integer of from about 3 to about 19; said method comprising contacting a compound of formula A or B wherein $R^8$ is a leaving group with a nucleophilic linking group component $HNR^9W(Y^2_pL)$. Compounds wherein n is 3, 4, 5, 6, 7, 8, 9, 10, 11, 12, 13, 14, 15, 16, 17, 18 and 19 are equally preferred.

The present invention further provides a method for preparing a compound having a formula selected from the group consisting of:

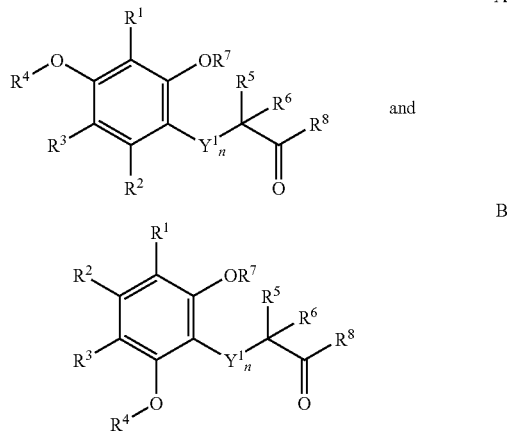

wherein $Y^1$ is selected from the group consisting of $CR^5R^6$, $NR^5$, O, $P(O)_m$ and $S(O)_m$, wherein at least one $CR^5R^6$ is between each member selected from the group consisting of $NR^5$, O, $P(O)_m$ and $S(O)_m$; each $R^1$ or $R^2$ is a member independently selected from the group consisting of H, halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl; $R^3$ and $R^4$ are combined with the phenoxy moiety to which they are attached to form a ring system comprising from 2 to 5 rings, individually selected from the group consisting of five-membered rings, six-membered rings, and combinations thereof, wherein the rings are fused or spiro; optionally substituted with halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl, aryl($C_1$-$C_4$)alkyl and heteroaryl($C_1$-$C_4$)alkyl; wherein the alkyl portions of any of these substitutents are optionally substituted with halogen, carboxy, sulfo, amino, mono($C_1$-$C_6$)alkylamino, di($C_1$-$C_6$) alkylamino, ($C_1$-$C_6$)alkoxy, cyano, haloacetyl or hydroxy; and the aryl portions of any of these substitutents are optionally substituted with from one to four substituents selected from the group consisting of halogen, cyano, carboxy, sulfo, hydroxy, amino, mono($C_1$-$C_6$)alkylamino, di($C_1$-$C_6$)alkylamino, ($C_1$-$C_6$)alkyl, ($C_1$-$C_6$)alkylthio and ($C_1$-$C_6$)alkoxy; each $R^5$ or $R^6$ is a member independently selected from the group consisting of H, ($C_1$-$C_8$)alkyl, aryl, heteroaryl, aryl($C_1$-$C_4$)alkyl and heteroaryl($C_1$-$C_4$)alkyl; $R^7$ is H or a hydroxyl-protecting group; $R^8$ is $NR^9W(Y^2_pL)$; $R^9$ is H, alkyl or combined with W to form a heterocycloalkylene, heterocycloalkylenearylene, or heterocycloalkyleneheteroarylene linking group; W is a linking group selected from the group consisting of a ($C_2$-$C_{50}$)alkylene, heteroalkylene, ($C_2$-$C_{50}$)cycloalkylene, heterocycloalkylene, ($C_6$-$C_{50}$) arylene group, a heteroarylene group, ($C_2$-$C_{50}$)alkylenearylene group, a heteroalkylenearylene group, optionally substituted with substituents independently selected from the group consisting of ($C_1$-$C_8$)alkyl, hydroxy, protected hydroxy, alkoxy, amino, protected amino, hydrazino, thio, protected thio and aryl; the subscript p is 0; L is an O-phosphoramidite; the subscript m is an integer of from about 0 to about 2; the subscript n is an integer of from about 3 to about 19; said method comprising contacting a compound of formula A or B wherein $R^8$ is $NR^9W(Y^2_pL)$, and L is a reactive functional group; with a phosphoramidite reagent under conditions sufficient to covalently attach a phosphoramidite moiety. Compounds wherein n is 3, 4, 5, 6, 7, 8, 9, 10, 11, 12, 13, 14, 15, 16, 17, 18 and 19 are equally preferred.

Synthetic Intermediates

Certain intermediates useful in preparing the compounds of the invention are also contemplated as part of the present invention. These intermediates have the formula:

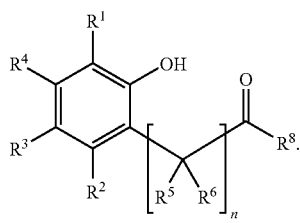

(XIV)

In these formula, each $R^1$, $R^2$, $R^3$ and $R^4$ is independently selected from the group selected from H, hydroxy, alkyloxy, aryloxy, alkyl, aryl, heterocyclyl, heteroaryl, sulfonyl, sulfamido, amino, amido, halogen, halo($C_1$-$C_6$)alkyl; and $R^5$ and $R^6$ are independently selected from the group selected from H, alkyl, aryl, cycloalkyl, and heterocyclyl; $R^8$ is a ($C_1$-$C_6$) alkyl or aryl ester group; with the proviso that at least one of $R^2$ or $R^4$ is hydroxy, and when $R^2$ is hydroxyl, at least one of $R^1$ or $R^3$ is H; and when $R^4$ is hydroxyl, $R^3$ is H.

In other preferred embodiments, $R^4$ is OH and $R^5$ and $R^6$ are H. In another preferred embodiment, $R^8$ is methoxy or ethoxy. In another preferred embodiment, $R^1$ is Cl, F or phenyl. In another preferred embodiment the compound is selected from the group consisting of:

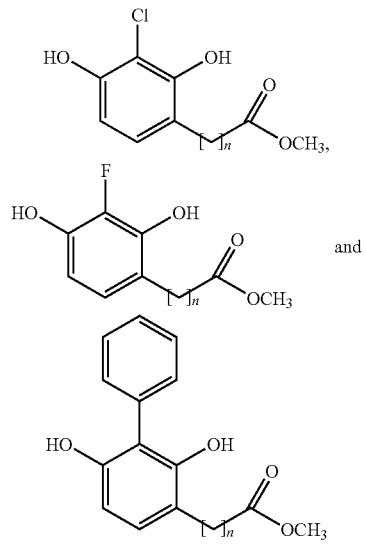

wherein the subscript n is an integer of from 4 to about 20. Compounds wherein n is 4, 5, 6, 7, 8, 9, 10,11,12,13, 14, 15, 16, 17, 18, 19 and 20 are equally preferred.

Methods for Labeling Biological Agents

In another embodiment, the present invention provides methods for preparing a labeled biological agent, the method comprising contacting an unlabeled biological agent with a compound of the invention under conditions sufficient to covalently attach said compound to said biological agent and form said labeled biological agent.

In a further aspect of the invention, the compounds of the invention are suitable for labeling biological agents or materials in, for example, automated synthesizers.

As shown in Scheme 13, the compounds of the invention can be reacted with a nucleic acid, e.g. the triethylammonium salt of an aminohexyl-modified ODN in an organic solvent, such as DMSO. Small molar excesses (about 2× to about 5×) of the compounds of the invention can lead to essentially quantitative (>90%) labeling of amine-containing ligands. The conjugates can be purified by gel-electrophoresis and/or reverse-phase HPLC. The absorbance and fluorescence spectra of the conjugates can be analyzed to confirm successful dye incorporation into the amine-containing ligand with the expected spectral characteristics.

Scheme 13
Derivatization of aminohexyl-octathymidylate with xanthene-based dyes

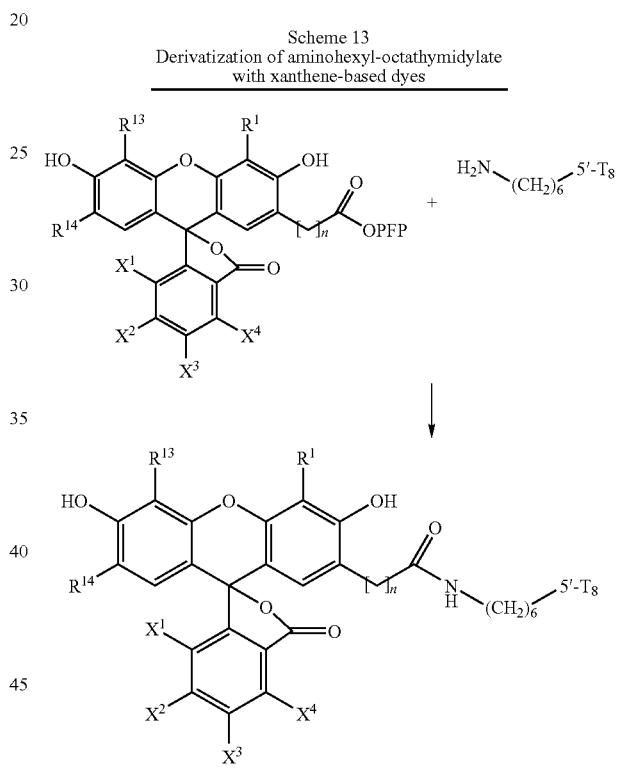

As noted above, the present invention finds broad application in labeling of biological agents. Examples of biological agents include, but are not limited to, nucleic acids (including, but not limited to, nucleotides, nucleosides, DNA, RNA, PNA, locked nucleic acids, oligonucleotides and the like), peptides or proteins, oligosaccharides, carbohydrates, glycosylated proteins, and other biological agents. Additionally, the nucleic acids can include modified compounds such as modified bases, for example 5-substituted pyrimidines, 3-substituted purines, substituted deazapurines, substituted pyrazolo[3,4-d]pyrimidines, universal bases, and the like (see e.g., co-pending U.S. application Ser. Nos. 09/724,988 and 09/447,936). The invention also includes methods of labeling oligonucleotides and modified oligonucleotides having attached groups such as minor groove binders, intercalators, crosslinking groups, and the like.

Labeled Modified Bases

In another embodiment, the present invention further provides modified nucleotide bases and oligonucleotides that are labeled using the compounds described above. A variety of modified bases can be used and are known to those of skill in the art. Essentially, any nucleotide base having an appended reactive functional group can be used, as well as nucleotide analogs (e.g., pyrimidines, purines, pyrazolopyrimidines, deazapurines, and the like). Without intending any limitation on this aspect of the invention, Scheme 14 illustrates the reaction of a compound of the invention with each of two modified nucleotide bases. These reactions are readily adapted for all compounds described herein.

Examples of the reaction of a compound of the invention with amine ligands are also exemplified by Scheme 14. Thus, 3-substituted pyrazolo[3,4,d]pyrimidines or 5-substituted pyrimidines containing an amino group can be converted to related phophoramidite reagents. In this Scheme, $R^8$ represents an activated carboxylic acid, for example a PFP ester; and the subscript n is an integer of about 4 to about 20.

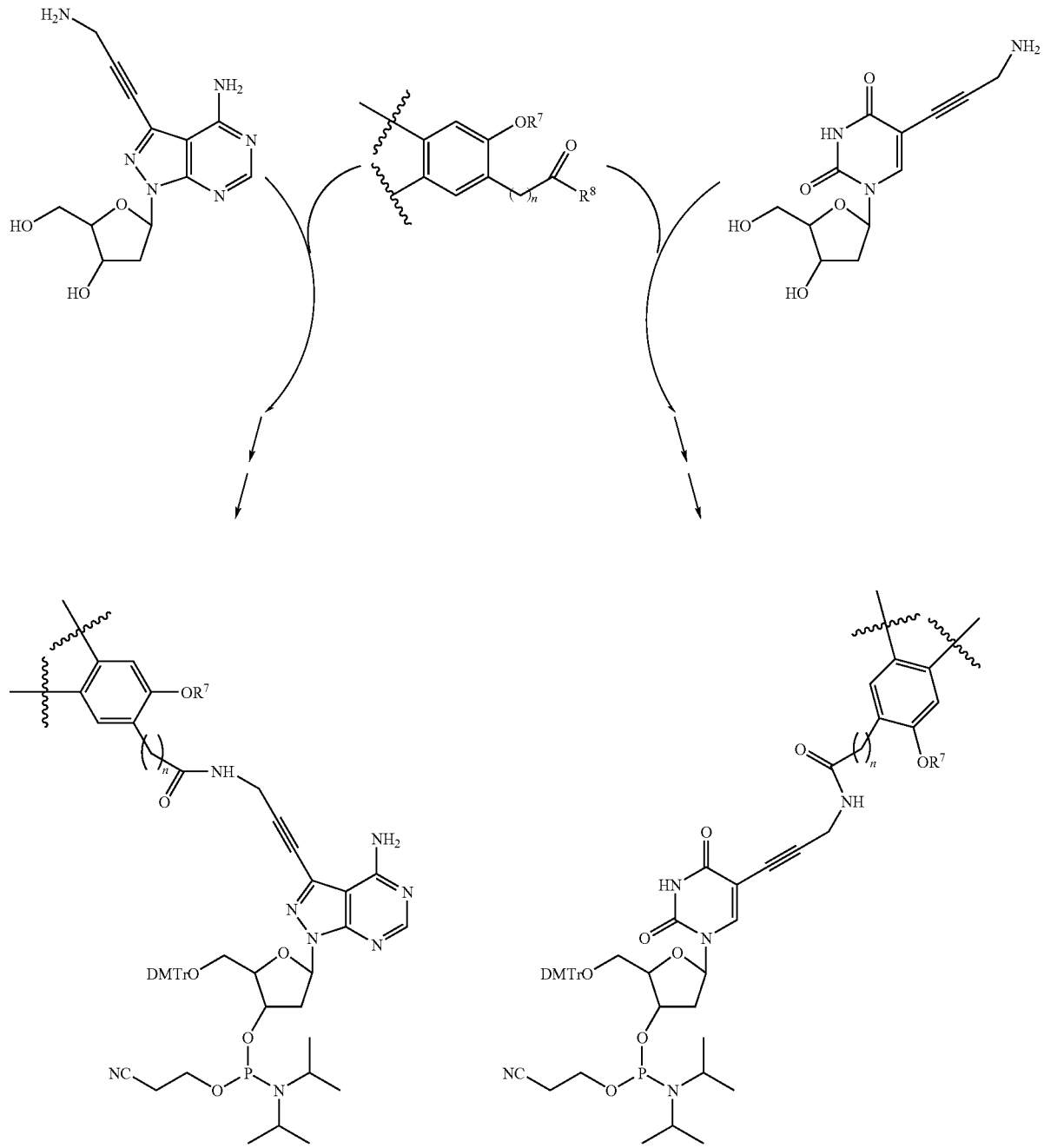

Scheme 14

Compounds wherein n is 4, 5, 6, 7, 8, 9, 10, 11, 12, 13, 14, 15, 16, 17, 18, 19 and 20 are equally preferred.

Thus, in another embodiment the present invention also provides a biological agent selected from the group consisting of nucleic acids, carbohydrates, peptides and combinations thereof covalently modified with a substituent having the formula selected from the group consisting of:

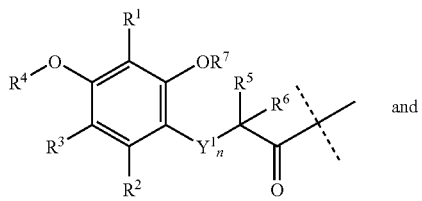

and

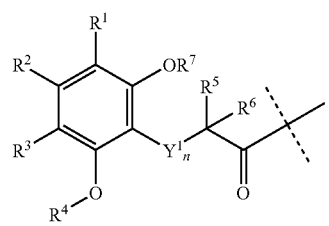

wherein $Y^1$ is selected from the group consisting of $CR^5R^6$, $NR^5$, O, $P(O)_m$ and $S(O)_m$, wherein at least one $CR^5R^6$ is between each member selected from the group consisting of $NR^5$, O, $P(O)_m$ and $S(O)_m$; each $R^1$ or $R^2$ is a member independently selected from the group consisting of H, halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl; $R^3$ and $R^4$ are combined with the phenoxy moiety to which they are attached to form a ring system comprising from 2 to 5 rings, individually selected from the group consisting of five-membered rings, six-membered rings, and combinations thereof, wherein the rings are fused or spiro; optionally substituted with halogen, cyano, halo($C_1$-$C_8$)alkyl, ($C_1$-$C_8$)alkyl, ($C_1$-$C_8$)alkylthio, ($C_1$-$C_8$)alkoxy, aryl and heteroaryl, aryl($C_1$-$C_4$)alkyl and heteroaryl($C_1$-$C_4$)alkyl; each $R^5$ or $R^6$ is a member independently selected from the group consisting of H, ($C_1$-$C_8$)alkyl, aryl, heteroaryl, aryl($C_1$-$C_4$)alkyl and heteroaryl($C_1$-$C_4$)alkyl; $R^7$ is H or a hydroxylprotecting group; the subscript m is an integer of from about 0 to about 2; the subscript n is an integer of from about 4 to about 20; and the dashed line indicates the point of attachment to said biological agent or said linking group joining said biological agent to said substituent. Compounds wherein n is 4, 5, 6, 7, 8, 9, 10, 11, 12, 13, 14, 15, 16, 17, 18, 19 and 20 are equally preferred.

In one preferred embodiment, the biological agent is nucleic acid. In another preferred embodiment the substituent on the nucleic acid has the formula selected from the group consisting of:

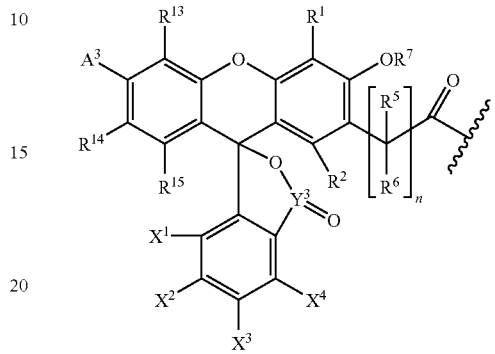

and

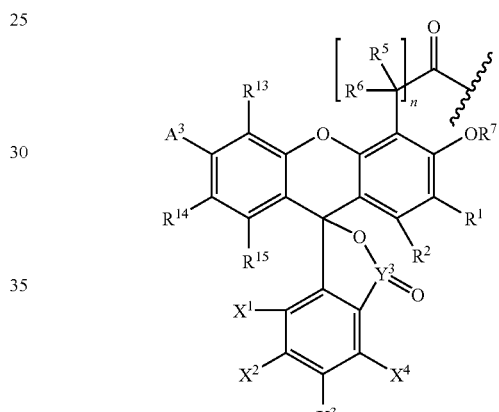

wherein, $A^3$ is OH; $R^7$ is H or a hydroxylprotecting group; each $R^1$, $R^2$, $R^{13}$, $R^{14}$ and $R^{15}$ is a member independently selected from the group consisting of H, halogen, cyano, halo($C_1$-$C_8$)alkyl, ($C_1$-$C_8$)alkyl, ($C_1$-$C_8$)alkylthio, ($C_1$-$C_8$) alkoxy, aryl and heteroaryl; or $R^{14}$ and $R^{15}$ is combined with the atoms which attach them to form a 5- or 6-membered aromatic ring; and the wavy line indicates the point of attachment to said nucleic acid or said linking group joining said nucleic acid to said substituent. In another preferred embodiment, the nucleic acid comprises an attached quencher, an attached minor groove binder, or a combination thereof. In one embodiment the substituent is preferably attached at the 3'-end of said nucleic acid and said quencher and said minor groove binder are attached at the 5'-end of said nucleic acid. In another embodiment the substituent is preferably attached at the 5'-end of said nucleic acid and said quencher and said minor groove binder are attached at the 3'-end of said nucleic acid.

The invention is further illustrated by the following examples.

EXAMPLES

(4E)-5-(2,4-Dimethoxyphenyl)pent-4-enoic Acid (3a)

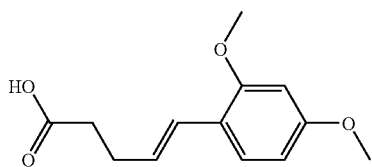

An oven-dried 2 L 3-neck flask was secured over a dry ice/isopropanol bath and magnetic stirring plate, fitted with an oven-dried 500 ml dropping funnel, a magnetic stir bar, an argon inlet, and a thermometer. The flask was flushed with argon, charged with 71.3 grams (166 mmol) of 3-carboxypropyltriphenylphosphonium bromide followed by 400 ml of THF, and closed. An argon balloon was used to cap the addition funnel and the reaction mixture was stirred for a half hour while cooling. A mixture of 63.9 grams (381.8 mmol) of lithium bis (trimethylsilyl) amide in 400 ml of THF was added to the reaction mixture via an addition funnel, with stirring, after the temperature had gone below −50° C. and at such a rate as to keep the temperature at or below −40° C. When the addition was complete, the dry ice bath was carefully removed and replaced with a ice/salt (NaCl) bath to maintain a reaction temperature about −10 to −20° C. The reaction mixture was stirred for about 2 hours to give a clear orange mixture. The temperature was reduced to −40° C. with a dry ice bath and a solution of 27.6 grams (166 mmol) of dimethoxybenzaldehyde in about 320 ml of THF was added to the reaction mixture over a half hour via an addition funnel. The temperature was held at −18 to −20° C. with the ice/salt bath for two hours, then the flask was allowed to warm to room temperature. The reaction mixture was allowed to warm overnight, then transferred to a 3 L evaporation flask, and the solvents were evaporated. The by-product, triphenylphosphene oxide, and any remaining starting material was removed by extraction with a 1:1 mixture of ethyl acetate/water (1.4 L) and washing with saturated sodium bicarbonate (300 ml). The combined aqueous layers were washed with 600 ml of ether to remove residual triphenylphosphene oxide, and acidified with 10% citric acid solution until the pH of the mixture was around 2-3. This mixture, which contained some solids, was extracted with ethyl acetate (2×300 ml). The combined extracts were dried and evaporated in vacuo. The yield was 36.2 grams of solid product (>98%). $^1$H NMR (DMSO-d$_6$) δ: 12.09 (s, 1H), 7.29 (d, J=8.2 Hz, 1H), 6.49 (m, 3H), 6.06 (m, 1H), 3.76 (s, 3H), 3.74 (s, 3H), 2.34 (br s, 4H).

(4E/Z)-5-(3-Chloro-2,4-dimethoxyphenyl)pent-4-enoic Acid (3b)

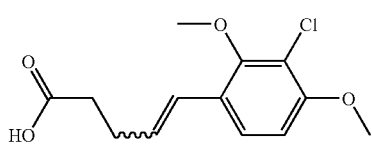

A 3 L 3-neck flask was charged with 3-carboxypropyltriphenylphosphonium bromide (25.4 g, 59.17 mmol) and THF (150 ml) and a magnetic stir bar and closed. The flask was cooled with a mixture of dry ice/isopropanol. A mixture of lithium bis(trimethylsilyl)amide (22.77 g, 136.1 mmol) in THF (150 ml) was added to the reaction mixture, with good stirring, via addition funnel, after the temperature had gone below −50° C. and at such a rate as to keep the temperature at or below 40° C. When the addition was complete, the dry ice bath was carefully removed and another bath that would produce a temperature of about −20° C. (mixture of ice and NaCl) was set in its place. The temperature was kept below about −10° C. and the reaction was stirred for about 2 hours to give a clear orange solution. Then the temperature was reduced to −20° C., while a solution of (11.87 g, 59.17 mmol) of 2,4-dimethoxy-3-chlorobenzaldehyde (2b) (Plattner, J. J. et al. *J. Med. Chem.*, 27(8): 1016-1026 (1984)) in 120 to 150 ml of THF was made and added to the addition funnel. This solution was added to the flask over a half hour, with stirring, while holding the temperature around −18 to −20° C. for at least two hours, then the flask was allowed to warm to room temperate. The solvents were evaporated and residue partitioned between 400 ml of ethyl acetate and 400 ml of water. After agitation and phase separation, the aqueous layer was collected, while the organic layer was washed with additional 300 ml of saturated sodium bicarbonate twice and discarded. The combined aqueous layers were washed with ether to remove residual triphenylphosphine oxide, and acidified with 10% citric acid until the pH of the mixture was around 3 to 4. This mixture was extracted with ethyl acetate (250 ml×2) and the combined extracts were dried and evaporated in vacuo. The yield was 15.0 g (93.6%) of 3b as a mixture of cis-(25%) and trans-(75%) isomers. $^1$H NMR (DMSO-d$_6$) δ: 12.12 (s, 1H), 7.43 (d, J=8.8 Hz, 1H), 7.24 (d, J=8.8 Hz, 1H), 6.93 (m, 1H), 6.6-6.4 (m, 1H), 6.22 (m, 1H), 5.69 (m, 1H), 3.86 (s, 1H), 3.84 (s, 3H), 3.70 (s, 3H), 3.68 (s, 1H), 2.41 (m, 4H).

5-(3-Chloro-2,4-dimethoxyphenyl)pentanoic Acid (4b)

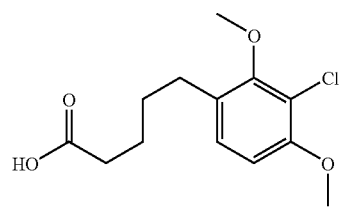

A solution of 3b (15.0 g, 55.4 mmol) in acetic acid (220 ml) was hydrogenated at 40-50 psi in the presence of 2.2 g of 10% Pd/C. The reaction was continued until no more hydrogen was being consumed (about 4 h). The catalyst was removed by filtration of the solution through Celite. The Celite was washed with some additional acetic acid. Evaporation of the solvent afforded 14.3 g (94.6%) of the desired product. $^1$H NMR (DMSO-d$_6$) δ: 12.0 (br s, 1H), 7.12 (d, J=8.6 Hz, 1H), 6.87 (d, J=8.6 Hz, 1H), 3.82 (s, 3H), 3.73 (s, 3H), 2.55 (t, 2H), 2.23 (t, 2H), 1.51 (m, 4H).

Methyl 5-(3-chloro-2,4-dihydroxyphenyl)pentanoate (5b)

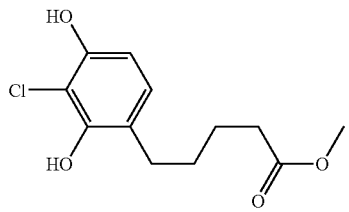

A 1 liter, 3 neck, round-bottomed flask equipped with a reflux condenser was charged with 4b (14.3 g, 52.4 mmols). Acetic acid (120 ml) and 48% hydrobromic acid (94 ml) were added. The mixture was refluxed with stirring for 15 to 16 h and cooled. The solvent was evaporated on a rotary evaporator. The residue was dissolved in methanol (100 ml) and anhydrous hydrogen chloride (HCl) was bubbled for about 10 minutes. The warm solution was cooled and evaporated. The resulting syrup was dissolved in ethyl acetate (150 ml) and extracted with water, saturated sodium bicarbonate (2×100 ml), saturated sodium chloride, and dried over sodium sulfate. Evaporation of the solvent and drying under vacuum afforded a viscous syrup. The crude material was chromatographed on silica (2:1 hexanes/ethyl acetate) and the pure product fractions concentrated to afford 8.6 g (63%) of the desired substituted resorcinol analog 5b as a pale tan-colored, viscous oil. $^1$H NMR (DMSO-$d_6$) δ: 9.70 (s, 1H), 8.77 (s, 1H), 6.79 (d, J=8.3 Hz, 1H), 6.39 (d, J=8.3 Hz, 1H), 3.57 (s, 3H), 2.47 (t, J=6.5 Hz, 2H), 2.23 (t, J=6.9 Hz, 2H), 1.49 (m, 4H).

4,5-Dichloro-2-({3-chloro-2,4-dihydroxy-5-[4-(methoxycarbonyl)butyl]phenyl}carbonyl)benzoic Acid (14b)

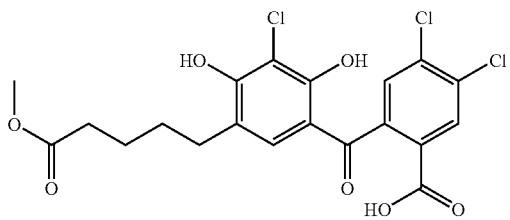

In a 2 L 3-neck round-bottomed flask equipped with a stir and addition funnel was added 4,5-dichlorophthalic anhydride (7.13 g, 32.9 mmol) followed by dry 1,2-dichloroethane (120 ml). After stirring for 30 minutes AlCl$_3$ (11.4 g, 85.54 mmol) was added and the mixture was stirred for another 30 minutes. To this mixture was added via the addition funnel a solution of 5b (8.5 g, 32.9 mmol) with stirring. The solution in the flask became slightly warm and turned dark. Hydrogen chloride gas evolved for about 10 to 20 minutes. Stirring was continued overnight (15-18 hours) at room temperature. During this time, a tarry precipitate formed. To this mixture was added ice (160 g) and concentrated HCl (80 ml) followed by ethyl acetate (900 ml). The content of the flask was stirred until all the solids have completely dissolved. The mixture was transferred to a 2-liter separatory funnel. The organic layer was washed with about 300 ml of 1 N HCl, 2×200 ml of saturated NaCl and dried over sodium sulfate. The solution was filtered and evaporated to a solid, which was then triturated in 200 ml of dichloromethane for 30 minutes, and then cooled to −20° C. for at about 2 h. The crystalline precipitate was filtered off and washed with 2:1 hexanes/dichloromethane, followed by 4:1 hexanes/dichloromethane, and dried to afford 10.8 g (69%) of the desired benzophenone 14b. $^1$H NMR (DMSO-$d_6$) δ: 12.44 (s, 1H), 10.3 (br s, 1H), 8.14 (s, 1H), 7.87 (s, 1H), 6.88 (s, 1H), 3.55 (s, 3H), 2.44 (t, J=6.8 Hz, 2H), 2.25 (t, J=6.9 Hz, 2H), 1.40 (m, 4H).

4-Chloro-2-methylbenzene-1,3-diol (15b)

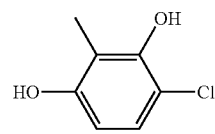

To a solution of 2-methylresorcinol (40 g, 322 mmol) in 750 ml of methanol was added (45.17 g, 0.338 mol) of N-chlorosuccinimide. The mixture was stirred for 6 hours. The solvent was evaporated and the resulting solid was triturated in 500 ml of a 2:1 mixture of hexane and ethyl acetate. The brown crystalline precipitate (succinimide) was filtered off and rinsed with a little extra solvent. The filtrate was concentrated to give the crude product, which was further purified on silica eluting with 4:1 hexanes/ethyl acetate. Appropriate fractions were combined, and evaporated. The product was crystallized from about 1:8 ether/hexanes to afford 33.1 g (65%) of the desired substituted resorcinol 15b. $^1$H NMR (DMSO-$d_6$) δ: 9.38 (s, 1H), 8.83 (s, 1H), 6.92 (d, J=8.5 Hz, 1H), 6.33 (d, J=8.5 Hz, 1H), 2.00 (s, 3H).

5-(5,6,13,16-Tetrachloro-12,15-dihydroxy-14-methyl-1-oxospiro[3-hydroisobenzofuran-3,9'-xanthene]-11-yl)pentanoic Acid (17b)

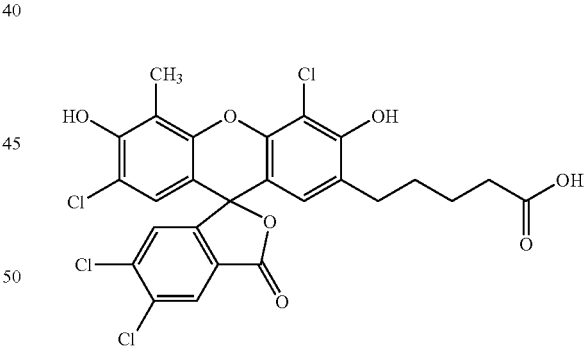

To a cold (0° C., ice/water bath) solution of 2 g (4.2 mmol) of benzophenone 14b and 1.0 g (6.3 mmol) of 4-chloro-2-methyl resorcinol (15b) in 31.7 ml of trifluoroacetic acid was slowly added 12.7 ml (196.1 mmol) of methanesulfonic acid using addition funnel. After being stirred at 0° C. for 20 hours, 300 g of ice was added into the reaction flask. A yellow precipitate formed. The mixture was stirred for about 20 minutes, and then filtered, using a sintered glass medium porosity funnel. The precipitate was washed with water several times, using a volume of about 50 to 100 ml each. The wet material was transferred into a 500 ml Erlenmeyer flask, suspended in 300 ml and treated with 10 ml of triethylamine. This resultant dark solution was heated to 70° C., stirred at this temperature for 20 min, and allowed to slowly cool to room temperature. When the mixture was cool, it was acidified with concentrated HCl to pH 2. The precipitated material was collected by filtration and resuspended in 200 ml of 0.2 N sodium hydroxide. After being heated at 60° C. for 20 minutes the solution was acidified with 1N HCl to pH 2-3. The resulting precipitate was filtered off and washed with water several times and dried. The crude product (about 80% pure) was chromatographed on silica eluting with 99% (1:1 ethyl acetate/hexanes) 1% acetic acid. Appropriate fractions were collected, concentrated and dried in vacuo to afford 1.66 g (68%) of the desired dye acid as an orange solid. $^1$H NMR (DMSO-d$_6$) δ: 11.87 (br s, 1H), 9.96 (s, 2H), 8.27 (s, 1H), 7.83 (s, 1H), 6.81 (s, 1H), 6.58 (s, 1H), 2.44 (t, 2H), 2.38 (s, 3H), 2.14 (t, J=6.1 Hz, 2H), 1.39 (m, 4H).

2,3,4,5,6-Pentafluorophenyl 5-(5,6,13,16-tetrachloro-12,15-dihydroxy-14-methyl-1-oxospiro[3-hydroisobenzofuran-3,9'-xanthene]-11-yl)pentanoate (18b)

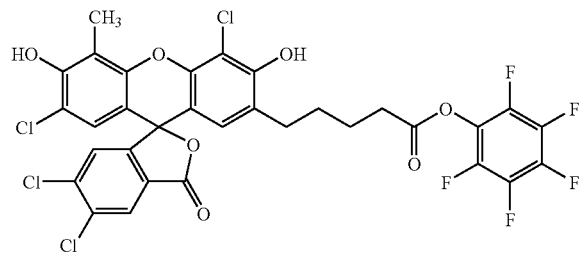

To a solution of 100 mg (0.170 mmol) of acid 17b and 0.074 ml (0.425 mmol) of diisopropylethylamine in 1 ml of dry DMF was added 0.073 ml (0.425 mmol) of pentafluorophenyl trifluoroacetate. The reaction was stirred for 1 h and concentrated. Residual DMF was removed by co-evaporation with toluene. The resultant solids were dissolved in 50 ml of ethyl acetate, and washed with 50 ml of 1M sodium dihydrogen phosphate (pH=4.5), followed promptly by 50 ml of water and then 50 ml of saturated sodium chloride solution and dried over sodium sulfate. The solvents were evaporated, and the solids were dissolved in 10 ml of ethyl ether. Then 30 ml of hexane was added. The resulting solution was sonicated and cooled. Crystallized product was collected by filtration washed with hexane and dried to afford 65 mg (51%) of the title compound as an orange solid. $^1$H NMR (DMSO-d$_6$) δ: 8.21 (s, 1H), 7.74 (s, 1H), 6.75 (s, 1H), 6.54 (s, 1H), 2.74 (t, J=8.8 Hz, 2H), 2.42 (m, 2H), 2.24 (s, 3H), 1.57 (m, 2H), 1.47 (m, 2H).

5-(2,4-Dimethoxyphenyl)pentanoic Acid (4a)

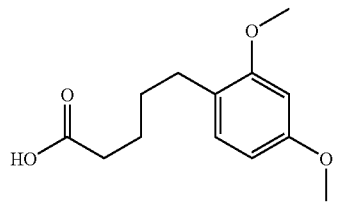

A 1-L hydrogenation flask was charged with 36.2 g of 5-(2,4-dimethoxyphenyl)-4-pentenoic acid (3a) and 400 ml of glacial acetic acid. The flask was flushed with argon and 2 g of (10% Pd/C) were added to the flask, which was then attached to the hydrogenator. The hydrogenation bottle was evacuated, and charged with hydrogen to 40 to 50 psi. The reaction was run overnight until no further hydrogen was being consumed. The solution was filtered through Cellite (diatomaceous earth). The solvent was evaporated, and the residue dried in vacuo. The yield was 99%. $^1$H NMR (DMSO-d$_6$) δ: 12.01 (br s, 1H), 6.99 (d, J=8.2 Hz, 1H), 6.49 (d, J=2 Hz, 1H), 6.41 (dd, J$_1$=2 Hz, J$_2$=8.2 Hz, 1H), 3.74 (s, 3H), 3.72 (s, 3H), 2.45 (t, 2H), 2.20 (t, 2H), 1.47 (m, 4H).

Methyl 5-(2,4-dihydroxyphenyl)pentanoate (5a)

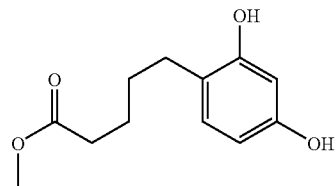

A 1 liter 3 neck round-bottomed flask was charged with 35.7 g (150 mmols) of the 5-(2,4-dimethoxyphenyl)-pentanoic acid (4a) and a stir bar. The flask was set into a suitably sized heating mantle supported on a stirring plate with a strong stirring magnet. The flask was fitted with a thermometer, reflux condenser, and argon inlet. Then 400 ml of acetic acid was added via the thermometer port. The mixture was stirred and warmed to dissolve the solid. This was followed by addition of 68 ml (600 mmols) of 48% aqueous hydrobromic acid. The thermometer was replaced and the flask was flushed with argon. With the cooling water on, the flask was heated to reflux. The reflux was maintained for 16 hours, the mixture was cooled and concentrated on a rotary evaporator. 1 L of methanol was added, and HCl was bubbled in for 5 minutes with a sparger, at a moderate rate. The warm solution was allowed to cool and evaporated. The resulting syrup dissolved in 200 ml of ethyl acetate. The solution was washed with 100 ml water, twice with 100 ml of saturated sodium bicarbonate and once with saturated sodium chloride. The organic layer was dried over sodium sulfate and evaporated to a syrup. The crude product was purified on silica eluting with 3:1 to 2:1 hexane-ethyl acetate. Concentration of the pure product fractions afforded 18.5 g (55%) of desired product. $^1$H NMR (DMSO-d$_6$) δ: 9.01 (s, 1H), 8.92 (s, 1H), 6.75 (d, J=8.2 Hz, 1H), 6.23 (d, J=2 Hz, 1H), 6.10 (dd, J$_1$=2 Hz, J$_2$=8.2 Hz, 1H), 3.56 (s, 3H), 2.37 (t, J=7 Hz, 2H), 2.29 (t, J=7 Hz, 2H), 1.48 (m, 4H).

2-({2,4-Dihydroxy-5-[4-(methoxycarbonyl)butyl]phenyl}carbonyl)benzoic Acid (14a)

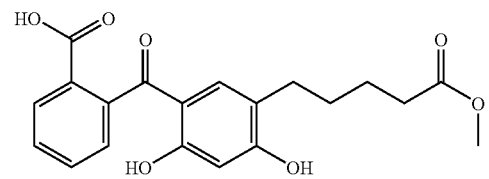

A 2-liter round-bottomed flask was charged with 12.83 g (86.6 mmoles) of phthalic anhydride and a stir bar. Anhydrous 1,2-dichloroethane (190 ml) was added. The flask was flushed with argon, and a reflux condenser was added to the flask. A drying tube was added to the top of the condenser. The mixture was stirred for 30 minutes. (The solid did not dissolve completely.) Then 28.6 g (214.5 mmoles) of aluminum chloride was added (by momentarily removing the condenser). Most solids were dissolved; a greenish-yellow solution results. Stirring was continued for another 30 minutes while a solution of 18.5 g (82.5 mmoles) of methyl-5-(2,4-dihydroxyphenyl)-pentanoate (5a) in 130 ml of dichloroethane was made. This solution was poured into the flask, the headspace was flushed with argon, and the condenser was replaced. With good stirring, the solution in the flask was heated to a light reflux for 30 to 60 minutes. The solution in the flask became slightly warm and turned dark. HCl gas was evolved for about 10-20 minutes. Then the solution was cooled to room temperature. A tarry precipitate formed. The reaction was concentrated to a gum. To this material a mixture of ice (400 g) and concentrated HCl (200 ml) was added followed by 500 ml of ethyl acetate. The flask was capped with a septum and placed on an orbital shaker until all solid dissolved. The mixture was transferred to a 2-liter separatory funnel. The organic layer was separated, washed with 400 ml of 1 N HCl, 2×200 ml of saturated NaCl and dried over sodium sulfate. Concentration afforded an oil. To this material, 200 ml of dichloromethane was added. The resulting solution was sonicated for 30 minutes, and then cooled to −20° C. for 2 hours. The crystalline precipitate was filtered off, washed with 2:1 hexanes/dichloromethane, followed by 4:1 hexanes/dichloromethane and dried. Yield was 20.0 g (65%).

5-(12,15-Dihydroxy-1-oxospiro[3-hydroisobenzofuran-3,9'-xanthene]-11-yl)pentanoic Acid (17a)

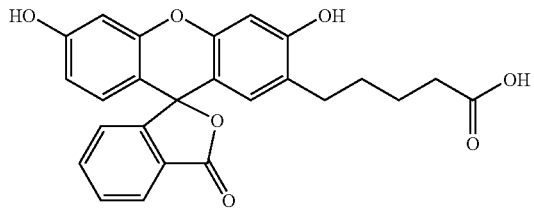

A mixture of resorcinol (7.65 g. 69.5 mmol), benzophenone 14a (17.25 g, 46.3 mmol) and 425 ml of trifluoroacetic acid was stirred to dissolve the solids. The solution was cooled to 0° C. (ice/water bath). To the cold solution, 178 ml (2.78 moles) of methanesulfonic acid was added slowly (about 10 minutes) using addition funnel. The reaction was stirred at 0° C. for 20 h and concentrated. A mixture of ice and water (1600 ml) was added. Precipitated material was extracted with ethyl acetate. The extract was washed with saturated NaCl, dried over $Na_2SO_4$ and concentrated. The evaporation residue was dissolved in 900 ml of 1 M sodium hydroxide. The solution was transferred to a 1-L Erlenmeyer flask and warmed. During the heating the solution gradually changed from blue to a fluorescent orange-pink color. When the temperature reached 70° C., the heat was turned off and the stirring was continued while the solution reached a maximum temperature of 70-80° C., then gradually cooled; after it had been around 70° C. for about 20 minutes, it was cooled to room temperature with an ice bath. With good stirring, an equivalent amount (75 ml) of 12 N HCl was slowly added. A bright orange precipitate formed. Then, with 0.1 N HCl or NaOH as needed, the pH was adjusted to about 2-3. The resulting precipitate was filtered, washed water and dried. The crude dye was chromatographed on silica eluting with 75% ethyl acetate, 2% methanol, 1% hexanes, 2% acetic acid. Pure product fractions were concentrated and triturated in water for 2 to 3 hours to remove traces of acid. Solid obtained was filtered and dried in vacuum. Yield was 12.3 g (61.4% yield). $^1$H NMR (DMSO-$d_6$) δ: 11.9 (br s, 1H), 10.11 (br s, 2H), 8.00 (d, J=7.3 Hz, 1H), 7.78 (t, J=7.3 Hz, 1H), 7.70 (t, J=7.3 Hz, 1H), 7.23 (d, J=7.3 Hz, 1H), 6.70 (s, 1H), 6.66 (s, 1H), 6.52 (s, 2H), 6.35 (s, 1H), 2.33 (t, J=5.5 Hz, 2H), 2.10 (t, J=6 Hz, 2H), 1.35 (m, 4H).

2,3,4,5,6-Pentafluorophenyl 5-(12,15-dihydroxy-1-oxospiro[3-hydroisobenzofuran-3,9'-xanthene]-11-yl)pentanoate (18a)

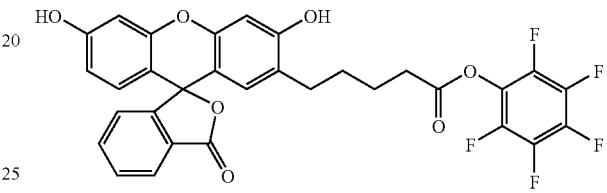

Dye 17a (10.84 g, 25.1 mmol) was dissolved in 100 ml of dry DMF and 9.7 ml (55.9 mmoles) of diisopropylethylamine were added. When dissolution was complete, 8 ml (46.6 mmoles) of PFP-TFA was added. After stirring for 1 h, the mixture was stripped down and co-evaporated with toluene. The solids were dissolved in 200 ml of ethyl acetate, and washed with 150 ml of 1M potassium dihydrogen phosphate followed by 100 ml of water and 100 ml of saturated sodium chloride solution and dried over sodium sulfate. The solvents were evaporated, and the solids were dissolved in 50 ml of ethyl ether. Hexane (400 ml) was added, and the resulting solution was sonicated. This produced gradual crystallization of the product, which was filtered off, washed with additional hexane, and dried. Yield was 14.2 g (95%). $^1$H NMR (DMSO-$d_6$) δ: 10.16 (s, 1H), 10.11 (s, 1H), 7.97 (d, J=7.4 Hz, 1H), 7.77 (t, J=7.4 Hz, 1H), 7.69 (t, J=7.4 Hz, 1H), 7.24 (d, J=7.4 Hz, 1H), 6.72 (s, 1H), 6.66 (s, 1H), 6.53 (s, 2H), 6.39 (s, 1H), 2.71 (t, J=7 Hz, 2H), 2.40 (m, 2H), 1.55 (m, 2H), 1.44 (m, 2H).

5-(12,15-Dihydroxy-1-oxospiro[3-hydroisobenzofuran-3,9'-xanthene]-11-yl)-N-(6-hydroxyhexyl)pentanamide (29)

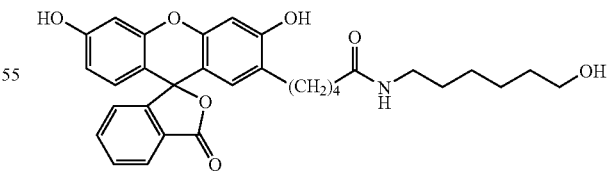

PFP ester 18a (15.74 g, 26.3 mmol) was dissolved in 100 ml of anhydrous DMF. The solution was cooled to 0° C. using ice/water bath. A solution of 3.7 g (31.55 mmoles) of 6-aminohexanol and 5.5 ml (31.55 mmoles) of diisopropylethylamine, previously dissolved in DMF (20 ml), was added to the dropping funnel. The solution was allowed to rise gradually to room temperature. The reaction mixture was not worked up at this point, but rather, the next reaction was carried out in the same vessel.

5-(12,15-Dihydroxy-1-oxospiro[3-hydroisobenzofuran-3,9'-xanthene]-11-yl)-N-{6-[bis(4-methoxyphenyl)phenylmethoxy]hexyl}pentanamide (30)

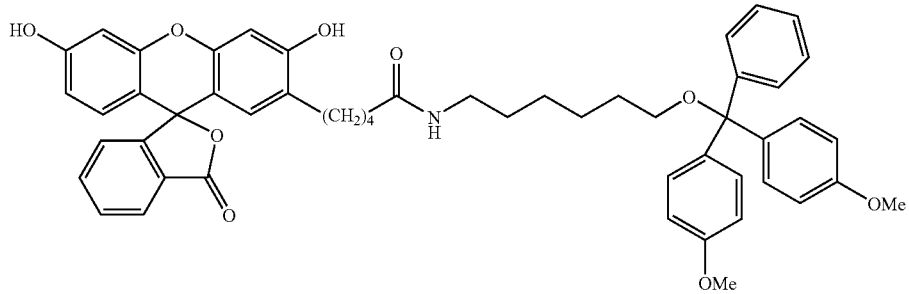

To the flask was added 6.9 ml (39.5 mmole) of diisopropylethylamine (DIEA) and 13.4 g (39.5 mmoles) of 4,4'-dimethoxytrityl chloride. The reaction was allowed to proceed for 2 hours. When reaction was complete next step was performed without isolating the DMT intermediate.

11-[4-(N-{6-[bis(4-methoxyphenyl)phenylmethoxy]hexyl}carbamoyl)butyl]-15-(2,2-dimethylpropanoyloxy)-1-oxospiro[3-hydroisobenzofuran-3,9'-xanthene]-12-yl 2,2-dimethylpropanoate (31)

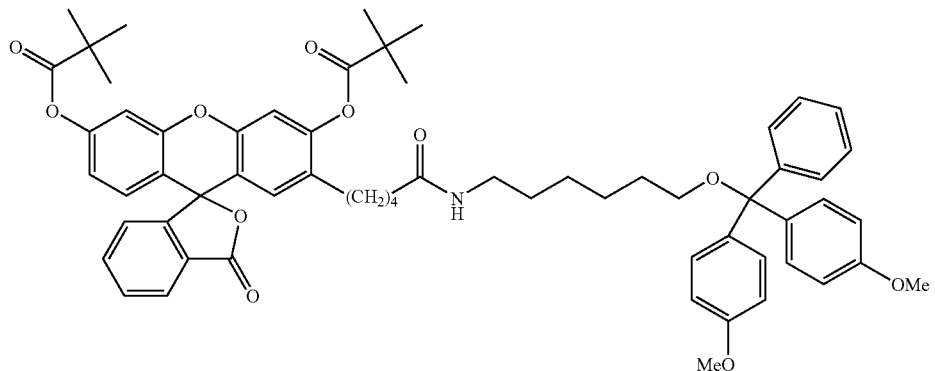

To the flask was added 15.66 ml (196.5 mmoles) of N-methylimidazole and 15.63 ml (77.06 mmol) of trimethylacetic anhydride. The reaction was allowed to proceed for an hour and a half. When the reaction was done, about 10 ml of water was added to the reaction and the mixture was warmed to 50 degrees for 1-2 hours, to hydrolyze residual trimethylacetic anhydride. The mixture was allowed to cool, and the solvent was evaporated on a rotary evaporator. The solids were dissolved in 500 ml of ethyl acetate. The resulting solution was washed twice with 300 ml of sodium bicarbonate solution, 200 ml of saturated sodium chloride solution and dried over sodium sulfate. The solution was transferred to an evaporating flask, evaporated to oil, transferred to a 500 ml flask, and dried in vacuum overnight. The compound was purified by silica gel chromatography eluting with 1:1 hexanes/ethyl acetate. Evaporation of the pure product fractions afforded 18.4 g (70%) of the desired product 31 as a white, amorphous solid. $^1$H NMR (DMSO-$d_6$) δ: 8.05 (d, J=7.1 Hz, 1H), 7.81 (t, J=7.4 Hz, 1H), 7.74 (t, J=7.4 Hz, 1H), 7.64 (t, J=5 Hz, 1H), 7.4-7.15 (m, 12H), 6.89 (m, 6H), 6.75 (s, 1H), 3.72 (s, 6H), 2.92 (m, 4H), 2.30 (t, J=7 Hz, 2H), 1.93 (t, 2H), 1.48 (m, 2H), 1.4-1.1 (m, 10H overlapping with 1.31 ppm (s, 9H) and 1.30 ppm (s, 9H)).

15-(2,2-dimethylpropanoyloxy)-11-{4-[N-(6-hydroxyhexyl)carbamoyl]butyl}-1-oxospiro[3-hydroisobenzofuran-3,9'-xanthene]-12-yl 2,2-dimethylpropanoate (32)

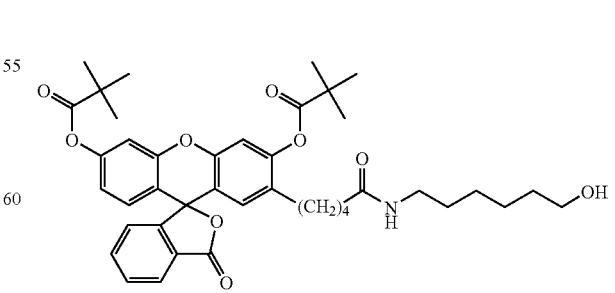

The DMT intermediate 31 (18.4 g, 18.4 mmoles) was dissolved in 150 ml of dichloromethane. To this solution methanol (100 ml) was added followed by 2.6 ml (34.2 mmoles) of trifluoroacetic acid (TFA). The reaction was allowed to proceed for two hours and quenched with triethylamine (7 ml, 50 mmol). The solution was evaporated, and dissolved in about 200 ml of ethyl acetate and extracted with 150 ml of sodium bicarbonate solution, and then with a similar portion of saturated sodium chloride solution. It was dried over sodium sulfate and purified by silica gel chromatography eluting with 1:1 hexanes/ethyl acetate followed by pure ethyl acetate. The appropriate fractions were evaporated to an amorphous solid. The yield was 11.3 g (88%). $^1$H NMR (DMSO-$d_6$) δ: 8.06 (d, J=7.4 Hz, 1H), 7.82 (t, J=7.4 Hz, 1H), 7.76 (t, J=7.4 Hz, 1H), 7.66 (t, J=5 Hz, 1H), 7.37 (d, J=7.4 Hz, 1H), 7.24 (d, J=2 Hz, 1H), 7.22 (s, 1H), 6.95-6.80 (m, 2H), 6.75 (s, 1H), 4.33 (t, J=5 Hz, 1H), 3.36 (m, 2H), 2.94 (m, 2H), 2.31 (t, J=7 Hz, 2H), 1.93 (t, J=7 Hz, 2H), 1.4-1.1 (m, 12H overlapping with 1.33 ppm (s, 9H) and 1.30 ppm (s, 9H)).

11-{4-[N-(6-{[bis(methylethyl)amino](2-cyanoethoxy)phosphinooxy}hexyl)carbamoyl]butyl}-15-(2,2-dimethylpropanoyloxy)-1-oxospiro[3-hydroisobenzofuran-3,9'-xanthene]-12-yl 2,2-dimethylpropanoate (33)

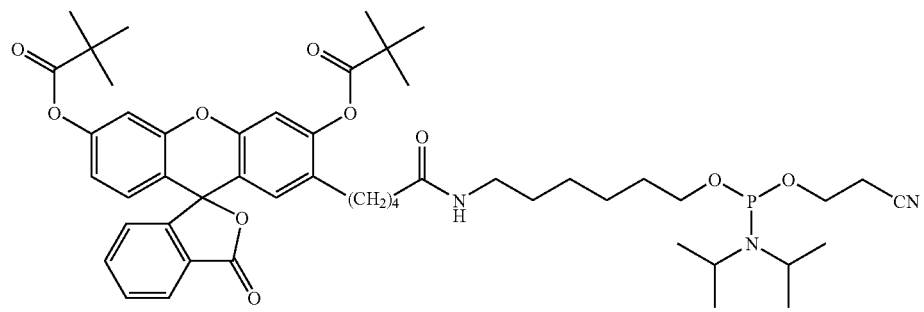

An oven-dried 250 ml flask was charged with 5.6 g (8 mmols) of 32 and flushed with argon. This was dissolved in 50 ml of dichloromethane, and 1.37 g (8 mmols) of diisopropylammonium tetrazolide was added. The flask was flushed with argon again and capped with a septum. Then, 3.31 ml (10.4 mmols) of the bis-phosphoramidite was added via syringe through the septum. After two hours another 0.7 g of diisopropylammonium tetrazolide and 1 ml of bis-phosphoramidite were added to complete the reaction. The reaction mixture was transferred to a separatory funnel and washed with 50 ml of saturated sodium bicarbonate solution, twice with 75 ml of saturated sodium chloride solution, and dried over sodium sulfate. The solvent was removed by evaporation. The phosphoramidite was purified by precipitation in pentane. The yield was 7.2 g. $^1$H NMR (DMSO-$d_6$) δ: 8.06 (d, J=7.4 Hz, 1H), 7.82 (t, J=7.4 Hz, 1H), 7.76 (t, J=7.4 Hz, 1H), 7.65 (t, J=5 Hz, 1H), 7.35 (d, J=7.4 Hz, 1H), 7.23 (d, J=2 Hz, 1H), 7.21 (s, 1H), 6.95-6.80 (m, 2H), 6.75 (s, 1H), 3.70 (m, 2H), 3.50 (m, 4H), 2.94 (m, 2H), 2.74 (t, J=6 Hz, 2H), 2.31 (t, J=7 Hz, 2H), 1.93 (t, J=7 Hz, 2H), 1.45 (m, 2H), 1.4-1.1 (m, 10H overlapping with 1.33 ppm (9H) and 1.30 ppm singlets (9H)), 1.11 (t, 6 Hz, 12H). $^{31}$P NMR (DMSO-$d_6$) δ: 146.67 (s).

Derivatization of Amino-Tailed Oligonucleotides Using Compounds of the Invention.

In order to evaluate the utility of the compounds of the invention as amine derivatizing agents post-synthetic modification of aminohexyl-tailed oligonucleotides (ODNs) was tested as shown above in Scheme 13. The reactions between the reagents and triethylammonium salts of aminohexyl-modified ODNs were done in organic (DMSO) solvent. Small (2-5×) molar excesses of the reactive dyes led to essentially quantitative (>90%) labeling of the amine-containing ligand. The conjugates were purified by gel-electrophoresis and reverse-phase HPLC. Analysis of absorbance and fluorescence spectra of the conjugates demonstrated successful dye incorporation into the amine-containing ligand and expected spectral characteristics.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound having a formula selected from the group consisting of:

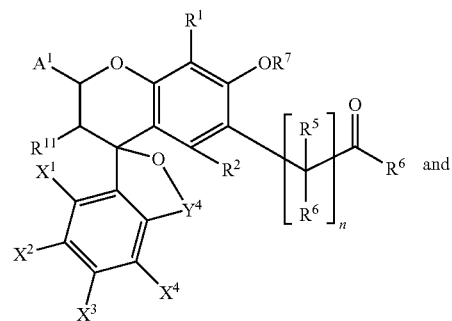

-continued

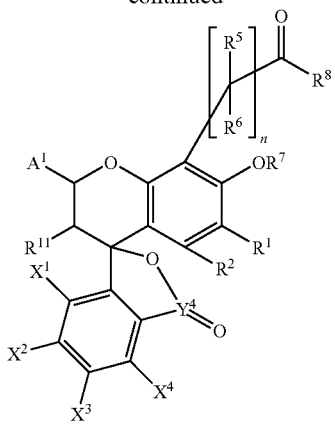

wherein

Y$^4$ is C, S, or SO;

each X$^1$, X$^2$, X$^3$ and X$^4$ is a member independently selected from the group consisting of H, halogen, cyano, halo (C$_1$-C$_8$)alkyl, (C$_1$-C$_8$)alkyl, (C$_1$-C$_8$)alkoxy, (C$_1$-C$_8$) alkylthio, (C$_2$-C$_8$)alkenyl, (C$_2$-C$_8$)alkynyl, SO$_3$H and CO$_2$H, or any two adjacent X$^1$, X$^2$, X$^3$, and X$^4$ are combined to form a fused aromatic or heteroaromatic ring that is optionally further substituted with from one to four substituents selected from the group consisting of halogen cyano, carboxy, sulfo, hydroxy, amino, mono (C$_1$-C$_6$)alkylamino, di(C$_1$-C$_6$)alkylamino, (C$_1$-C$_6$) alkyl, (C$_1$-C$_6$)alkylthio and (C$_1$-C$_6$)alkoxy;

the moiety

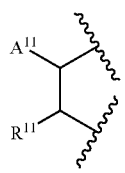

is a member selected from the group consisting of:

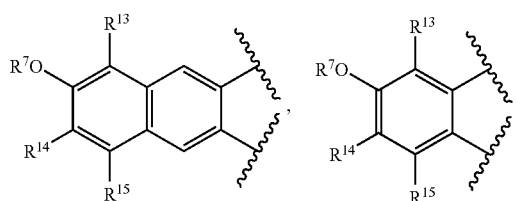

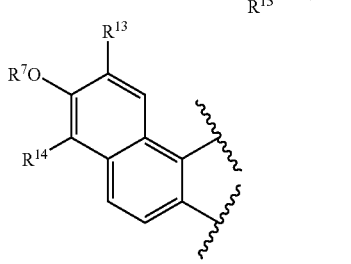

optionally substituted with a member independently selected from the group consisting of halogen, cyano, halo(C$_1$-C$_8$)alkyl, (C$_1$-C$_8$)alkoxy, (C$_1$-C$_8$)alkylthio, (C$_2$-C$_8$)alkenyl, (C$_2$-C$_8$)alkynyl, aryl, heteroaryl, SO$_2$H and CO$_2$H;

each R$^1$, R$^2$, R$^{13}$, R$^{14}$ or R$^{15}$ is a member independently selected from the group consisting of H, halogen, cyano, halo(C$_1$-C$_8$)alkyl, (C$_1$-C$_8$)alkyl, (C$_1$-C$_8$)alkylthio, (C$_1$-C$_8$)alkoxy, aryl and heteroaryl, or R$^{14}$ and R$^{15}$ are combined with the atoms which attach them to form a 5- or 6-membered aromatic ring;

each R$^5$ or R$^6$ is a member independently selected from the group consisting of H, (C$_1$-C$_8$)alkyl, aryl, heteroaryl, aryl(C$_1$-C$_4$)alkyl and heteroaryl(C$_1$-C$_4$)alkyl;

R$^7$ is H or a hydroxyl protecting group;

R$^8$ is NR$^9$W(Y$^2_p$L), hydroxy, or a leaving group that can be displaced by a nucleophilic reagent;

W is a linking group selected from the group consisting of a (C$_2$-C$_{50}$)alkylene, heteroalkylene, (C$_2$-C$_{50}$)cycloalkylene, heterocycloalkylene, (C$_6$-C$_{50}$)arylene group, a heteroarylene group, (C$_2$-C$_{50}$)alkylenearylene group, a heteroalkylenearylene group, optionally substituted with at least one substituent independently selected from the group consisting of (C$_1$-C$_8$)alkyl, hydroxy, protected hydroxy, alkoxy, amino, protected amino, hydrazino, thio, protected thio and aryl;

R$^9$ is H, alkyl or combined with W to form a heterocycloalkylene, heterocycloalkylenearylene, or heterocycloalkyleneheteroarylene linking group;

Y$^2$ is a linking group selected from the group consisting of:

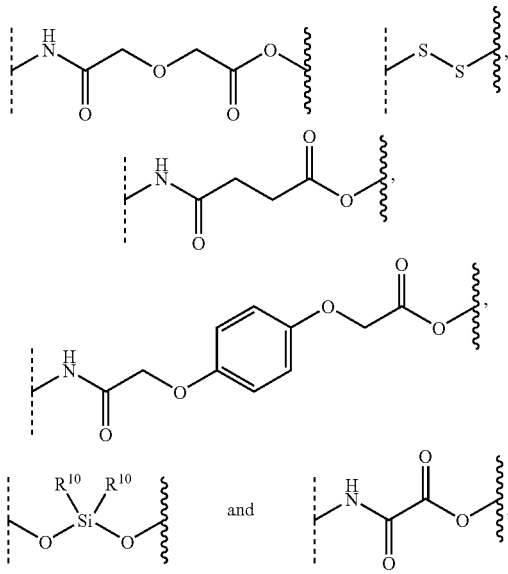

wherein dashed line indicates the point of attachment to L and the wavy line indicates the point of attachment to the rest of the molecule;

each R$^{10}$ is independently (C$_1$-C$_8$)alkyl or (C$_1$-C$_8$)alkoxy;

the subscript p is an integer of from 0 to 1;

L is solid support when p is 1 and L is a member selected from the group consisting of an O-phosphoramidite or a reactive functional group when p is 0; and the subscript n is an integer of from 4 to about 20.

2. The compound in accordance with claim 1, selected from the group consisting of 5-(12,15-Dihydroxy-1-oxospiro

[3-hydroisobenzofuran-3,9'-xanthene]-11-yl)pentanoic acid; 2,3,4,5,6-Pentafluorophenyl 5-(12,15-dihydroxy-1-oxospiro [3-hydroisobenzofuran-3,9'-xanthene]-11-yl)pentanoate; 5-(12,15-Dihydroxy-1-oxospiro[3-hydroisobenzofuran-3,9'-xanthene]-11-yl)-N-(6-hydroxyhexyl)pentanamide; 5-(12,15-Dihydroxy-1-oxospiro[3-hydroisobenzofuran-3,9'-xanthene]-11-yl)-N-{6-[bis(4-methoxyphenyl)phenylmethoxy]hexyl}pentanamide; 11-[4-(N-{6-[bis(4-methoxyphenyl)phenylmethoxy]hexyl}carbamoyl)butyl]-15-(2,2-dimethylpropanoyloxy)-1-oxospiro[3-hydroisobenzofuran-3,9'-xanthene]-12-yl 2,2-dimethylpropanoate; 15-(2,2-dimethylpropanoyloxy)-11-{4-[N-(6-hydroxyhexyl)carbamoyl]butyl}-1-oxospiro[3-hydroisobenzofuran-3,9'-xanthene]-12-yl 2,2-dimethylpropanoate; and 11-{4-[N-(6-{[bis(methylethyl)amino](2-cyanoethoxy)phosphinooxy}hexyl)carbamoyl]butyl}-15-(2,2-dimethylpropanoyloxy)-1-oxospiro[3-hydroisobenzoftiran-3,9'-xanthene]-12-yl 2,2-dimethylpropanoate.

3. The compound in accordance with claim 1, wherein $R^8$ is $NR^9W(Y^2_pL)$.

4. The compound in accordance with claim 1, wherein $R^9$ and W are combined together to form a linking group comprising a prolinol group.

5. The compound in accordance with claim 3, wherein p is 0.

6. The compound in accordance with claim 3, wherein p is 1.

7. The compound in accordance with claim 3, wherein; each $X^1$, $X^2$, $X^3$ and $X^4$ is a member independently selected from the group consisting of H, halogen, cyano, halo $(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, $SO_3H$ and $CO_2H$.

8. The compound in accordance with claim 7, wherein $Y^4$ is C.

9. A composition comprising a compound according to claim 1 covalently attached to a solid support.

10. A method for preparing a compound of claim 1, wherein $R^8$ is $NR^9W(Y^2_pL)$, and L is a reactive functional group; said method comprising contacting a compound of claim 1 wherein $R^8$ is a leaving group with a nucleophilic linking group component $HNR^9W(Y^2_pL)$.

11. A method for preparing a compound of claim 1, wherein $R^8$ is $NR^9W(Y^2_pL)$, and L is a O-phosphoramidite, said method comprising contacting a compound of claim 7, wherein $R^8$ is $NR^9W(Y^2_pL)$, and L is a reactive functional group; with a phosphoramidite reagent under conditions sufficient to covalently attach a phosphoramidite moiety.

12. A method for preparing a labeled biological agent, said method comprising contacting an unlabeled biological agent with a compound of claim 1 under conditions sufficient to covalently attach said compound to said biological agent and form said labeled biological agent.

13. The method in accordance with claim 12, wherein said biological agent is a nucleotide, a modified nucleotide, a oligonucleotide, or a modified oligonucleotide.

14. The method in accordance with claim 13, wherein said oligonucleotide comprises one or more modified nucleotide bases.

15. A nucleic acid covalently modified with a substituent having the formula selected from the group consisting of:

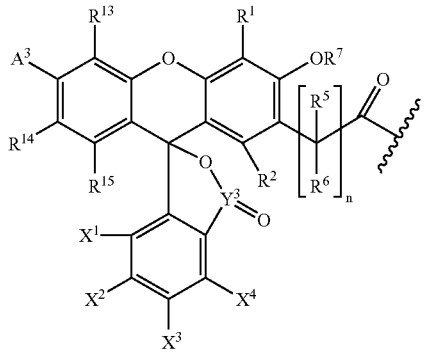

and

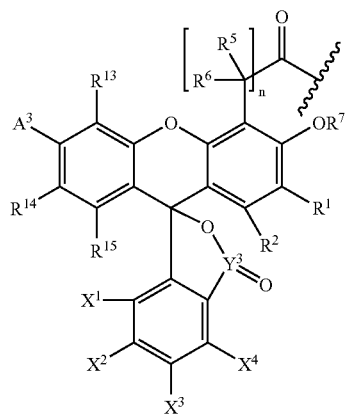

wherein, $A^3$ is OH or a protected hydroxyl group;

each $R^5$ and $R^6$ is independently selected from H, $(C_1-C_8)$ alkyl, aryl and aryl$(C_1-C_4)$alkyl;

$R^7$ is H or a hydroxyl protecting group;

each $R^1$, $R^2$, $R^{13}$, $R^{14}$ and $R^{15}$ is a member independently selected from the group consisting of H, halogen, cyano, halo$(C_1-C_8)$alkyl, $(C_1-C_8)$alkyl, $(C_1-C_8)$alkylthio, $(C_1-C_8)$alkoxy, aryl and heteroaryl; or $R^{14}$ and $R^{15}$ is combined with the atoms which attach them to form a 5- or 6-membered aromatic ring;

n is an integer from 4 to about 20;

$Y^4$ is C, S, or SO;

each $X^1$, $X^2$, $X^3$ and $X^4$ is a member independently selected from the group consisting of H, halogen, cyano, halo $(C_1-C_8)$alkyl, $(C_1-C_8)$alkyl, $(C_1-C_8)$alkoxy, $(C_1-C_8)$alkylthio, $(C_2-C_8)$alkenyl, $(C_2-C_8)$alkynyl, $SO_3H$ and $CO_2H$, or any two adjacent $X^1$, $X^2$, $X^3$, and $X^4$ are combined to form a fused aromatic or heteroaromatic ring that is optionally further substituted with from one to four substituents selected from halogen cyano, carboxy, sulfo, hydroxy, amino, mono$(C_1-C_6)$alkylamino, di$(C_1-C_6)$alkylamino, $(C_1-C_6)$alkyl, $(C_1-C_6)$alkylthio and $(C_1-C_6)$alkoxy; and the wavy line indicates the point of attachment to said nucleic acid or said linking group joining said nucleic acid to said substituent.

16. The nucleic acid in accordance with claim 15, further comprising an attached quencher, and attached minor groove binder, or a combination thereof.

17. The nucleic acid in accordance with claim 16, wherein said substituent is attached at the 3'-end of said nucleic acid and said quencher and said minor groove binder are attached at the 5'-end of said nucleic acid.

18. The nucleic acid in accordance with claim 16, wherein said substituent is attached at the 5'-end of said nucleic acid and said quencher and said minor groove binder are attached at the 3'-end of said nucleic acid.

19. The compound in accordance with claim 1, wherein said compound has an emission wavelength of from about 400 nm to about 1200 nm.

20. The compound in accordance with claim 1, wherein said compound has an emission wavelength of from about 400 nm to about 850 nm.

* * * * *